United States Patent
Yang et al.

(10) Patent No.: US 9,382,265 B2
(45) Date of Patent: Jul. 5, 2016

(54) OXAZOLIDONE COMPOUND, PREPARING METHOD AND APPLICATION THEREOF

(71) Applicants: SHANGHAI INSTITUTE OF MATERIA MEDICA, CHINESE ACADEMY OF SCIENCES, Shanghai (CN); ZHE JIANG JUTAI PHARMACEUTICAL CO., LTD., Quzhou (CN)

(72) Inventors: Yushe Yang, Shanghai (CN); Tao Xue, Shanghai (CN); Shi Ding, Shanghai (CN); Bin Guo, Shanghai (CN)

(73) Assignees: Shanghai Institute of Materia Medica, Chinese Academy of Sciences, Shanghai (CN); Zhe Jiang Jutai Pharmaceutical Co., Ltd., Quzhou (CN)

( * ) Notice: Subject to any disclaimer, the term of this patent is extended or adjusted under 35 U.S.C. 154(b) by 0 days.

(21) Appl. No.: 14/761,843

(22) PCT Filed: Dec. 30, 2013

(86) PCT No.: PCT/CN2013/090833
§ 371 (c)(1),
(2) Date: Jul. 17, 2015

(87) PCT Pub. No.: WO2014/110971
PCT Pub. Date: Jul. 24, 2014

(65) Prior Publication Data
US 2015/0361091 A1    Dec. 17, 2015

(30) Foreign Application Priority Data
Jan. 18, 2013 (CN) .......................... 2013 1 0020040

(51) Int. Cl.
*C07D 498/04* (2006.01)
*C07D 519/00* (2006.01)

(52) U.S. Cl.
CPC ............ *C07D 498/04* (2013.01); *C07D 519/00* (2013.01)

(58) Field of Classification Search
CPC .................................................... C07D 498/04
USPC ....................................... 544/101; 514/230.2
See application file for complete search history.

(56) References Cited

FOREIGN PATENT DOCUMENTS

CN          102260277 A      11/2011

OTHER PUBLICATIONS

International Search Report (English Translation) corresponding to PCT/CN2013/090833 mailed Apr. 3, 2014 (4 pages).
Buon, C. et al, "Synthesis of 3-Substituted and 2,3-Disubstituted-4H-1,4-Benzoxazines," *Tetrahedron* (2000) 56:605-614.
Camm, A. John et al., "Edoxaban a New Oral Direct Factor Xa Inhibitor," *Drugs* (2011) 71(12): 1508-1526.
Chacun-Lefevre, L. et al., "Synthesis of 3-Substituted-4H-1,4-Benzoxazines," *Tetrahedron Letters* (1998) 39:5763-5764.
Cui, Yingjie et al., "Stereocontrolled Synthesis of Tricyclic Fused Oxazolidinone as Antibacterial Agent," *J. Heterocyclic Chem.* (Jul.-Aug. 2006) 43:1071-1075.
Guo, Bin et al., "Synthesis and biological evaluation of novel benzoxazinyl-oxazolidinones as potential antibacterial agents," *Bioorg. Med. Chem. Lett.* 23 (2013) 3697-3699.
Guo, Bin et al., "Solubility-Driven Optimization of (Pyridin-3-yl) Benzoxazinyl-oxazolidinones Leading to a Promising Antibacterial Agent," *J. Med. Chem.* (2013) 56:2642-2650.
Pinto, Donald J. P. et al., "Discovery of 1-(4-Methoxyphenyl)-7-oxo-6-(4-(2-oxopiperidin-1-yl)phenyl)-4,5,6,7-tetrahydro-1H-pyrazolo[3,4-c]pyridine-3-carboxamide (Apixaban, BMS-562247), a Highly Potent, Selective, Efficacious, and Orally Bioavailable Inhibitor of Blood Coagulation Factor Xa," *J. Med. Chem.* (2007) 50(22):5339-5356.
Xin, Qisheng et al., "Design, Synthesis, and Structure—Activity Relationship Studies of Highly Potent Novel Benzoxazinyl-Oxazolidinone Antibacterial Agents," *J. Med. Chem.* (2011) 54:7493-7502.

*Primary Examiner* — Kahsay Habte
(74) *Attorney, Agent, or Firm* — Mintz, Levin, Cohn, Ferris, Glovsky and Popeo, P.C.

(57) ABSTRACT

The present invention relates to the field of a pharmaceutical compound, and more specifically, relates to a new oxazolidone compound, an enantiomer, a diastereoisomer and a raceme thereof, and a mixture thereof, and a pharmaceutically acceptable salt thereof, a preparation method thereof, an application thereof as a bioactive substance in a drug. The compound in the present invention has strong anticoagulant activity, does not affect the activity of thrombin, and can reduce the risk of hemorrhage. A pharmacokinetics experiment shows that the compound in the present invention further has good metabolic characteristics, and has a far better oral bioavailability than a positive contrastive agent rivaroxaban.

12 Claims, 1 Drawing Sheet

OXAZOLIDONE COMPOUND, PREPARING METHOD AND APPLICATION THEREOF

TECHNICAL FIELD

The present invention relates to the field of pharmaceutical compounds, and more particularly, relates to a novel oxazolidone compound, an enantiomer, diastereoisomer and raceme thereof as well as their mixtures, and a pharmaceutically acceptable salt thereof, a preparation method thereof, and use thereof as a bioactive substance in medicines.

BACKGROUND ART

In spite of the anticoagulant drugs such as warfarin, heparin, aspirin and clopidogrel, thrombotic diseases still remain to be the leading cause of death in developed countries [J. Med. Chem. 2007, 50, 5339]. Thrombosis formed in the arterial circulation system can cause acute myocardial infarction or ischemic stroke, and deep venous thrombosis formed in the venous circulation system can cause diseases such as chronic lower limb pain and pulmonary embolism. It is estimated that 100,000 people die of deep venous thrombosis and pulmonary embolism each year merely in the United States [J. Med. Chem. 2010, 53, 5339].

The existing antithrombotic drugs are divided into antiplatelet drugs, anticlotting drugs and fibrinolytic drugs. Among them, anticlotting drugs are the main contents of antithrombosis treatment, which drugs are mainly thrombin inhibitors and vitamin K antagonists. Thrombin inhibitors represented by heparin and low molecular weight heparin have disadvantages such as ineffective oral administration, non-selective inhibition and high bleeding risk. Although vitamin K antagonists represented by warfarin can be taken orally. They also have the disadvantages such as small treatment index, high bleeding risk, and etc.

Activated serine protease factor Xa (FXa) plays a central role in the coagulation cascade system by catalyzing the conversion of prothrombin to thrombin. Thrombin has multiple coagulation functions, which include converting fibrinogen to fibrin, activating platelets, activating other coagulation factors, amplifying the function of FXa, and so on. Inhibition of FXa does not affect the activity of the existing thrombin, which can reduce the risk of bleeding, improve safety, and thus better than the direct thrombin inhibitor. Therefore, FXa inhibitors have become an important area for the research and development of new anticoagulant (thrombus) drugs, wherein their representative drugs, rivaroxaban and apixaban, have been sold on market, while some other drugs are in the stage of clinical research [Drugs, 2011, 7(12), 1503; Current Topics in Medicinal Chemistry, 2010, 10, 257-269; Nature Reviews, 2011, 10, 61].

SUMMARY OF INVENTION

Upon extensive research, the inventors has synthesized a series of compounds, and by using FXa enzyme inhibition activity screening, metabolic screening, anticoagulant activity experiment and other experiments, found for the first time that the compounds represented by the following general formula (I) have potent activity against FXa, excellent pharmacokinetic and physiochemical properties, which are particularly suitable to be used as anticoagulant agents for the treatment of thrombus-related diseases. The inventors completed the present invention on such basis.

An objective of the present invention is to provide a novel oxazolidone compound represented by the following general formula (I), an enantiomer, diastereoisomer and raceme thereof as well as their mixtures, and a pharmaceutically acceptable salt thereof;

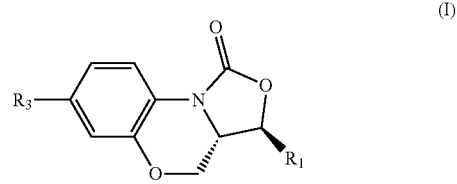

wherein, $R_1$ is —$CH_2NHCOR_2$, —$CH_2CH_2NHCOR_2$, —$CONHR_2$, —$CONHCH_2R_2$, —$CH_2NHCONHR_2$ or —$CH_2NHCOCONHR_2$; preferably, —$CH_2NHCOR_2$, —$CONHR_2$, —$CH_2NHCONHR_2$ or —$CH_2NHCOCONHR_2$;

$R_2$ is substituted or unsubstituted $C_1$-$C_6$ alkyl, substituted or unsubstituted —$(CH_2)_n$—X—$C_mH_{2m+1}$, substituted or unsubstituted phenyl, substituted or unsubstituted 5- or 6-membered heterocyclic group, or substituted or unsubstituted benzo 5- or 6-membered heterocyclic group;

in said substituted or unsubstituted —$(CH_2)_n$—X—$C_mH_{2m+1}$, X is NH, O or S, and n and m are each an integer and n+m<6;

in the circumstance of substituted $C_1$-$C_6$ alkyl or substituted —$(CH_2)_n$—X—$C_mH_{2m+1}$, the substituent of $C_1$-$C_6$ alkyl or —$(CH_2)_n$—X—$C_mH_{2m+1}$ is a radical selected from the group consisting of: halogen, cyano, nitro, amino, aminomethyl, $C_1$-$C_8$ alkoxy, $C_3$-$C_7$ cycloalkyl or aminoformyl;

in the circumstance of substituted phenyl, the substituent of phenyl is a radical selected from the group consisting of: halogen, —$NO_2$, —CHO, —$CF_3$, —$CONR_4R_5$, —$COR_4$, —$NHR_5$, —$NHCOR_4$, —$OR_5$, —$SO_2R_4$, —$SO_2NHR_5$ or $C_1$-$C_3$ alkyl; said $R_4$ is $C_1$-$C_3$ alkyl, $R_5$ is H or $C_1$-$C_3$ alkyl;

said 5- or 6-membered heterocyclic group or benzo 5- or 6-membered heterocyclic group contains at least one heteroatom selected from N, O or S;

in the circumstance of substituted 5- or 6-membered heterocyclic group or substituted benzo 5- or 6-membered heterocyclic group, the substituent of 5- or 6-membered heterocyclic group or benzo 5- or 6-membered heterocyclic group is a radical selected from the group consisting of: halogen, —$NO_2$, —CHO, —$CF_3$, —$CONR_4R_5$, —$COR_4$, —$NHR_5$, —$NHCOR_4$, —$OR_5$, —$SO_2R_4$, —$SO_2NHR_5$, $C_1$-$C_3$ alkyl; said $R_4$ is $C_1$-$C_3$ alkyl, $R_5$ is H or $C_1$-$C_3$ alkyl;

preferably, $R_2$ is substituted or unsubstituted —$(CH_2)_n$—X—$C_mH_{2m+1}$, substituted or unsubstituted phenyl, substituted or unsubstituted 5- or 6-membered heterocyclic group, or substituted or unsubstituted benzo 5- or 6-membered heterocyclic group;

in the circumstance of substituted —$(CH_2)_n$—X—$C_mH_{2m+1}$, the substituent of —$(CH_2)_n$—X—$C_mH_{2m+1}$ is halogen;

in the circumstance of substituted phenyl, the substituent of phenyl is a radical selected from the group consisting of: halogen, —$OR_5$; said $R_5$ is H or $C_1$-$C_3$ alkyl;

said 5- or 6-membered heterocyclic group or benzo 5- or 6-membered heterocyclic group contains at least one heteroatom selected from N, O or S;

in the circumstance of substituted 5- or 6-membered heterocyclic group or substituted benzo 5- or 6-membered heterocyclic group, the substituent of 5- or 6-membered heterocyclic group or benzo 5- or 6-membered heterocyclic group is halogen or —OR$_5$; said R$_5$ is H or C$_1$-C$_3$ alkyl;

more preferably, R$_2$ is

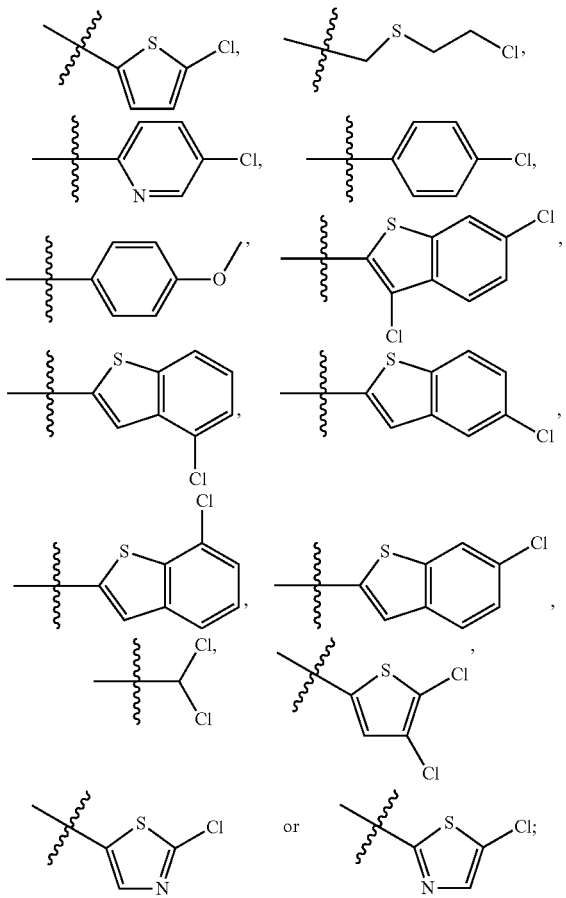

R$_3$ is substituted or unsubstituted C$_1$~C$_3$ amido, substituted or unsubstituted phenyl or substituted or unsubstituted 5- or 6-membered aromatic or non-aromatic heterocyclic group;

in the circumstance of substituted C$_1$~C$_3$ amido, the H on N of said C$_1$~C$_3$ amido can be substituted with C$_1$~C$_3$ alkyl;

in the circumstance of substituted phenyl, the substituent of phenyl is a radical selected from the group consisting of: F, Cl, Br, CN, —NO$_2$, —CF$_3$, —CONR$_4$R$_5$, —COR$_4$, —NHR$_5$, —NHCOR$_4$, —OR$_5$, —SO$_2$R$_4$, —SO$_2$NHR$_5$ or C$_1$-C$_3$ alkyl; said R$_4$ is C$_1$-C$_3$ alkyl, R$_5$ is H or C$_1$-C$_3$ alkyl;

said 5- or 6-membered aromatic heterocyclic group contains at least one heteroatom selected from N, O or S, and in the circumstance of substituted 5- or 6-membered aromatic heterocyclic group, the substituent of 5- or 6-membered aromatic heterocyclic group is a radical selected from the group consisting of: F, Cl, Br, CN, —NO$_2$, —CF$_3$, —CONR$_4$R$_5$, —COR$_4$, —NHR$_5$, —NHCOR$_4$, —OR$_5$, —SO$_2$R$_4$, —SO$_2$NHR$_5$ or C$_1$-C$_3$ alkyl; said R$_4$ is C$_1$-C$_3$ alkyl, R$_5$ is H or C$_1$-C$_3$ alkyl;

said 5- or 6-membered non-aromatic heterocyclic group contains at least one heteroatom selected from N, O or S, and said heterocyclic group can further form a spiroring with another 3- to 6-membered heterocyclic group; and in the circumstance of substituted 5- or 6-membered non-aromatic heterocyclic group, the substituent of 5- or 6-membered non-aromatic heterocyclic group is a radical selected from the group consisting of: oxo, F, Cl, Br, C$_1$-C$_3$ alkyl, CN, —NO$_2$, —CF$_3$, —CONR$_4$R$_5$, —COR$_4$, —COPh, —NHR$_5$, =NH, —NHCOR$_4$, —OR$_5$, —CH$_2$Ph, —SO$_2$R$_4$, —SO$_2$Ph, —SO$_2$NHR$_5$; said R$_4$ is C$_1$-C$_3$ alkyl, R$_5$ is H or C$_1$-C$_3$ alkyl;

preferably, R$_3$ is N-methylacetamido, substituted or unsubstituted phenyl or substituted or unsubstituted 5- or 6-membered non-aromatic heterocyclic group;

in the circumstance of substituted phenyl, the substituent of phenyl is a radical selected from the group consisting of: —SO$_2$R$_4$, —SO$_2$NHR$_5$; said R$_4$ is C$_1$-C$_3$ alkyl, preferably methyl, R$_5$ is H or C$_1$-C$_3$ alkyl, preferably, H;

said 5- or 6-membered non-aromatic heterocyclic group contains at least one heteroatom selected from N, O or S, and said heterocyclic group can further form a spiroring with another 5 to 6-membered heterocyclic group; and in the circumstance of substituted 5- or 6-membered non-aromatic heterocyclic group, the substituent of 5- or 6-membered non-aromatic heterocyclic group is a radical selected from the group consisting of: oxo, F, Cl, Br, C$_1$-C$_3$ alkyl, —COR$_4$, =NH, —OR$_5$, —CH$_2$Ph, —SO$_2$Ph; said R$_4$ is C$_1$-C$_3$ alkyl, R$_5$ is H or C$_1$-C$_3$ alkyl;

more preferably, R$_3$ is

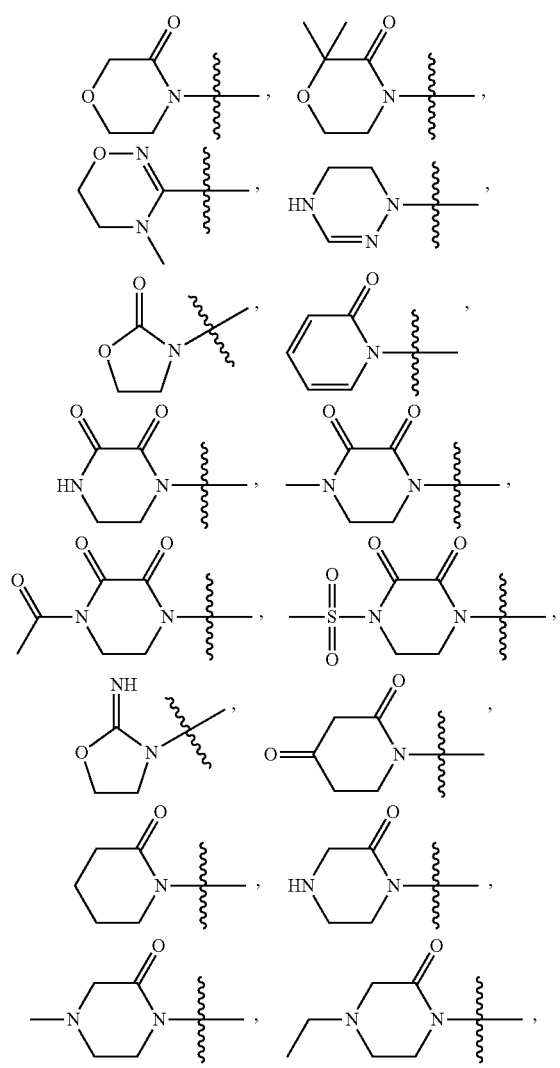

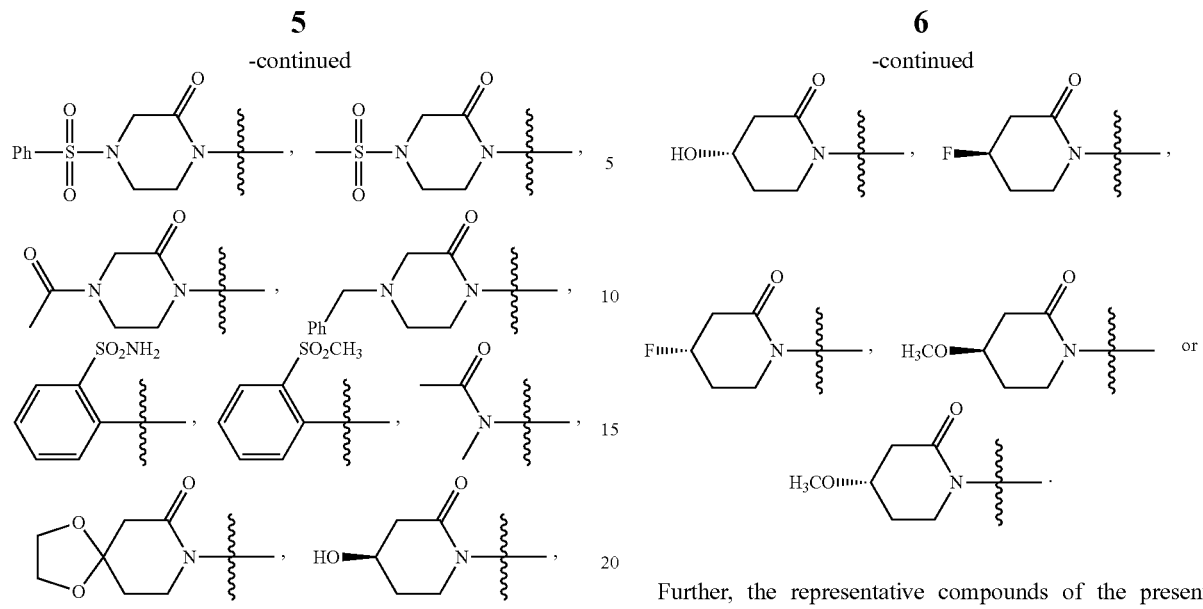
Further, the representative compounds of the present invention are shown in Table 1.
TABLE 1
Representative compounds of the present invention.
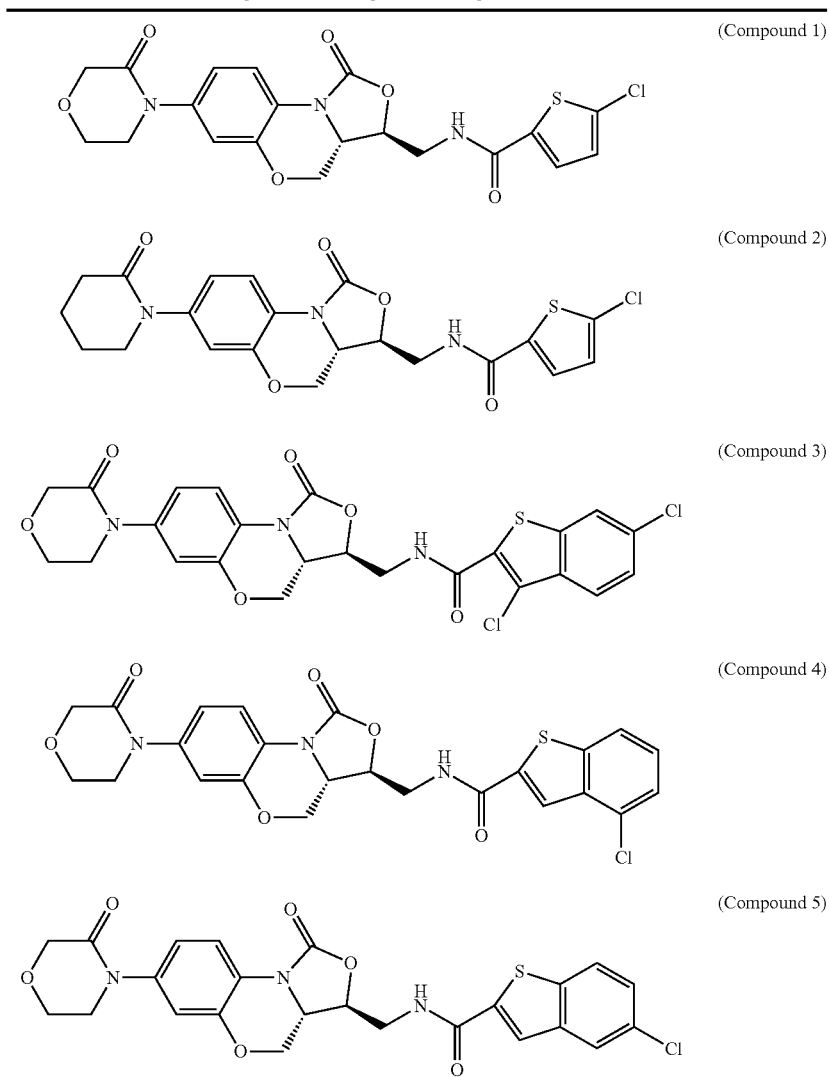

TABLE 1-continued
Representative compounds of the present invention.
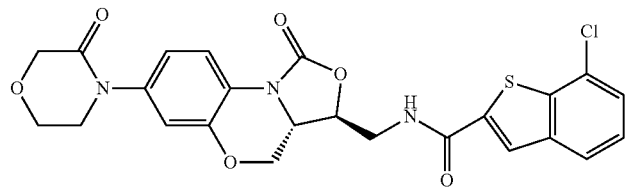 [SMILES: O=C(NC[C@@H]1OC(=O)N2c3ccc(N4CCOCC4=O)cc3OC[C@@H]12)c1cc2cccc(Cl)c2s1] (Compound 6)
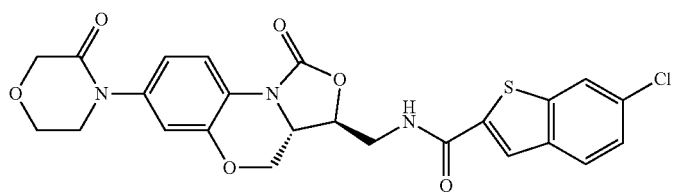 [SMILES: O=C(NC[C@@H]1OC(=O)N2c3ccc(N4CCOCC4=O)cc3OC[C@@H]12)c1cc2ccc(Cl)cc2s1] (Compound 7)
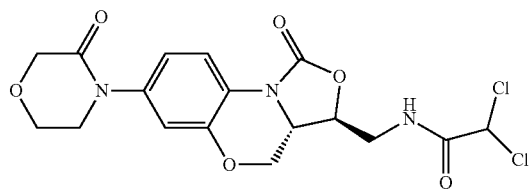 [SMILES: O=C(NC[C@@H]1OC(=O)N2c3ccc(N4CCOCC4=O)cc3OC[C@@H]12)C(Cl)Cl] (Compound 8)
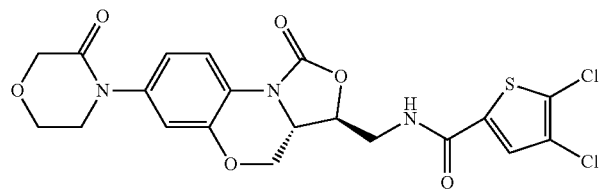 (Compound 9)
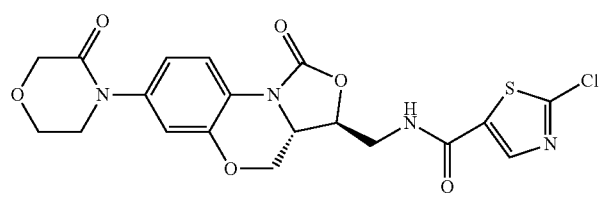 [SMILES: O=C(NC[C@@H]1OC(=O)N2c3ccc(N4CCOCC4=O)cc3OC[C@@H]12)c1cnc(Cl)s1] (Compound 10)
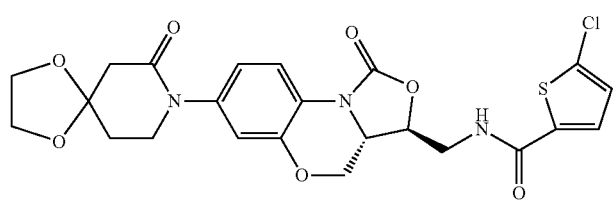 [SMILES: O=C(NC[C@@H]1OC(=O)N2c3ccc(N4CCC5(CC4=O)OCCO5)cc3OC[C@@H]12)c1ccc(Cl)s1] (Compound 11)
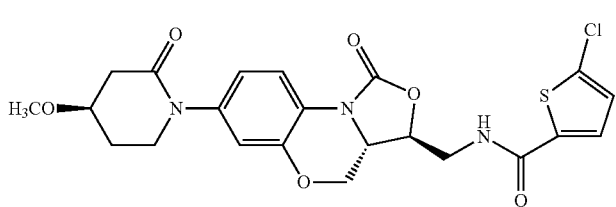 (Compound 12)

TABLE 1-continued
Representative compounds of the present invention.
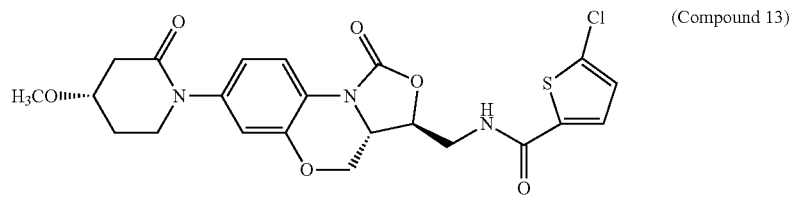
(Compound 13)
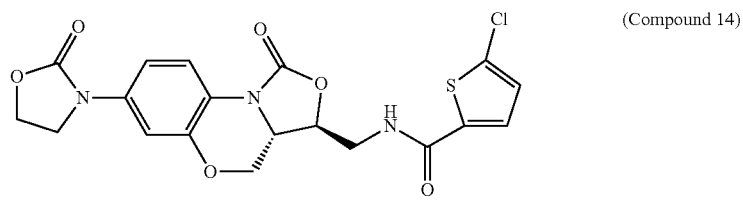
(Compound 14)
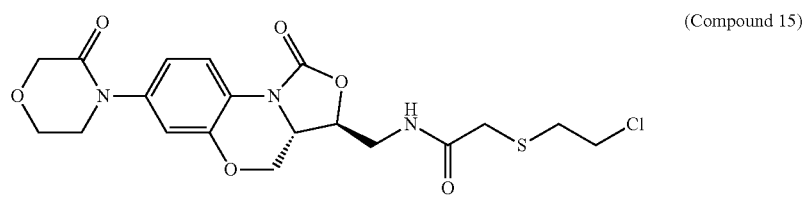
(Compound 15)
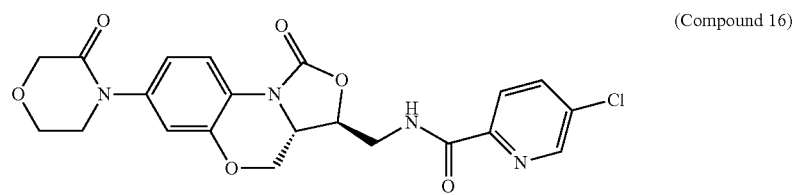
(Compound 16)
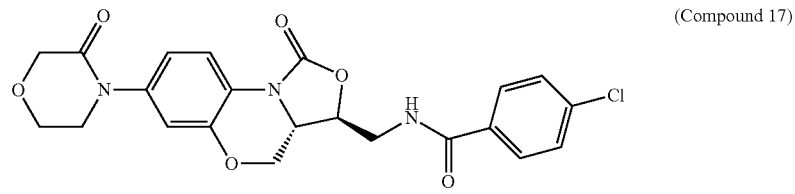
(Compound 17)
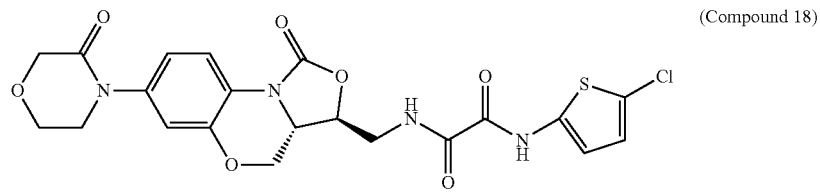
(Compound 18)
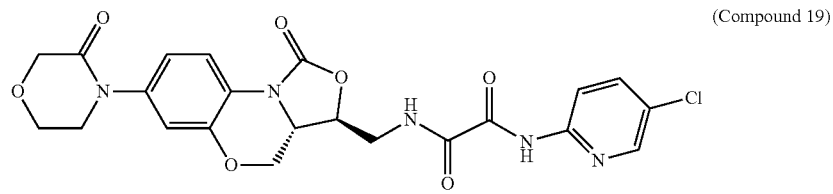
(Compound 19)
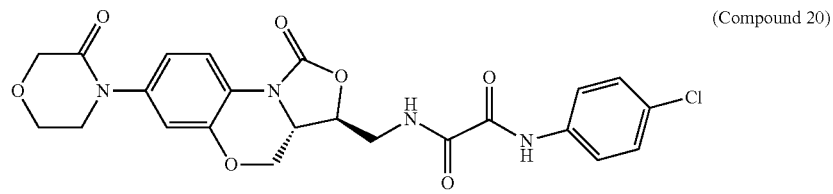
(Compound 20)

TABLE 1-continued
Representative compounds of the present invention.
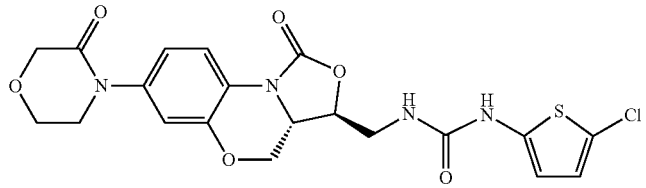 [SMILES: O=C(NC[C@@H]1OC(=O)N2c3ccc(N4CCOCC4=O)cc3OC[C@@H]12)Nc1ccc(Cl)s1]
(Compound 21)
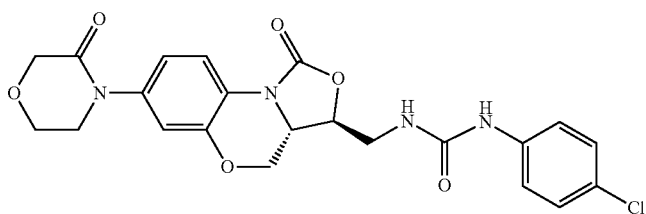 [SMILES: O=C(NC[C@@H]1OC(=O)N2c3ccc(N4CCOCC4=O)cc3OC[C@@H]12)Nc1ccc(Cl)cc1]
(Compound 22)
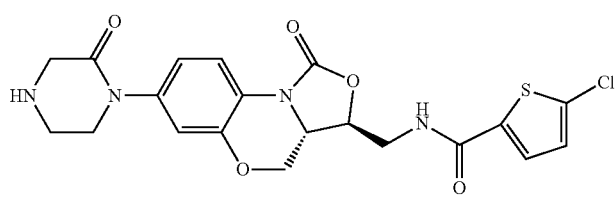 [SMILES: O=C(NC[C@@H]1OC(=O)N2c3ccc(N4CCNCC4=O)cc3OC[C@@H]12)c1ccc(Cl)s1]
(Compound 23)
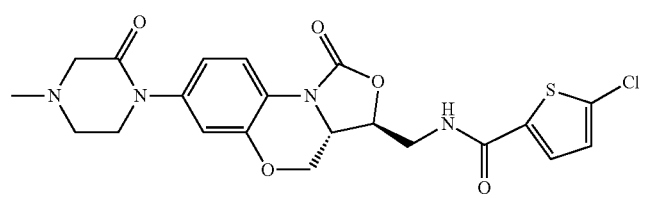 [SMILES: CN1CCN(c2ccc3c(c2)OC[C@H]2[C@H](CNC(=O)c4ccc(Cl)s4)OC(=O)N32)C(=O)C1]
(Compound 24)
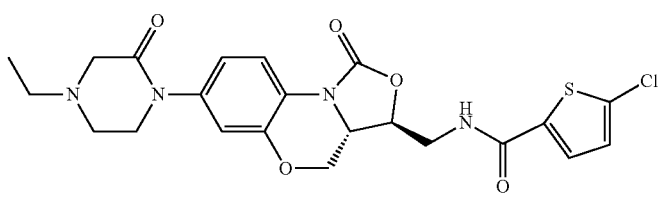 [SMILES: CCN1CCN(c2ccc3c(c2)OC[C@H]2[C@H](CNC(=O)c4ccc(Cl)s4)OC(=O)N32)C(=O)C1]
(Compound 25)
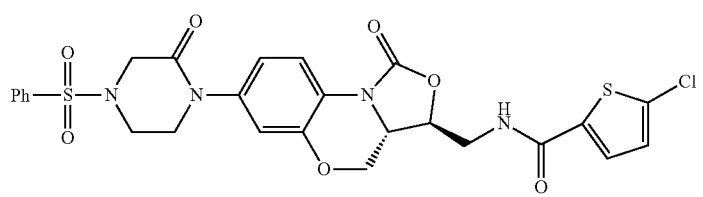 [SMILES: O=C(NC[C@@H]1OC(=O)N2c3ccc(N4CCN(S(=O)(=O)c5ccccc5)CC4=O)cc3OC[C@@H]12)c1ccc(Cl)s1]
(Compound 26)
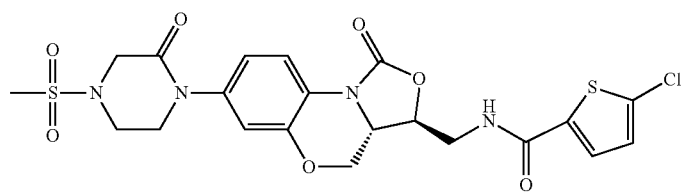 [SMILES: CS(=O)(=O)N1CCN(c2ccc3c(c2)OC[C@H]2[C@H](CNC(=O)c4ccc(Cl)s4)OC(=O)N32)C(=O)C1]
(Compound 27)

TABLE 1-continued
Representative compounds of the present invention.
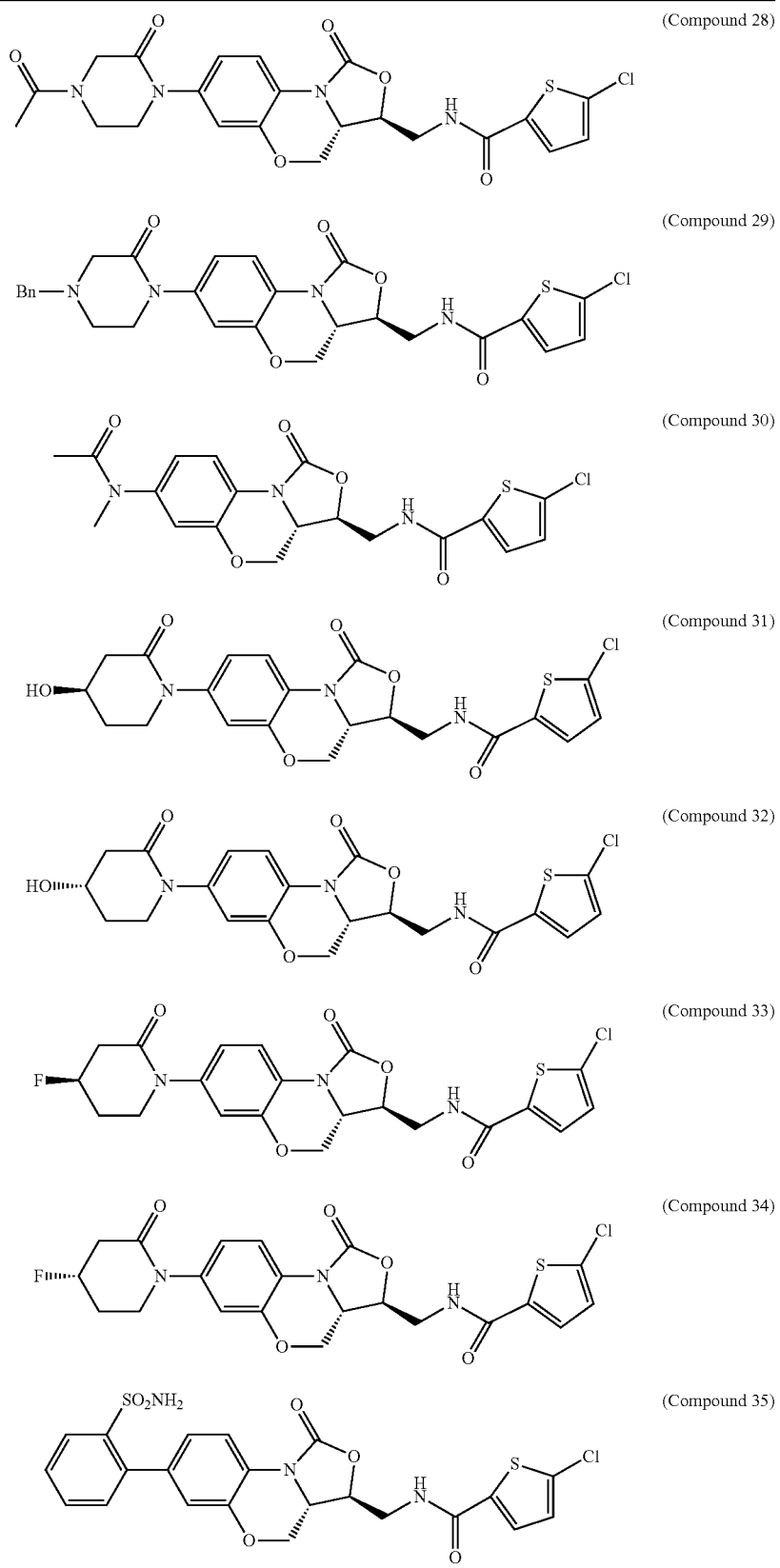
(Compound 28)
(Compound 29)
(Compound 30)
(Compound 31)
(Compound 32)
(Compound 33)
(Compound 34)
(Compound 35)

TABLE 1-continued

Representative compounds of the present invention.

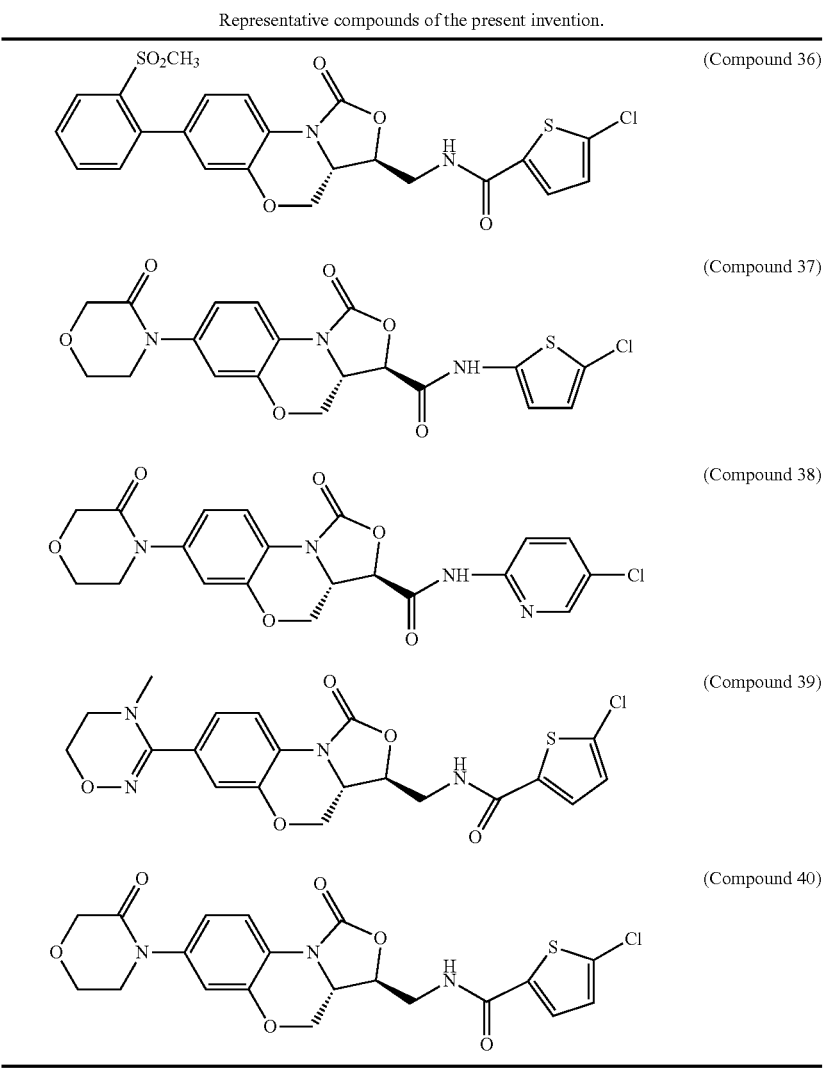

(Compound 36)

(Compound 37)

(Compound 38)

(Compound 39)

(Compound 40)

In the compounds described above, an enantiomer, diastereoisomer and raceme thereof as well as their mixtures, and a pharmaceutically acceptable salt thereof, the configuration of the chiral carbon atom in the compound is R or S.

Another objective of the present invention is to provide a preparation method of the compound of the general formula (I);

The preparation method of the novel oxazolidone compound of the general formula (I) according to the invention will now be described below, although these specific methods do not limit the scope of the invention.

The compounds of the present invention can be prepared according to the following method. However, the conditions of the method, e.g. reactants, solvents, acids, bases, the amount of the compounds used, the reaction temperature, the time needed for the reaction, etc. are not limited to the following illustrations. Optionally, the compounds of the invention can also be conveniently prepared by combining the various synthetic methods described in the present specification or known by those skilled in the art. Such combinations can be readily carried out by those skilled in the art to which the present invention belongs.

Method 1

Route 1

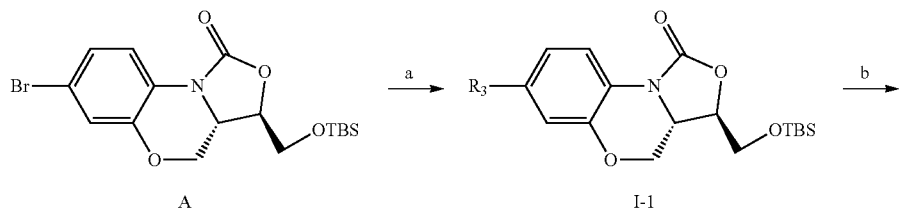

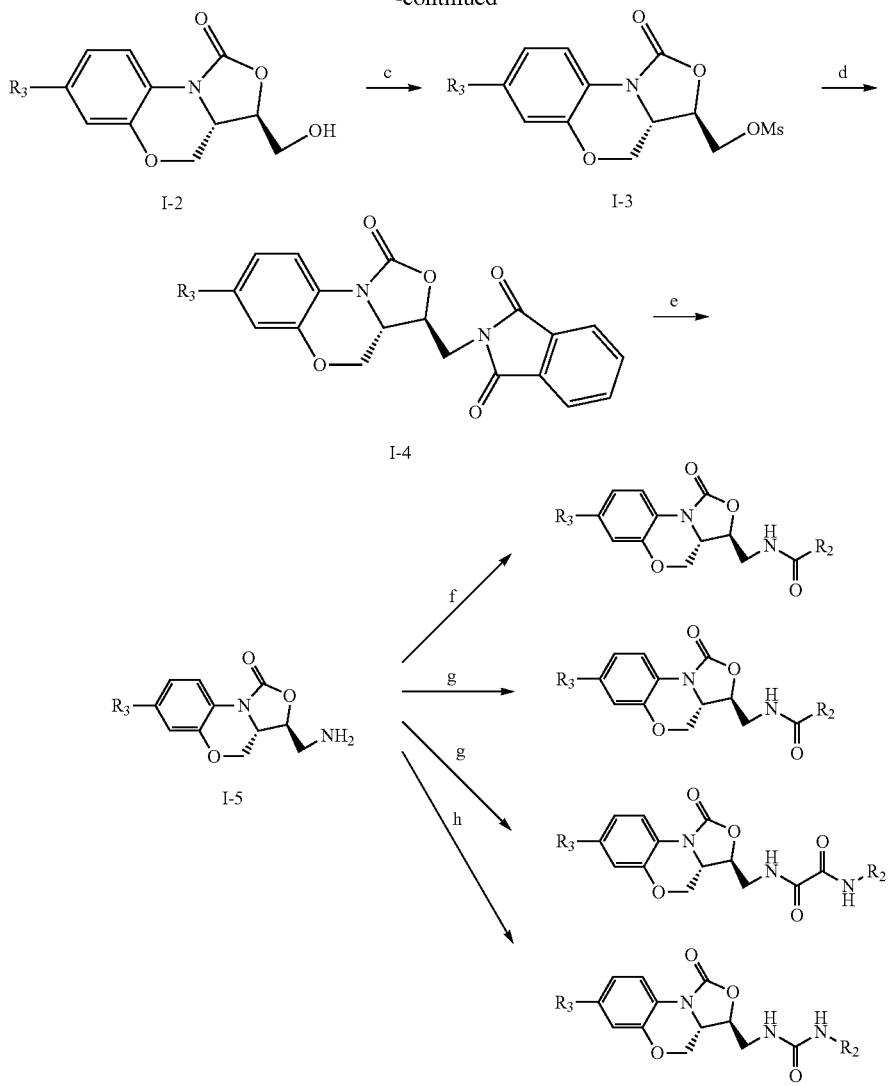

$R_2$, $R_3$ are defined as above.

a, Compound A [Journal of Medicinal Chemistry, 54(21), 7493-7502; 2011] and compound $R_3H$ react, with the catalysation by a palladium-containing catalyst, in the presence of a phosphine-containing ligand, in a polar aprotic solvent under alkaline condition, under the protection of inert gas at a temperature from room temperature to 120° C. for 2-48 hours, to give compound I-1. The palladium-containing catalyst can be palladium acetate [Pd(OAc)$_2$], tris(dibenzylideneacetone)dipalladium (0) [Pd$_2$(dba)$_3$], bis(dibenzylideneacetone)palladium (0) [Pd(dba)$_2$]. The phosphine-containing ligand can be 4,5-bis(diphenylphosphino)-9,9-dimethyl xanthene [Xantphos], (±)-2,2'-bis(diphenylphosphino)-1,1'-binaphthalene [BINAP] or 1,1'-bis(diphenylphosphino) ferrocene [dppf]. The alkali used for said alkaline condition can be: cesium carbonate (Cs$_2$CO$_3$), sodium tert-butoxide (NaO$^t$Bu), potassium phosphate (K$_3$PO$_4$), potassium carbonate (K$_2$CO$_3$). The polar aprotic solvent can be: 1,4-dioxane, toluene, dimethylformamide (DMF). The inert gas can be nitrogen or argon.

b, Compound I-1 reacts, in the presence of a fluorine-containing reagent, in a polar aprotic solvent, at room temperature for 1-3 hours, to remove the protecting group t-butyldimethylsilyl (TBS), thereby giving compound I-2. The fluorine-containing reagent can be tetrabutylammonium fluoride ("Bu$_4$NF). The polar aprotic solvent is tetrahydrofuran or dimethoxyethane.

c, Compound I-2 and methylsulfonyl chloride (MsCl) react, in the presence of an organic base, in a polar aprotic solvent, at a temperature from –10° C. to room temperature for 1-3 hours, to give the corresponding compound I-3. The organic base can be triethylamine or pyridine. The polar aprotic solvent can be tetrahydrofuran or dichloromethane.

d, Compound I-3 and phthalimide potassium react, in a polar aprotic solvent, at a temperature from room temperature to 100° C. for 1-24 hours, to give the corresponding compound I-4. The polar aprotic solvent can be: N,N-dimethylformamide, acetonitrile.

e, Compound I-4 and methylamine alcohol solution react in a polar solvent at a temperature from room temperature to 80° C. for 1-12 hours, to give the corresponding compound I-5. The polar solvent is: methanol or ethanol.

f, Compound I-5 and $R_2$ substituted acyl chloride, in the presence of an organic base, in a polar aprotic solvent, at a temperature from –10° C. to room temperature for 1-3 hours, to give the corresponding compound. The organic base can be triethylamine or pyridine. The polar aprotic solvent can be tetrahydrofuran or dichloromethane.

g, Compound I-5 and R₂ substituted carboxylic acid or amino oxalic acid substituted with R₂ at its N position react, in the presence of a condensation agent and an organic base, h, Compound I-5 and R₂ substituted isocyanate react, in a solvent at a temperature from room temperature to 110° C. for 3-24 hours, to give the corresponding compound. The solvent can be toluene or dichloromethane.

Route 2 compounds 23-29 are prepared according to Scheme II.

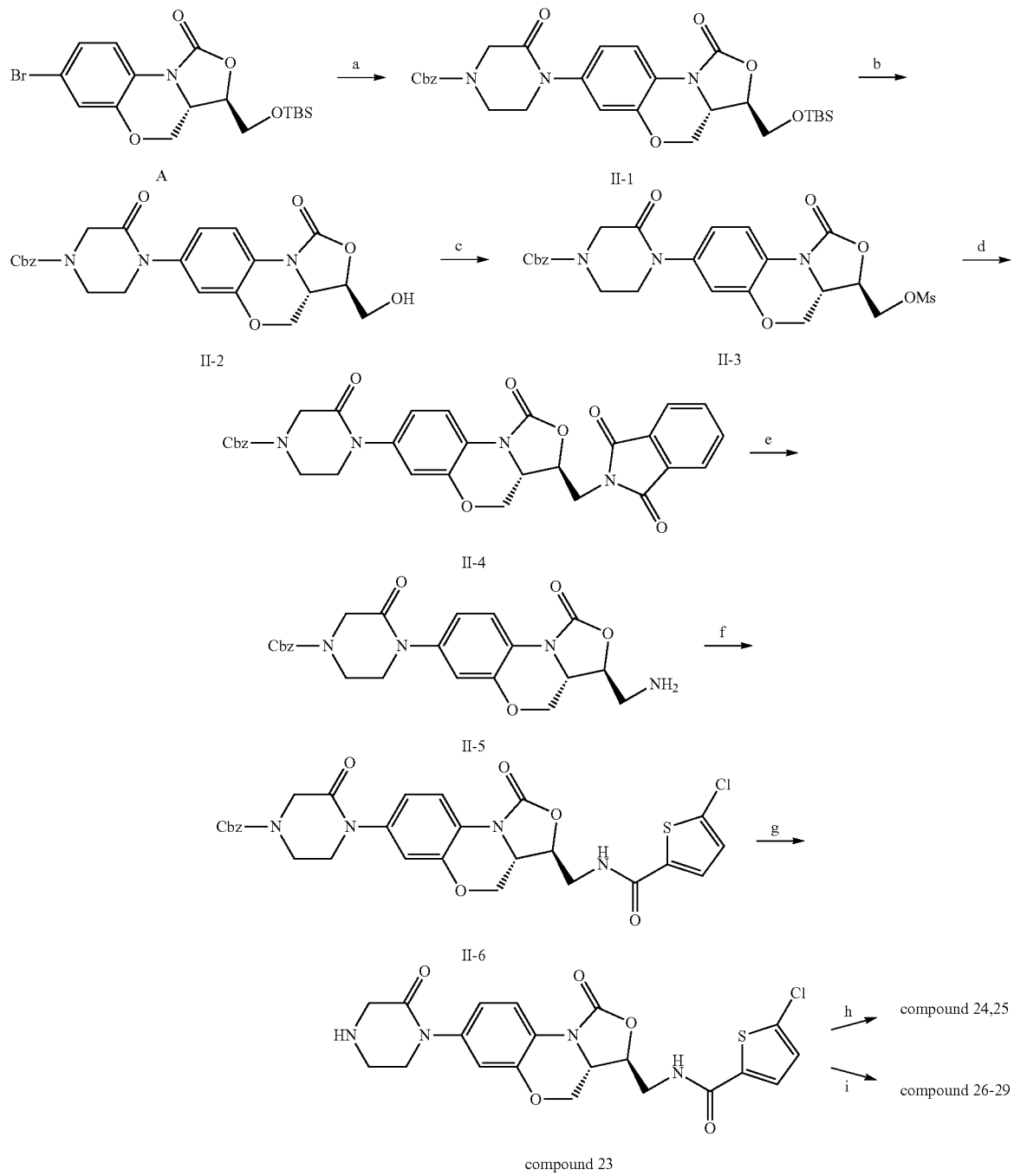

in a polar solvent, at room temperature for 1-6 hours, to give the corresponding compound. The condensation agent can be 2-(7-azabenzotriazol)-N,N,N',N'-tetramethyluronium hexafluorophosphate (HATU), 1-hydroxybenzotriazole (HOBT). The organic base can be triethylamine, diisopropylethylamine. The polar solvent can be dichloromethane.

a, Compound A and compound benzyl 3-oxopiperazin-1-carboxylate react, with the catalysation by a palladium-containing catalyst, in the presence of a phosphine-containing ligand, in a polar aprotic solvent under alkaline condition, under the protection of inert gas at a temperature from room temperature to 120° C. for 2-48 hours, to give compound II-1.

The palladium-containing catalyst can be palladium acetate, tris(dibenzylideneacetone)dipalladium (0), bis(dibenzylideneacetone)palladium (0). The phosphine-containing ligand can be 4,5-bis(diphenylphosphino)-9,9-dimethyl xanthene (±)-2,2'-bis(diphenylphosphino)-1,1'-binaphthalene or 1,1'-bis(diphenylphosphino) ferrocene. The alkali used for said alkaline condition can be: cesium carbonate, sodium tert-butoxide, potassium phosphate, potassium carbonate. The polar aprotic solvent can be: 1,4-dioxane, toluene, dimethylformamide. The inert gas can be nitrogen or argon.

b, Compound II-1 reacts, in the presence of a fluorine-containing reagent, in a polar aprotic solvent, at room temperature for 1-3 hours, to remove the protecting group t-butyldimethylsilyl, thereby giving compound II-2. The fluorine-containing reagent can be tetrabutylammonium fluoride. The polar aprotic solvent is tetrahydrofuran or dimethoxyethane.

c, Compound II-2 and methylsulfonyl chloride react, in the presence of an organic base, in a polar aprotic solvent, at a temperature from −10° C. to room temperature for 1-3 hours, to give the corresponding compound II-3. The organic base can be triethylamine or pyridine. The polar aprotic solvent can be tetrahydrofuran or dichloromethane.

d, Compound II-3 and phthalimide potassium react, in a polar aprotic solvent, at a temperature from room temperature to 100° C. for 1-24 hours, to give the corresponding compound II-4. The polar aprotic solvent can be: N,N-dimethylformamide, acetonitrile.

e, Compound II-4 and methylamine alcohol solution react in a polar solvent at a temperature from room temperature to 80° C. for 1-12 hours, to give the corresponding compound II-5. The polar solvent is: methanol or ethanol.

f, Compound II-5 and 2-chlorothiophene-5-formyl chloride react, in the presence of an organic base, in a polar aprotic solvent, at a temperature from −10° C. to room temperature for 1-3 hours, to give compound II-6. The organic base can be triethylamine or pyridine. The polar aprotic solvent can be tetrahydrofuran or dichloromethane.

g, Compound II-6 reacts with a deprotecting agent, in a polar aprotic solvent, at a temperature from −10° C. to room temperature for 1-6 hours, to give compound 23. The deprotecting agent is dimethyl sulfide and boron trifluoride etherate solution. The polar aprotic solvent is dichloromethane.

h, Compound 23 and an aldehyde react, in the presence of a reducing agent, in a polar protic solvent, at a temperature from 0° C. to room temperature for 3-10 h, to give compounds 24, 25. The polar protic solvent is methanol. The reducing agent can be sodium triacetoxyborohydride or sodium cyanoborohydride.

i, Compound 23 reacts with sulfonyl chloride, alkyl acyl chloride, and benzyl bromide, in the presence of an organic base, in a polar aprotic solvent, at a temperature from −10° C. to room temperature for 1-3 hours, to give the corresponding compounds 26-29. The organic base can be triethylamine or diisopropylethylamine. The polar aprotic solvent can be tetrahydrofuran or dichloromethane.

Route 3

Compound 30 is prepared according to Scheme III.

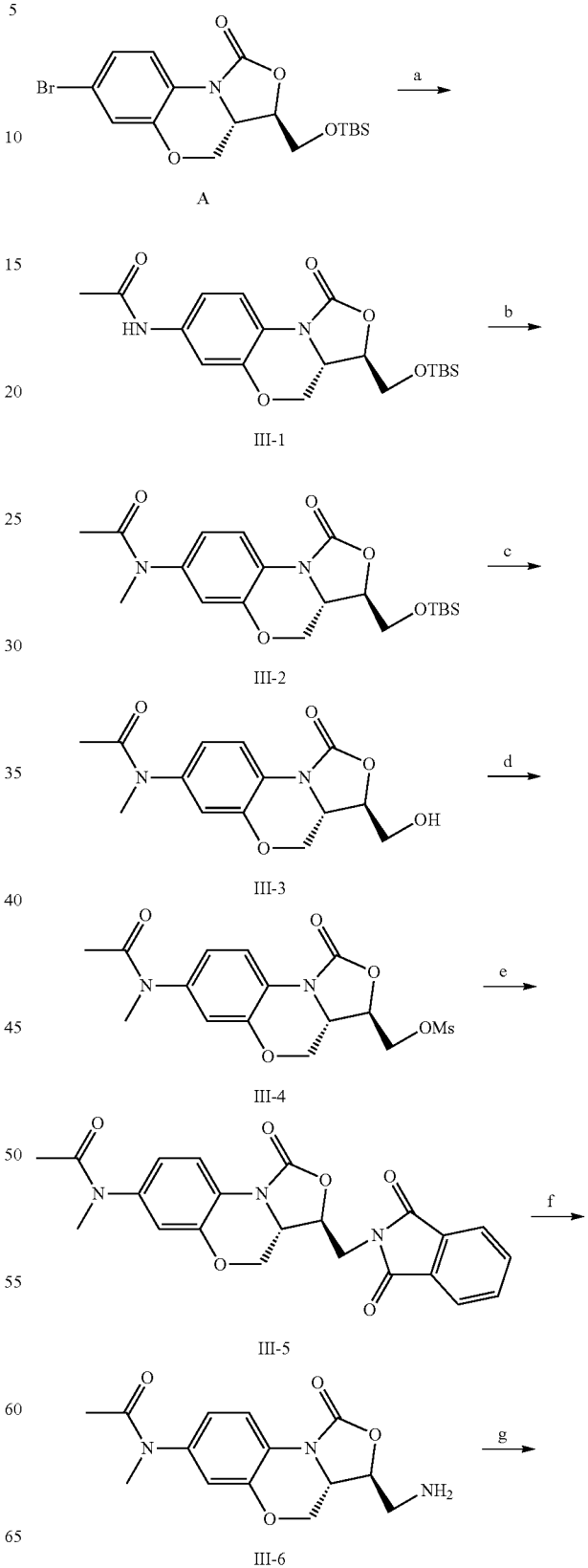

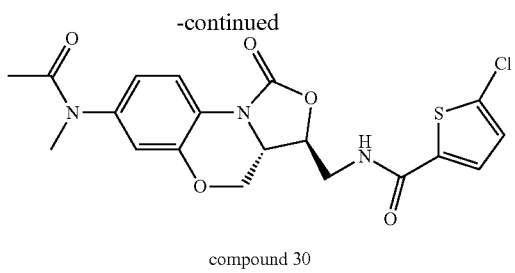

compound 30 a, Compound A and compound acetamide react, with the catalysation by a palladium-containing catalyst, in the presence of a phosphine-containing ligand, in a polar aprotic solvent under alkaline condition, under the protection of inert gas at a temperature from room temperature to 120° C. for 2-48 hours, to give compound III-1. The palladium-containing catalyst can be palladium acetate, tris(dibenzylideneacetone)dipalladium (0), bis(dibenzylideneacetone)palladium (0). The phosphine-containing ligand can be 4,5-bis(diphenylphosphino)-9,9-dimethyl xanthene (±)-2,2'-bis(diphenylphosphino)-1,1'-binaphthalene or 1,1'-bis(diphenylphosphino) ferrocene. The alkali used for said alkaline condition can be: cesium carbonate, sodium tert-butoxide, potassium phosphate, potassium carbonate. The polar aprotic solvent can be: 1,4-dioxane, toluene, dimethylformamide. The inert gas can be nitrogen or argon.

b, Compound III-1 reacts with a methylating agent in a polar aprotic solvent under alkaline condition and cooling on a ice-salt bath for 1-6 hours, to give compound III-2. The methylating agent can be iodomethane or dimethyl sulfate; said alkali can be sodium hydride, potassium tert-butoxide or sodium tert-butoxide. The polar aprotic solvent can be tetrahydrofuran or N,N-dimethylformamide.

c, Compound III-2 reacts, in the presence of a fluorine-containing reagent, in a polar aprotic solvent, at room temperature for 1-3 hours, to remove the protecting group t-butyldimethylsilyl, thereby giving compound III-3. The fluorine-containing reagent can be tetrabutylammonium fluoride. The polar aprotic solvent is tetrahydrofuran or dichloromethane.

d, Compound III-3 and methylsulfonyl chloride react, in the presence of an organic base, in a polar aprotic solvent, at a temperature from −10° C. to room temperature for 1-3 hours to give the corresponding compound III-4. The organic base can be triethylamine or pyridine. The polar aprotic solvent can be tetrahydrofuran or dichloromethane.

e, Compound III-4 and phthalimide potassium react, in a polar aprotic solvent, at a temperature from room temperature to 100° C. for 1-24 hours, to give the corresponding compound III-5. The polar aprotic solvent can be: N,N-dimethylformamide or acetonitrile.

f, Compound III-5 and methylamine alcohol solution react in a polar solvent at a temperature from room temperature to 80° C. for 1-12 hours, to give the corresponding compound III-6. The polar solvent is: methanol or ethanol.

g, Compound III-6 and 2-chlorothiophene-5-formyl chloride react, in the presence of an organic base, in a polar aprotic solvent, at a temperature from −10° C. to room temperature for 1-3 hours, to give compound 30. The organic base can be triethylamine or pyridine. The polar aprotic solvent can be tetrahydrofuran or dichloromethane.

Route 4

Compounds 31-34 are prepared according to Scheme IV.

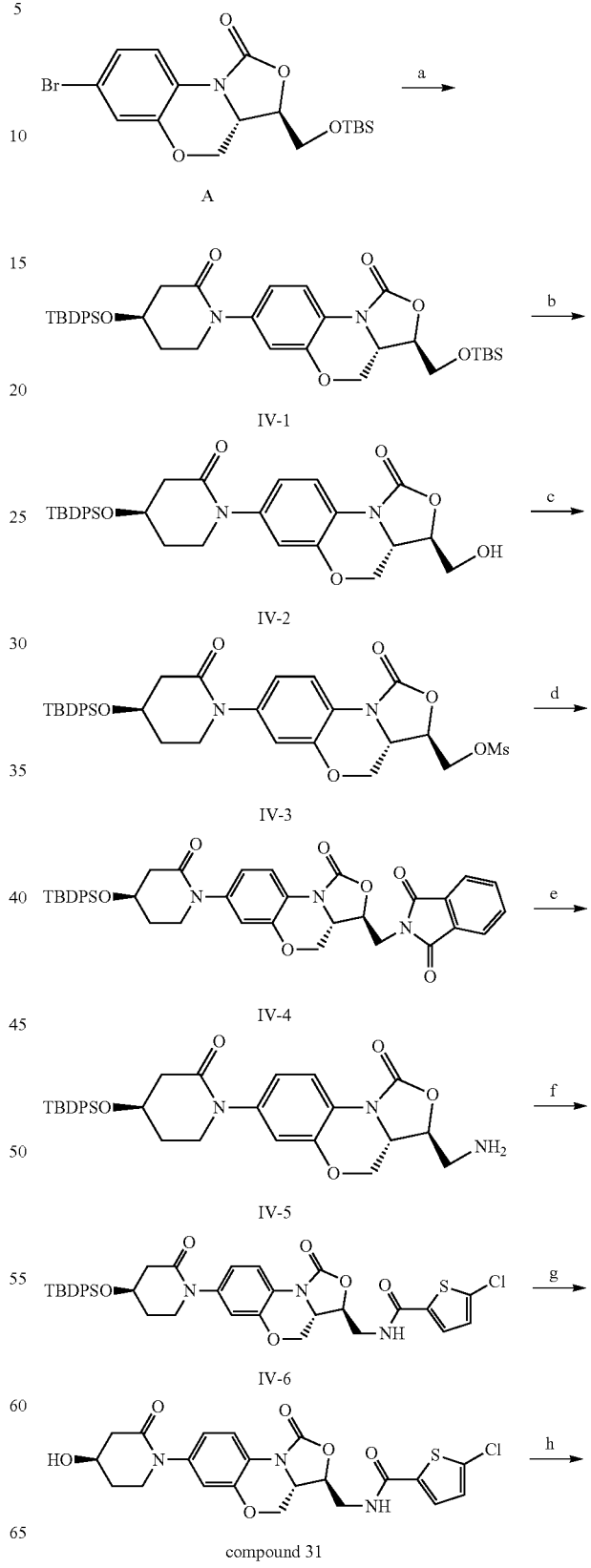

compound 31

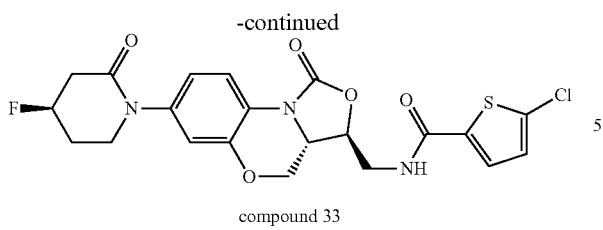

compound 33 a, Compound A and (±) 4-(t-butyldiphenylsiloxy) piperidin-2-one react, with the catalysation by a palladium-containing catalyst, in the presence of a phosphine-containing ligand, in a polar aprotic solvent under alkaline condition, under the protection of inert gas at a temperature from room temperature to 120° C. for 2-48 hours, to give compound IV-1 upon column chromatography. The palladium-containing catalyst can be palladium acetate, tris(dibenzylideneacetone)dipalladium (0), bis(dibenzylideneacetone)palladium (0). The phosphine-containing ligand can be 4,5-bis(diphenylphosphino)-9,9-dimethyl xanthene, (±)-2,2'-bis(diphenylphosphino)-1,1'-binaphthalene or 1,1'-bis(diphenylphosphino) ferrocene. The alkali used for said alkaline condition can be: cesium carbonate, sodium tert-butoxide, potassium phosphate, potassium carbonate. The polar aprotic solvent can be: 1,4-dioxane, toluene, dimethylformamide. The inert gas can be nitrogen or argon.

b, Compound IV-1 reacts with a selective deprotecting agent in a polar aprotic solvent at a temperature from 0° C. to room temperature for 24-48 hours, to give compound IV-2. The selective deprotecting agent is a solution of boron trichloride in dichloromethane. The polar aprotic solvent is tetrahydrofuran.

c, Compound IV-2 and methylsulfonyl chloride react in the presence of an organic base, in a polar aprotic solvent, at a temperature from −10° C. to room temperature for 1-3 hours, to give the corresponding compound IV-3. The organic base can be triethylamine or pyridine. The polar aprotic solvent can be tetrahydrofuran or dichloromethane.

d, Compound IV-3 and phthalimide potassium react, in a polar aprotic solvent, at a temperature from room temperature to 100° C. for 1-24 hours, to give the corresponding compound IV-4. The polar aprotic solvent can be: N,N-dimethylformamide, acetonitrile.

e, Compound IV-4 and methylamine alcohol solution react in a polar solvent at a temperature from room temperature to 80° C. for 1-12 hours to give the corresponding compound IV-5. The polar solvent is: methanol or ethanol.

f, Compound IV-5 and 2-chlorothiophene-5-formyl chloride react, in the presence of an organic base, in a polar aprotic solvent, at a temperature from −10° C. to room temperature for 1-3 hours, to give compound IV-6. The organic base can be triethylamine or pyridine. The polar aprotic solvent can be tetrahydrofuran or dichloromethane.

g, Compound IV-6 reacts, in the presence of a fluorine-containing reagent, in a polar aprotic solvent, at room temperature for 1-3 hours, to remove the protecting group t-butyldiphenylsilyl, thereby giving compound 31. The fluorine-containing reagent can be tetrabutylammonium fluoride. The polar aprotic solvent is tetrahydrofuran or dichloromethane.

h, Compound 31 reacts with a fluorinating agent in a polar aprotic solvent under the protection of inert gas at a temperature from −10° C. to room temperature for 1-3 hours, to give compound 33. The fluorinating agent is diethylaminosulphur trifluoride (DAST); the polar aprotic solvent can be tetrahydrofuran or dichloromethane; the inert gas can be nitrogen or argon.

* The preparation method of compound 32 is the same with that of compound 31; the preparation method of compound 34 is the same with that of compound 33.

Method 2
Route 5

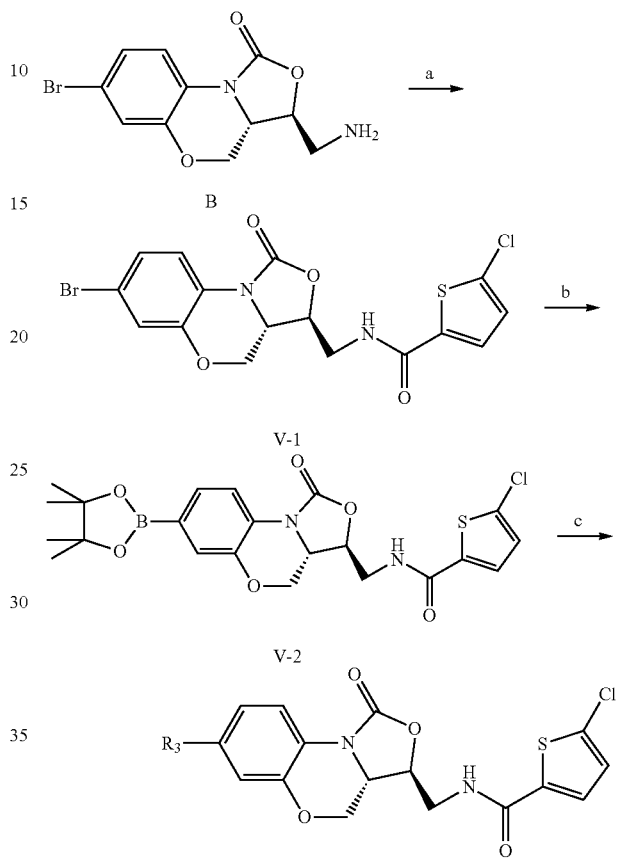

$R_3$ is defined as above.

a, Compound B [Journal of Medicinal Chemistry, 54(21), 7493-7502; 2011] and 2-chlorothiophene-5-formyl chloride react, in the presence of an organic base, in a polar aprotic solvent, at a temperature from −10° C. to room temperature for 1-3 hours, to give compound V-1. The organic base is triethylamine or pyridine. The polar aprotic solvent can be tetrahydrofuran or dichloromethane.

b, Compound V-1 and bis(pinacolato)diboron react, with the catalysation by a palladium-containing catalyst, in the presence of a phosphine-containing ligand, in a polar solvent under alkaline condition, under the protection of inert gas at a temperature from room temperature to 110° C. for 0.5-48 hours, to give compound V-2; the palladium-containing catalyst is $Pd(PPh_3)_4$, $Pd(dppf)Cl_2$, $Pd(dppf)Cl_2.CH_2Cl_2$, or $Pd(dba)_2$; the phosphine-containing ligand is 2-(di-tert-butylphosphino)biphenyl; the alkali used for said alkaline condition is: potassium acetate, sodium acetate, potassium tert-butoxide or sodium tert-butoxide; the polar solvent is dimethyl sulfoxide, N,N-dimethylformamide, 1,4-dioxane, tetrahydrofuran or toluene; the inert gas is nitrogen or argon.

c, Compound V-2 and the bromide $R_3Br$ react, with the catalysation by a palladium-containing catalyst, in a polar solvent under alkaline condition, under the protection of inert gas at a temperature from room temperature to 120° C. for 2-24 hours, to give the corresponding compounds 35 and 36;

The palladium-containing catalyst is Pd(PPh₃)₄, Pd(dppf)Cl₂, or Pd(dppf)Cl₂.CH₂Cl₂; the alkali used for said alkaline condition is: cesium carbonate, potassium carbonate or potassium fluoride; the polar solvent is: 1,4-dioxane, tetrahydrofuran, water, ethylene glycol dimethyl ether, ethanol, N,N-dimethylformamide or toluene, or a mixture thereof; the inert gas is nitrogen or argon.

Method 3
Route 6

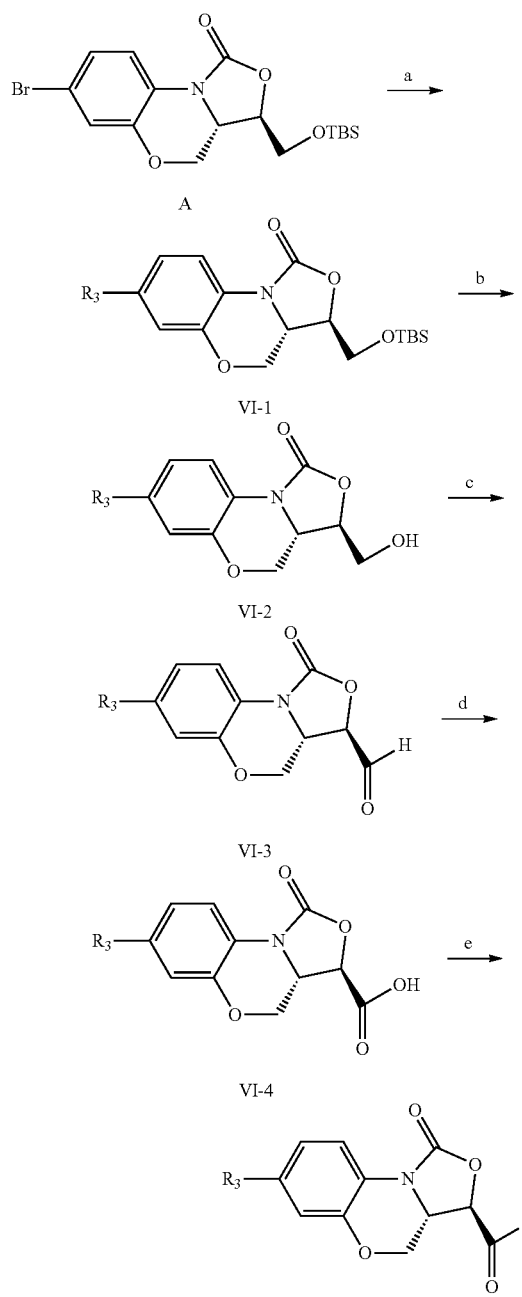

R₂ and R₃ are defined as above.

a, Compound A and compound R₃H react, with the catalysation by a palladium-containing catalyst, in the presence of a phosphine-containing ligand, in a polar aprotic solvent under alkaline condition, under the protection of inert gas at a temperature from room temperature to 120° C. for 2-48 hours, to give compound VI-1. The palladium-containing catalyst can be palladium acetate, tris(dibenzylideneacetone)dipalladium (0), bis(dibenzylideneacetone)palladium (0). The phosphine-containing ligand can be 4,5-bis(diphenylphosphino)-9,9-dimethyl xanthene (±)-2,2'-bis(diphenylphosphino)-1,1'-binaphthalene or 1,1'-bis(diphenylphosphino) ferrocene. The alkali used for said alkaline condition can be: cesium carbonate, sodium tert-butoxide, potassium phosphate, potassium carbonate. The polar aprotic solvent can be: 1,4-dioxane, toluene, N,N-dimethylformamide; the inert gas can be nitrogen or argon.

b, Compound VI-1 reacts, in the presence of a fluorine-containing reagent, in a polar aprotic solvent, at room temperature for 1-3 hours, to remove the protecting group t-butyldimethylsilyl, thereby giving compound VI-2. The fluorine-containing reagent can be tetrabutylammonium fluoride. The polar aprotic solvent is tetrahydrofuran or dimethoxyethane.

c, Compound VI-2 reacts with an oxidizing agent in a polar aprotic solvent at a temperature from 0° C. to room temperature for 1-6 hours, to give the corresponding compound VI-3. The oxidizing agent is (1,1,1-triacetyloxy)-1,1-dihydro-1,2-benziodoxol-3(1H)-one (DMP); the polar solvent can be dichloromethane or dimethyl sulfoxide.

d, Compound VI-3 reacts with an oxidizing agent in a polar aprotic solvent and a buffer solution at room temperature for 1-24 hours to give the corresponding compound VI-4. The polar aprotic solvent can be dichloromethane or dimethyl sulfoxide; the buffer solution is sodium dihydrogen phosphate buffer solution; the oxidizing agent can be sodium hypochlorite, hydrogen peroxide or a mixture thereof.

e, Compound VI-4 and a R₂ substituted amine react, in the presence of a condensation agent and an organic base, in a polar aprotic solvent, at room temperature for 1-6 hours, to give the corresponding compounds 37 and 38. The condensation agent can be HATU, HOBT. The organic base can be triethylamine, diisopropylethylamine. The polar aprotic solvent can be dichloromethane.

Method 4
Route 7

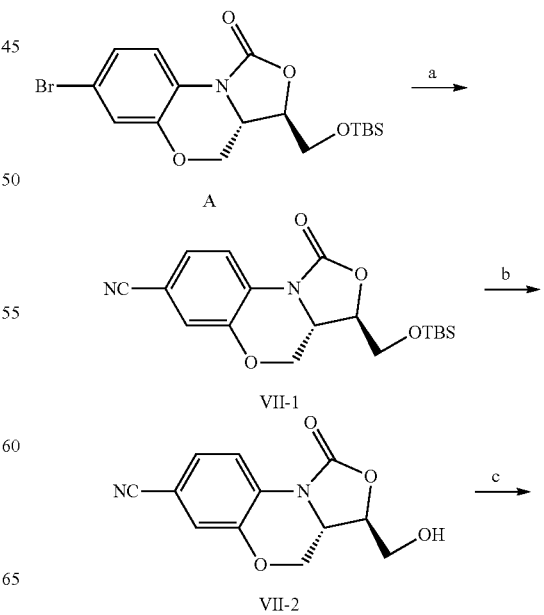

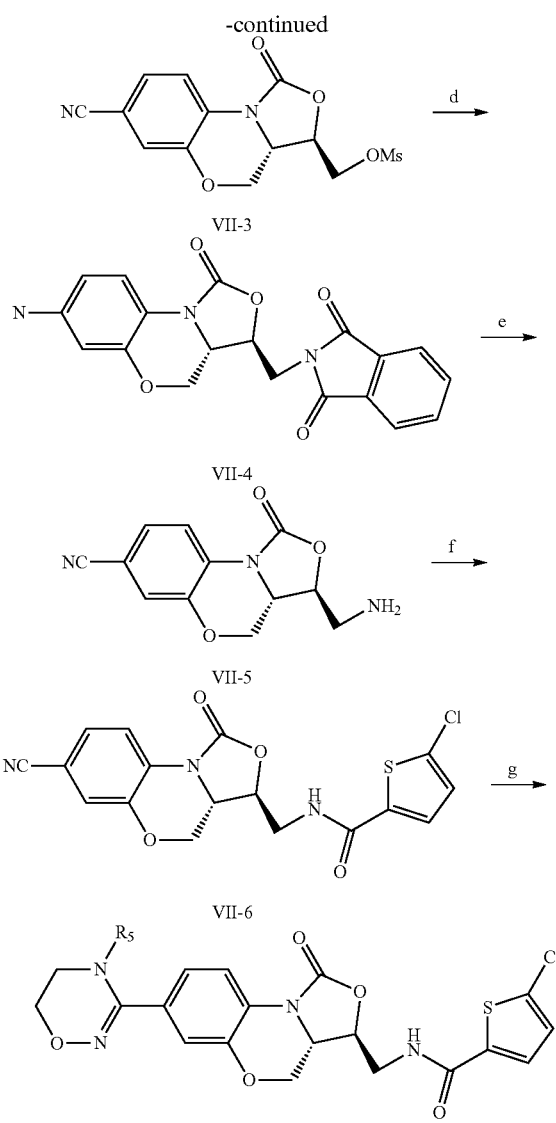

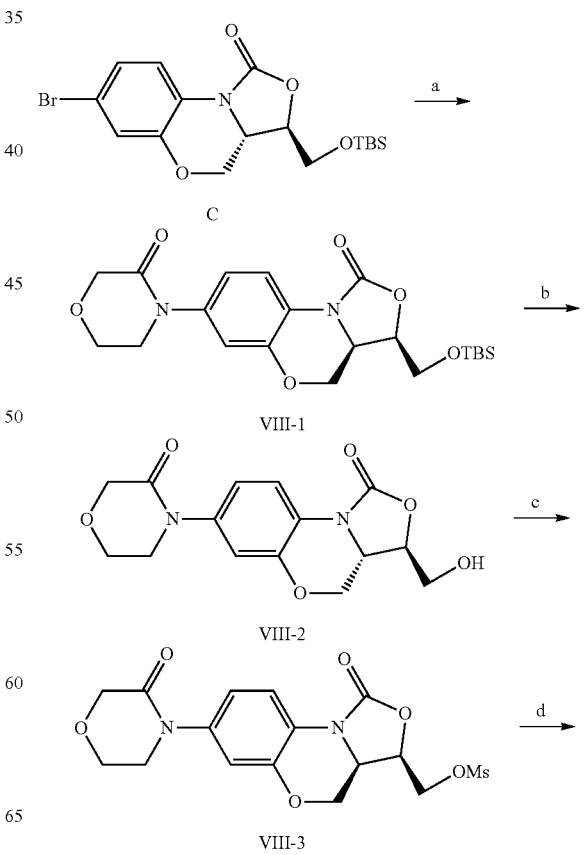

c, Compound VII-2 and methylsulfonyl chloride (MsCl) react, in the presence of an organic base, in a polar aprotic solvent, at a temperature from −10° C. to room temperature for 1-3 hours, to give the corresponding compound VII-3. The organic base can be triethylamine or pyridine. The polar aprotic solvent can be tetrahydrofuran or dichloromethane.

d, Compound VII-3 and phthalimide potassium react, in a polar aprotic solvent, at a temperature from room temperature to 100° C. for 1-24 hours, to give the corresponding compound VII-4. The polar aprotic solvent can be: N,N-dimethylformamide, acetonitrile.

e, Compound VII-4 and methylamine alcohol solution react in a polar solvent at a temperature from room temperature to 80° C. for 1-12 hours, to give the corresponding compound VII-5. The polar solvent is: methanol or ethanol.

f, Compound VII-5 and a $R_2$ substituted acyl chloride react, in the presence of an organic base, in a polar aprotic solvent, at a temperature from −10° C. to room temperature for 1-3 hours, to give the corresponding compound VII-6. The organic base can be triethylamine or pyridine. The polar aprotic solvent can be tetrahydrofuran or dichloromethane.

g, Compound VII-6 in an alcohol solvent was bubbled with hydrogen chloride gas at 0° C. for 2-6 h, and then stirred at room temperature for 2-6 h. After compound VII-6 reacts completely, the solvent and the residual acid are removed by evaporation. The resulting mixture and 2-aminooxy-N—R5-ethylamine react under reflux in a polar protic solvent for 10-24 h, to give the corresponding compound 39. The alcohol solvent can be methanol, ethanol; the polar protic solvent can be methanol, ethanol, acetic acid.

Method 5
Route 8

$R_5$ is defined as above.

a, Compound A [Journal of Medicinal Chemistry, 54(21), 7493-7502; 2011] and compound potassium ferrocyanide(II) trihydrate [KFe(CN)$_6$.3H$_2$O] react, with the catalysation by a palladium-containing catalyst, in a polar aprotic solvent under alkaline condition, under the protection of inert gas at a temperature from room temperature to 150° C. for 0.5-12 hours, to give compound VII-1. The palladium-containing catalyst can be palladium acetate [Pd(OAc)$_2$]. The alkali used for said alkaline condition can be: cesium carbonate (Cs$_2$CO$_3$), sodium tert-butoxide (NaO$^t$Bu), potassium phosphate (K$_3$PO$_4$), potassium carbonate (K$_2$CO$_3$), sodium carbonate (Na$_2$CO$_3$). The polar aprotic solvent can be: N-methylpyrrolidone (NMP), 1,4-dioxane, toluene, dimethylformamide (DMF). The inert gas can be nitrogen or argon.

b, Compound VII-1 reacts, in the presence of a fluorine-containing reagent, in a polar aprotic solvent, at room temperature for 1-3 hours, to remove the protecting group t-butyldimethylsilyl (TBS), thereby giving compound VII-2. The fluorine-containing reagent can be tetrabutylammonium fluoride ($^n$Bu$_4$NF). The polar aprotic solvent is tetrahydrofuran or dimethoxyethane.

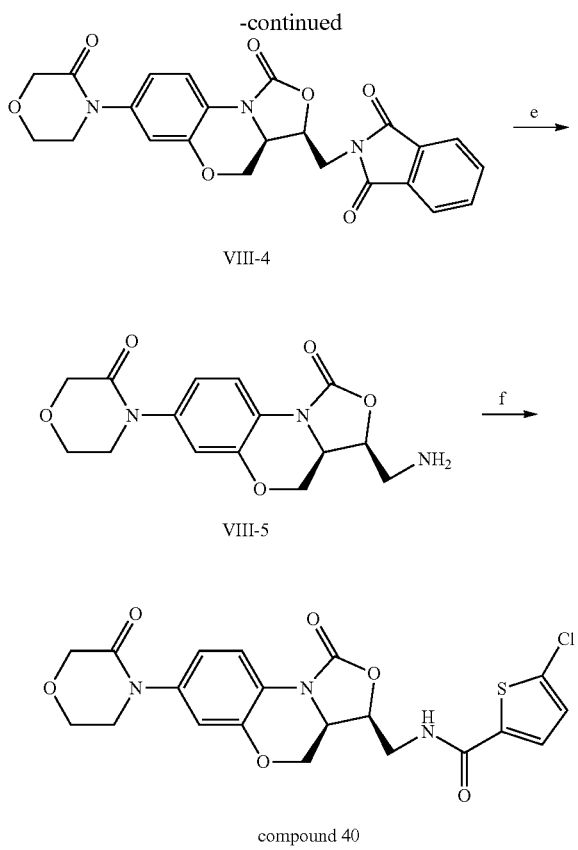

VIII-4

VIII-5 compound 40 a, Compound A [Journal of Medicinal Chemistry, 54(21), 7493-7502; 2011] and morpholone react, with the catalysation by a palladium-containing catalyst, in the presence of a phosphine-containing ligand, in a polar aprotic solvent under alkaline condition, under the protection of inert gas at a temperature from room temperature to 120° C. for 2-48 hours, to give compound VIII-1. The palladium-containing catalyst can be palladium acetate [Pd(OAc)$_2$], tris(dibenzylideneacetone)dipalladium (0)[Pd$_2$(dba)$_3$], bis(dibenzylideneacetone)palladium (0) [Pd(dba)$_2$]. The phosphine-containing ligand can be 4,5-bis(diphenylphosphino)-9,9-dimethyl xanthene [Xantphos], (±)-2,2'-bis(diphenylphosphino)-1,1'-binaphthalene [BINAP] or 1,1'-bis(diphenylphosphino) ferrocene [dppf]. The alkali used for said alkaline condition can be: cesium carbonate (Cs$_2$CO$_3$), sodium tert-butoxide (NaO$^t$Bu), potassium phosphate (K$_3$PO$_4$), potassium carbonate (K$_2$CO$_3$). The polar aprotic solvent can be: 1,4-dioxane, toluene, dimethylformamide (DMF). The inert gas can be nitrogen or argon.

b, Compound reacts, in the presence of a fluorine-containing reagent, in a polar aprotic solvent, at room temperature for 1-3 hours, to remove the protecting group t-butyldimethylsilyl (TBS), thereby giving compound VIII-2. The fluorine-containing reagent can be tetrabutylammonium fluoride ($^n$Bu$_4$NF). The polar aprotic solvent is tetrahydrofuran or dimethoxyethane.

c, Compound and methylsulfonyl chloride (MsCl) react, in the presence of an organic base, in a polar aprotic solvent, at a temperature from −10° C. to room temperature for 1-3 hours to give the corresponding compound VIII-3. The organic base can be triethylamine or pyridine. The polar aprotic solvent can be tetrahydrofuran or dichloromethane.

d, Compound VIII-3 and phthalimide potassium react, in a polar aprotic solvent, at a temperature from room temperature to 100° C. for 1-24 hours, to give the corresponding compound VIII-4. The polar aprotic solvent can be: N,N-dimethylformamide, acetonitrile.

e, Compound VIII-4 and methylamine alcohol solution react in a polar solvent at a temperature from room temperature to 80° C. for 1-12 hours, to give the corresponding compound VIII-5. The polar solvent is: methanol or ethanol.

f, Compound VIII-5 and 2-chlorothiophene-5-formyl chloride react, in the presence of an organic base, in a polar aprotic solvent, at a temperature from −10° C. to room temperature for 1-3 hours, to give the corresponding compound 40. The organic base can be triethylamine or pyridine. The polar aprotic solvent can be tetrahydrofuran or dichloromethane.

Another objective of the present invention is to provide a pharmaceutical composition comprising one or more of the compound represented by general formula (I) as the main active ingredient.

Still another objective of the present invention is to provide use of the compound represented by general formula (I) or a pharmaceutical composition comprising the compound represented by general formula (I) as the main active ingredient in the manufacture of a medicine for the treatment of diseases related to the FXa target, in particular vascular embolic disease.

The compound represented by general formula (I) according to the present invention contains at least two chiral centers, and it has enantiomers and diastereoisomers. For enantiomers, two enantiomers can be obtained by regular chiral separation or asymmetric synthesis. For diastereoisomers, the separation can be achieved by approaches such as fractional recrystallization or chromatographic separation. The compound of general formula (I) according to the present invention includes any one of such isomers or a mixture thereof.

When the compound of general formula (I) according to the present invention is used for preparing antithrombotic (anticoagulant) drugs, they can either be used alone, or can be mixed with pharmaceutically acceptable auxiliary materials (for example, excipients, diluents, etc.) to formulate tablet, capsule, granules, or syrup, etc. for oral administration.

SPECIFIC MODES FOR CARRYING OUT THE INVENTION

Examples

Figure 1:
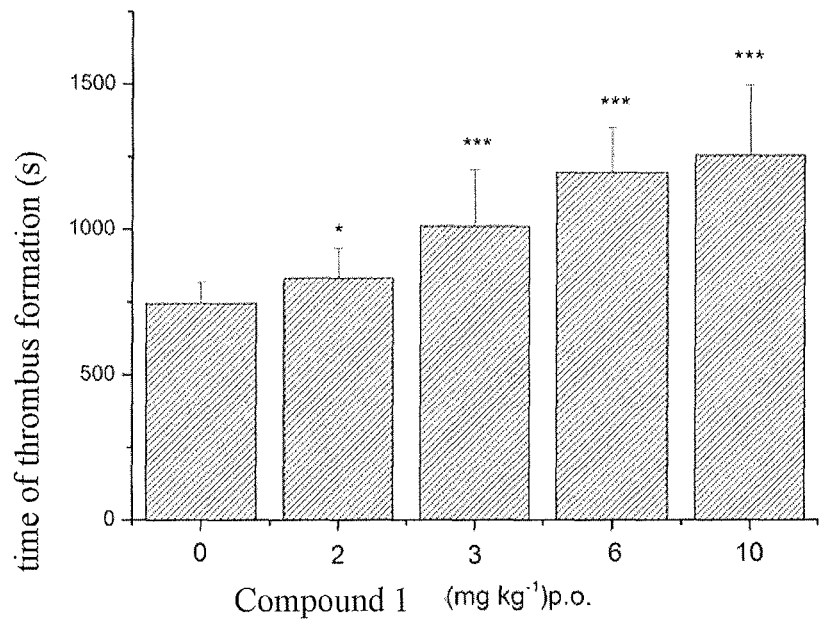
FIG. 1 depicts the effect of various dosages of the compound of the present invention on the time of thrombogenesis.

The present invention will now be further illustrated with reference to the following examples. However, it should be understood that these examples are to illustrate the present invention, but not to limit the present invention in any way. In all the examples, $^1$H-NMR was recorded by Varian Mercury 300 NMR spectrometer, and chemical shift is shown in δ (ppm); silica gel was used for separation, and it was all 200-300 mesh unless stated otherwise. All the proportions of the elution fluid are volume ratio.

PREPARATION EXAMPLES

Example 1

Preparation of 5-chloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)thiophene-2-carboxamide (compound 1)

(a) (3R,3aS)-3-((t-butyldimethylsiloxy)methyl)-7-(3-oxomorpholin-4-yl)-3a,4-dihydrobenzo[b]oxazolo[3,4-d][1,4]oxazin-1 (3H)-one

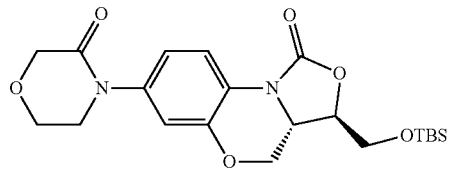 [SMILES: CC(C)(C)[Si](C)(C)OC[C@@H]1OC(=O)N2c3ccc(N4CCOCC4=O)cc3OC[C@@H]12]

Compound A

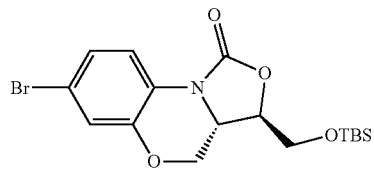 [SMILES: CC(C)(C)[Si](C)(C)OC[C@@H]1OC(=O)N2c3ccc(Br)cc3OC[C@@H]12]

[Journal of Medicinal Chemistry, 54(21), 7493-7502; 2011] (5 g, 12.08 mmol) was dissolved in 100 ml of anhydrous 1,4-dioxane, to which were added morpholone (1.83 g, 18.12 mmol) and cesium carbonate (9.84 g, 30.19 mmol) under the protection of argon. Pd$_2$(dba)$_3$ (0.55 g, 0.604 mmol) and 4,5-bis(diphenylphosphino)-9,9-dimethyl xanthene (Xantphos) (0.489 g, 0.845 mmol) were added and reacted under reflux and the protection of argon for 3 h. TLC (PE/EA=10/1) was employed to monitor the reaction. After the reactants reacted completely, the reaction was stopped, filtered under reduced pressure, and 1,4-dioxane was evaporated. Column chromatography (PE/EA=3/1, 2/1, 1/1) afforded off-white solid 3.216 g, yield 61.4%.

$^1$H NMR (300 MHz, DMSO-d$_6$) δ 7.78 (d, J=8.6 Hz, 1H), 7.06-6.98 (m, 2H), 4.55 (d, J 7.4 Hz, 2H), 4.17 (s, 2H), 3.95 (ddd, J=17.0, 16.6, 6.1 Hz, 6H), 3.68 (dd, J=5.9, 4.3 Hz, 2H), 0.88-0.83 (m, 9H), 0.08 (d, J=0.5 Hz, 6H). MS(EI) m/z: (M$^+$, 434).

(b) (3R,3 aS)-3-(hydroxymethyl)-7-(3-oxomorpholin-4-yl)-3a,4-dihydrobenzo[b]oxazolo[3,4-d][1,4]oxazin-1 (3H)-one

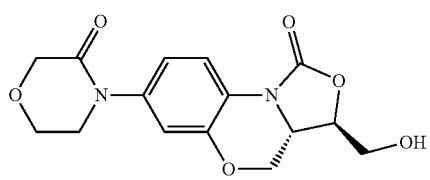 [SMILES: O=C1COCCN1c1ccc2c(c1)OC[C@H]1[C@H](CO)OC(=O)N21]

Compound (3R,3aS)-3-((t-butyldimethylsiloxy)methyl)-7-(3-oxomorpholin-4-yl)-3a,4-dihydrobenzo[b]oxazolo[3,4-d][1,4]oxazin-1 (3H)-one (3.6 g, 8.295 mmol) prepared as above in (a) was dissolved in 50 ml of THF, cooled to 0° C., to which was slowly added tetra-n-butylammonium fluoride (1M, 10 ml). The resulting mixture was raised to room temperature and reacted for 2 h. TLC (DCM/MeOH=10/1) was employed to monitor the reaction. After the reaction completed, THF was evaporated. The resulting mixture was washed with ethyl acetate/n-hexane=1/1 under stirring, filtered under reduced pressure, and dried to afford 1.88 g of white solid, yield 70.86%.

$^1$H NMR (400 MHz, DMSO-d$_6$) δ 7.91-7.75 (d, J=8.7 Hz, 1H), 7.09-7.04 (d, J=2.3 Hz, 1H), 7.03-6.96 (dd, J=8.7, 2.4 Hz, 1H), 5.37-5.28 (t, J=5.7 Hz, 1H), 4.59-4.49 (m, 1H), 4.48-4.41 (q, J=4.3 Hz, 1H), 4.25-4.12 (s, 2H), 4.07-3.99 (dd, J=4.7, 1.7 Hz, 2H), 3.98-3.91 (m, 2H), 3.83-3.62 (m, 4H). MS(EI) m/z: (M$^+$, 320).

(c) ((3R,3aS)-1-oxo-7-(3-oxomorpholin-4-yl)-1,3,3a,4-tetrahydrobenzo[b]oxazolo[3,4-d][1,4]oxazin-3-yl)methylmethanesulfonate

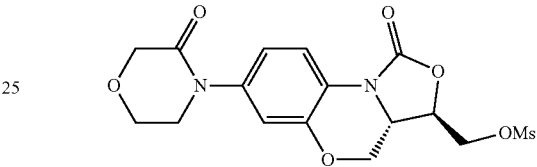

Compound (3R,3 aS)-3-(hydroxymethyl)-7-(3-oxomorpholin-4-yl)-3a,4-dihydrobenzo[b]oxazolo[3,4-d][1,4]oxazin-1 (3H)-one (4 g, 12.5 mmol) prepared as above in (b) was dissolved in 50 ml of DMF, cooled on ice-salt bath to 0° C. And then 3.5 ml of TEA was added, and methylsulfonyl chloride (1.72 g, 15 mmol) was added slowly in dropwise. After completion of the dropwise addition, the ice-salt bath was removed. The reaction mixture was agitated at room temperature for 3 h. TLC (DCM/MeOH=10/1) was employed to monitor the reaction. After the reaction completed, water (80 ml) was added for dilution. There was white solid precipitated, which was filtered and dried. The filtrate was extracted with EA (50 ml×3). The organic phase was combined, and washed sequentially with water (30 ml) and saturated NaCl (30 ml) solution, dried over anhydrous sodium sulfate, filtered, and the solvent was evaporated, to afford totally 3.92 g of white solid, yield: 78.6%.

$^1$H NMR (400 MHz, DMSO-d$_6$) δ 7.84 (d, J=8.7 Hz, 1H), 7.07 (d, J=2.3 Hz, 1H), 7.03 (dd, J=8.7, 2.3 Hz, 1H), 4.78 (s, 1H), 4.67-4.53 (m, 3H), 4.18 (s, 2H), 4.07 (d, J=6.2 Hz, 2H), 3.98-3.93 (m, 2H), 3.72-3.66 (m, 2H), 3.29 (s, 3H). MS(EI) m/z: (M$^+$, 398).

(d) 2-(((3S,3aS)-1-oxo-7-(3-oxomorpholin-4-yl)-1,3,3a,4-tetrahydrobenzo[b]oxazolo[3,4-d][1,4]oxazin-3-yl)methyl)isoindolin-1,3-dione

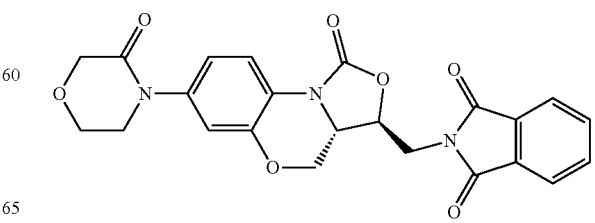

Compound ((3R,3aS)-1-oxo-7-(3-oxomorpholin-4-yl)-1,3,3a,4-tetrahydrobenzo[b]oxazolo[3,4-d][1,4]oxazin-3-yl)methylmethanesulfonate (3.91 g, 9.81 mmol) prepared as above in (c) was dissolved in 50 ml of DMF. Phthalimide potassium (2.72 g, 14.72 mmol) was added and the mixture was allowed to react at 80° C. for 2 h. TLC (DCM/MeOH=10/1) was employed to monitor the reaction. After the reaction completed, water (80 ml) was added for dilution. There was white solid precipitated, which was filtered and dried. The filtrate was extracted with EA (50 ml×3). The organic phase was combined, and washed sequentially with water (30 ml) and saturated NaCl (30 ml) solution, dried over anhydrous sodium sulfate, filtered, and the solvent was evaporated to afford totally 3.71 g of white solid, yield: 84.2%.

$^1$H NMR (400 MHz, CDCl$_3$) δ 8.01 (d, J=8.7 Hz, 1H), 7.91 (dd, J=5.4, 3.1 Hz, 2H), 7.79 (dd, J=5.5, 3.0 Hz, 2H), 6.99 (d, J=2.4 Hz, 1H), 6.95 (dd, J=8.7, 2.4 Hz, 1H), 4.65 (dd, J=12.1, 6.5 Hz, 1H), 4.47 (dd, J=10.6, 3.1 Hz, 1H), 4.33 (s, 2H), 4.23 (dd, J=14.3, 6.8 Hz, 1H), 4.11-3.99 (m, 4H), 3.88 (t, J=10.3 Hz, 1H), 3.74-3.69 (m, 2H). MS(EI) m/z: (M$^+$, 449).

(e) (3S,3 aS)-3-aminomethyl-7-(3-oxomorpholin-4-yl)-3a,4-dihydrobenzo[b]oxazolo[3,4-d][1,4]oxazin-1 (3H)-one

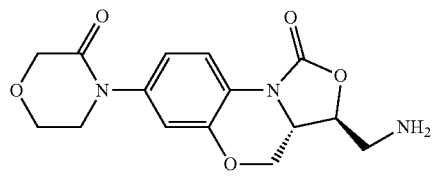 [SMILES: NC[C@@H]1OC(=O)N2c3ccc(N4CCOCC4=O)cc3OC[C@@H]12]

Compound 2-(((3S,3aS)-1-oxo-7-(3-oxomorpholin-4-yl)-1,3,3a,4-tetrahydrobenzo[b]oxazolo[3,4-d][1,4]oxazin-3-yl)methyl)isoindolin-1,3-dione (3.71 g, 8.263 mmol) prepared as above in (d) was partly dissolved in 50 ml of ethanol. 60 ml of methylamine alcohol solution was added and the mixture was allowed to react under reflux at 78° C. for 3 h. TLC (DCM/MeOH=10/1) was employed to monitor the reaction. After the reaction completed, the solvent was evaporated, and the remainder was directly subjected to the next step of reaction.

(f) 5-chloro-N-(((3S,3 aS)-1-oxo-7-(3-oxomorpholin-4-yl)-1,3,3a,4-tetrahydrobenzo[b]oxazolo[3,4-d][1,4]oxazin-3-yl)methyl)thiophene-2-carboxamide

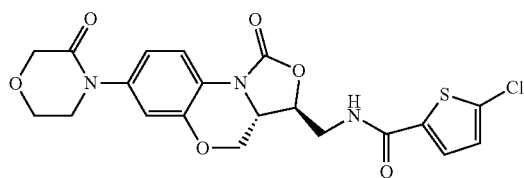 [SMILES: O=C(NC[C@@H]1OC(=O)N2c3ccc(N4CCOCC4=O)cc3OC[C@@H]12)c1ccc(Cl)s1]

The crude compound (3S,3 aS)-3-aminomethyl-7-(3-oxomorpholin-4-yl)-3a,4-dihydrobenzo[b]oxazolo[3,4-d][1,4]oxazin-1 (3H)-one, which was prepared as above in (e) and was not purified, was dissolved in 20 ml of DMF, cooled on ice-salt bath to 0° C. TEA (2.3 ml, 16.51 mmol) was added, and 5-chlorothiophene-2-formyl chloride (1.79 g, 9.91 mmol) was added slowly in dropwise. Then the cooling bath was removed, and the mixture was allowed to react at room temperature for 3 h. TLC (DCM/MeOH=10/1) was employed to monitor the reaction. After the reaction completed, the mixture was diluted with water (40 ml) and extracted with EA (30 ml×4). The organic phase was combined and washed with water and saturated saline solution for two times, respectively, dried over anhydrous sodium sulfate, filtered, and the solvent was evaporated. Column chromatography (DCM/MeOH=50/1) afforded 2.75 g of white solid, yield: 71.9% (two steps together).

$^1$H NMR (400 MHz, DMSO-d$_6$) δ 9.00 (t, J=5.8 Hz, 1H), 7.85 (d, J=8.7 Hz, 1H), 7.71 (d, J=4.1 Hz, 1H), 7.21 (d, J=4.0 Hz, 1H), 7.05 (d, J=2.3 Hz, 1H), 7.01 (dd, J=8.7, 2.3 Hz, 1H), 4.63-4.52 (m, 2H), 4.18 (s, 2H), 4.10-4.01 (m, 2H), 3.97-3.92 (m, 2H), 3.73 (t, J=5.5 Hz, 2H), 3.71-3.66 (m, 2H). MS(ESI) m/z: [(M+23)$^+$, 486.3].

Example 2

Preparation of 5-chloro-N-(((3S,3aS)-1-oxo-7-(2-oxopiperidin-1-yl)-1,3,3a,4-tetrahydrobenzo[b]oxazolo[3,4-d][1,4]oxazin-3-yl)methyl)thiophene-2-carboxamide (compound 2)

(a) (3R,3aS)-3-(((t-butyldimethylsilyl)oxy)methyl)-7-(2-oxopiperidin-1-yl)-3a,4-dihydrobenzo[b]oxazolo[3,4-d][1,4]oxazin-1 (3H)-one

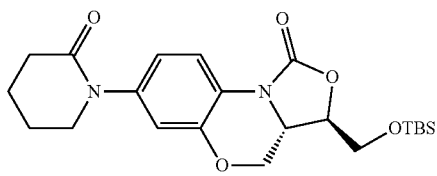 [SMILES: CC(C)(C)[Si](C)(C)OC[C@@H]1OC(=O)N2c3ccc(N4CCCCC4=O)cc3OC[C@@H]12]

Using compound A (the same as in Example 1) (2 g, 4.83 mmol), piperidin-2-one (0.717 g, 7.25 mmol), cesium carbonate (3.935 g, 0.012 mol), Pd$_2$(dba)$_3$ (0.31 g, 0.338 mmol), and Xantphos (0.28 g, 0.483 mmol) as starting materials, preparation following the method as described in Example 1(a) afforded white solid 1.016 g, yield: 48.6%.

$^1$H NMR (400 MHz, CDCl$_3$) δ 8.00 (dd, J=7.5, 1.6 Hz, 1H), 6.88 (dd, J=7.9, 1.9 Hz, 2H), 4.45 (dd, J=10.5, 3.2 Hz, 1H), 4.27 (td, J=5.6, 4.0 Hz, 1H), 4.10 (ddd, J=9.8, 6.5, 3.2 Hz, 1H), 3.97-3.84 (m, 3H), 3.59 (d, J=6.0 Hz, 2H), 2.55 (t, J=5.8 Hz, 2H), 1.99-1.87 (m, 4H), 0.89 (d, J=2.9 Hz, 9H), 0.11 (d, J=2.6 Hz, 6H). MS(EI) m/z: (M$^+$, 432).

(b) (3R,3 aS)-3-(hydroxymethyl)-7-(2-oxopiperidin-1-yl)-3a,4-dihydrobenzo[b]oxazolo[3,4-d][1,4]oxazin-1 (3H)-one

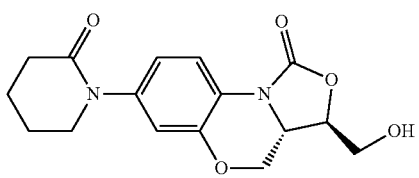 [SMILES: O=C1CCCCN1c1ccc2c(c1)OC[C@H]1[C@H](CO)OC(=O)N21]

Using compound (3R,3aS)-3-(((t-butyldimethylsilyl)oxy)methyl)-7-(2-oxopiperidin-1-yl)-3a,4-dihydrobenzo[b]oxazolo[3,4-d][1,4]oxazin-1(3H)-one (1.016 g, 2.352 mmol), and tetra-n-butylammonium fluoride (1M, 4.7 ml) as starting materials, preparation following the method as described in Example 1(b) afforded 0.642 g white solid, yield 85.8%.

¹H NMR (300 MHz, DMSO-d₆) δ 7.81 (d, J=8.4 Hz, 1H), 6.89 (d, J=7.7 Hz, 2H), 5.31 (s, 1H), 4.63-4.36 (m, 2H), 4.03 (s, 2H), 3.71 (d, J=12.3 Hz, 2H), 3.55 (s, 2H), 2.36 (s, 2H), 1.82 (s, 4H). MS(EI) m/z: (M⁺, 318).

(c) ((3R,3aS)-1-oxo-7-(2-oxopiperidin-1-yl)-1,3,3a,4-tetrahydrobenzo[b]oxazolo[3,4-d][1,4]oxazin-3-yl)methylmethanesulfonate

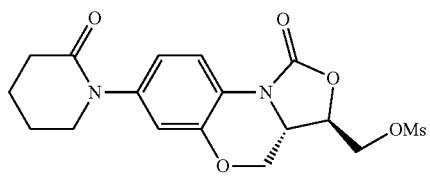 [SMILES: CS(=O)(=O)OC[C@@H]1OC(=O)N2c3ccc(N4CCCCC4=O)cc3OC[C@@H]12]

Using compound (3R,3aS)-3-(hydroxymethyl)-7-(2-oxopiperidin-1-yl)-3a,4-dihydrobenzo[b]oxazolo[3,4-d][1,4]oxazin-1 (3H)-one (0.642 g, 2.02 mmol), methylsulfonyl chloride (0.347 g, 3.03 mmol), TEA (0.408 g, 4.04 mmol) as starting materials, preparation following the method as described in Example 1(c) afforded white solid 0.774 g, yield: 96.8%.

¹H NMR (400 MHz, DMSO-d₆) δ 7.81 (d, J=8.8 Hz, 1H), 6.97-6.84 (m, 2H), 4.78 (d, J=2.2 Hz, 1H), 4.66-4.55 (m, 3H), 4.06 (d, J=5.9 Hz, 2H), 3.55 (t, J=5.5 Hz, 2H), 3.28 (s, 3H), 2.36 (t, J=6.2 Hz, 2H), 1.82 (d, J=3.1 Hz, 4H). MS(EI) m/z: (M⁺, 396).

(d) 2-(((3S,3aS)-1-oxo-7-(2-oxopiperidin-1-yl)-1,3,3a,4-tetrahydrobenzo[b]oxazolo[3,4-d][1,4]oxazin-3-yl)methyl)isoindolin-1,3-dione

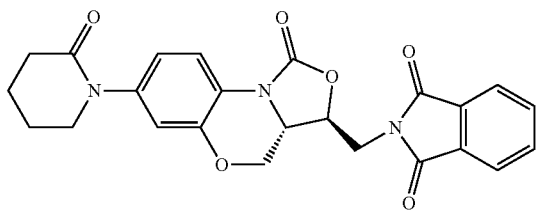 [SMILES: O=C1c2ccccc2C(=O)N1C[C@@H]1OC(=O)N2c3ccc(N4CCCCC4=O)cc3OC[C@@H]12]

Using compound ((3R,3aS)-1-oxo-7-(2-oxopiperidin-1-yl)-1,3,3a,4-tetrahydrobenzo[b]oxazolo[3,4-d][1,4]oxazin-3-yl)methylmethanesulfonate (0.774 g, 1.95 mmol), phthalimide potassium (0.542 g, 2.93 mmol) as starting materials, preparation following the method as described in Example 1(d) afforded white solid 0.693 g, yield: 79.3%.

¹H NMR (400 MHz, DMSO-d₆) δ 7.95-7.84 (m, 4H), 7.77 (d, J=8.6 Hz, 1H), 6.91-6.85 (m, 2H), 4.75-4.67 (m, 1H), 4.63 (dd, J=10.4, 3.0 Hz, 1H), 4.17 (td, J=6.9, 3.5 Hz, 1H), 4.13-3.99 (m, 3H), 3.54 (t, J=5.3 Hz, 2H), 2.36 (t, J=6.1 Hz, 2H), 1.82 (d, J=3.1 Hz, 4H). MS(EI) m/z: (M⁺, 447).

(e) (3S,3aS)-3-aminomethyl-7-(2-oxopiperidin-1-yl)-3a,4-dihydrobenzo[b]oxazolo[3,4-d][1,4]oxazin-1 (3H)-one

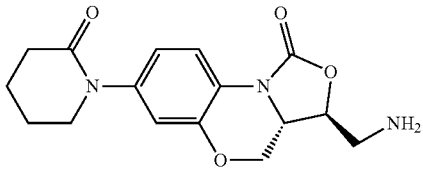 [SMILES: NC[C@@H]1OC(=O)N2c3ccc(N4CCCCC4=O)cc3OC[C@@H]12]

Using 2-(((3S,3aS)-1-oxo-7-(2-oxopiperidin-1-yl)-1,3,3a,4-tetrahydrobenzo[b]oxazolo[3,4-d][1,4]oxazin-3-yl)methyl)isoindolin-1,3-dione (0.693 g, 1.55 mmol) and 28 ml of methylamine alcohol solution as starting materials, preparation following the method as described in Example 1(e) afforded a crude product, which was directly subjected to the next step of reaction without purification.

(f) 5-chloro-N-(((3S,3aS)-1-oxo-7-(2-oxopiperidin-1-yl)-1,3,3a,4-tetrahydrobenzo[b]oxazolo[3,4-d][1,4]oxazin-3-yl)methyl)thiophene-2-carboxamide

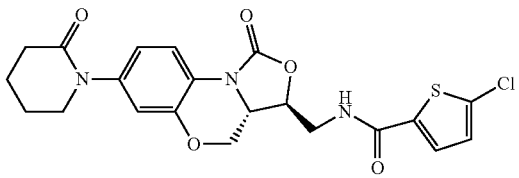 [SMILES: O=C(NC[C@@H]1OC(=O)N2c3ccc(N4CCCCC4=O)cc3OC[C@@H]12)c1ccc(Cl)s1]

Using the crude (3S,3aS)-3-aminomethyl-7-(2-oxopiperidin-1-yl)-3a,4-dihydrobenzo[b]oxazolo[3,4-d][1,4]oxazin-1 (3H)-one, 5-chlorothiophene-2-formyl chloride (0.337 g, 1.86 mmol), and TEA (0.313 g, 3.10 mmol) as starting materials, preparation following the method as described in Example 1(f) afforded white compound 0.518 g, yield of the two steps: 72.3%.

¹H NMR (400 MHz, CDCl₃) δ 7.98 (d, J=9.3 Hz, 1H), 7.34 (d, J=4.0 Hz, 1H), 6.90 (d, J=4.0 Hz, 1H), 6.87 (dt, J=4.5, 2.3 Hz, 3H), 4.54-4.41 (m, 2H), 3.96 (ddd, J=10.1, 7.0, 3.1 Hz, 1H), 3.90-3.70 (m, 3H), 3.59 (s, 2H), 2.55 (d, J=6.3 Hz, 2H), 1.97-1.89 (m, 4H). MS(EI) m/z: (M⁺, 461).

Example 3

Preparation of 3,6-dichloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)benzo[b]thiophene-2-carboxamide (compound 3)

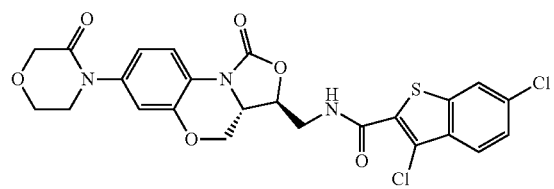 [SMILES: O=C(NC[C@@H]1OC(=O)N2c3ccc(N4CCOCC4=O)cc3OC[C@@H]12)c1sc2cc(Cl)ccc2c1Cl]

Using compound (3S,3aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (80 mg, 0.251 mmol) and 3,6-dichlorobenzo[b]thiophene-2-formyl chloride (99.9 mg, 0.376 mmol) as starting materials, preparation following the method as described in Example 1(f) afforded yellow solid 25 mg, yield: 28.2%.

¹H NMR (300 MHz, DMSO-$d_6$) δ 8.98-8.85 (t, J=5.9 Hz, 1H), 8.44-8.29 (s, 1H), 7.99-7.89 (d, J=8.8 Hz, 1H), 7.89-7.72 (d, J=8.6 Hz, 1H), 7.75-7.57 (d, J=8.7 Hz, 1H), 7.11-6.95 (m, 2H), 4.78-4.67 (d, J=5.5 Hz, 1H), 4.67-4.46 (d, J=8.6 Hz, 1H), 4.29-4.15 (s, 2H), 4.15-4.02 (m, 2H), 4.02-3.92 (t, J=5.0 Hz, 2H), 3.90-3.76 (m, 2H), 3.76-3.64 (t, J=5.0 Hz, 2H). MS(EI) m/z: (M⁺, 547).

Example 4

Preparation of 4-chloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)benzo[b]thiophene-2-carboxamide (compound 4)

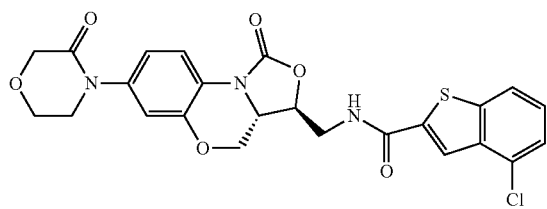 [SMILES: O=C(NC[C@@H]1OC(=O)N2c3ccc(N4CCOCC4=O)cc3OC[C@@H]12)c1cc2c(Cl)cccc2s1]

Using compound (3S,3 aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (40 mg, 0.125 mmol) and 4-chlorobenzo[b]thiophene-2-formyl chloride (60 mg, 0.26 mmol) as starting materials, preparation following the method as described in Example 1(f) afforded white solid 20 mg, yield: 31%.

¹H NMR (300 MHz, DMSO-$d_6$) δ 9.47-9.29 (s, 1H), 8.40-8.19 (s, 1H), 8.13-7.98 (d, J=8.0 Hz, 1H), 7.96-7.80 (d, J=8.7 Hz, 1H), 7.61-7.53 (m, 1H), 7.55-7.42 (m, 1H), 7.11-7.06 (d, J=2.0 Hz, 1H), 7.06-6.99 (dd, J=8.8, 2.2 Hz, 1H), 4.73-4.54 (dd, J=16.6, 7.9 Hz, 2H), 4.22-4.16 (s, 2H), 4.12-4.06 (dd, J=7.3, 2.1 Hz, 1H), 4.01-3.93 (t, J=5.0 Hz, 2H), 3.88-3.77 (t, J=5.7 Hz, 2H), 3.74-3.61 (t, J=5.2 Hz, 2H), 3.21-3.16 (dd, J=5.2, 1.1 Hz, 1H). MS(ESI) m/z: [(M+1)⁺, 514].

Example 5

Preparation of 5-chloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)benzo[b]thiophene-2-carboxamide (compound 5)

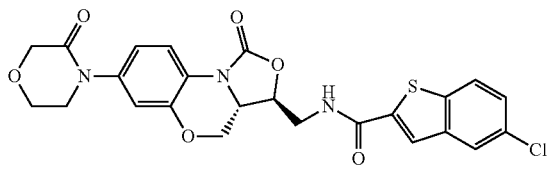 [SMILES: O=C(NC[C@@H]1OC(=O)N2c3ccc(N4CCOCC4=O)cc3OC[C@@H]12)c1cc2cc(Cl)ccc2s1]

Using compound (3S,3aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (56.8 mg, 0.178 mmol) and 5-chlorobenzo[b]thiophene-2-formyl chloride (61.7 mg, 0.267 mmol) as starting materials, preparation following the method as described in Example 1(f) afforded white solid 25 mg, yield: 21.8%.

¹H NMR (300 MHz, DMSO-$d_6$) δ 9.31-9.16 (t, J=5.7 Hz, 1H), 8.13-8.03 (m, 3H), 7.90-7.77 (d, J=8.7 Hz, 1H), 7.54-7.43 (dd, J=8.7, 2.1 Hz, 1H), 7.09-7.02 (d, J=2.3 Hz, 1H), 7.02-6.94 (dd, J=8.7, 2.3 Hz, 1H), 4.66-4.59 (q, J=5.9 Hz, 1H), 4.59-4.48 (dd, J=9.4, 2.2 Hz, 1H), 4.19-4.13 (s, 2H), 4.13-4.00 (m, 2H), 3.97-3.88 (dd, J=6.0, 4.1 Hz, 2H), 3.81-3.72 (t, J=5.6 Hz, 2H), 3.70-3.61 (dd, J=6.1, 4.2 Hz, 2H). MS(ESI) m/z: [(M+1)⁺, 514].

Example 6

Preparation of 7-chloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)benzo[b]thiophene-2-carboxamide (compound 6)

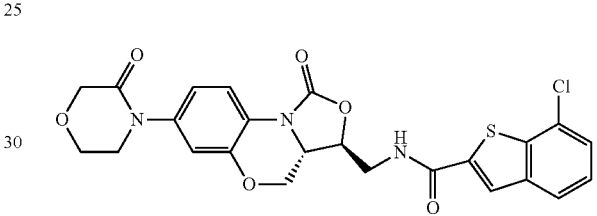

Using compound (3S,3aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (40 mg, 0.178 mmol) and 7-chlorobenzo[b]thiophene-2-formyl chloride (61.7 mg, 0.267 mmol) as starting materials, preparation following the method as described in Example 1(f) afforded white solid 30 mg, yield: 46.55%.

¹H NMR (400 MHz, DMSO-$d_6$) δ 9.37-9.23 (t, J=5.9 Hz, 1H), 8.32-8.18 (s, 1H), 8.05-7.92 (d, J=8.0 Hz, 1H), 7.92-7.78 (d, J=8.7 Hz, 1H), 7.66-7.57 (d, J=7.6 Hz, 1H), 7.55-7.41 (t, J=7.8 Hz, 1H), 7.08-7.05 (d, J=2.3 Hz, 1H), 7.03-6.99 (dd, J=8.8, 2.4 Hz, 1H), 4.77-4.61 (m, 1H), 4.62-4.54 (dd, J=10.0, 2.7 Hz, 1H), 4.29-4.15 (s, 2H), 3.76-3.59 (m, 2H), 4.14-4.00 (m, 2H), 4.00-3.87 (dd, J=5.8, 4.0 Hz, 2H), 3.88-3.73 (m, 2H). MS(EI) m/z: (M⁺, 513).

Example 7

Preparation of 6-chloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)benzo[b]thiophene-2-carboxamide (compound 7)

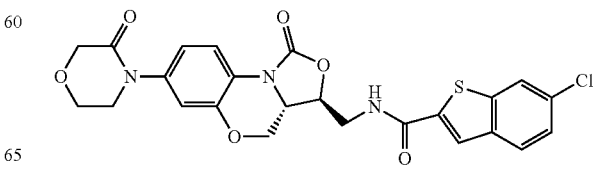

Using compound (3S,3 aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (40 mg, 0.178 mmol) and 6-chlorobenzo[b]thiophene-2-formyl chloride (61.7 mg, 0.267 mmol) as starting materials, preparation following the method as described in Example 1(f) afforded white solid 35 mg, yield: 54.31%.

¹H NMR (300 MHz, DMSO-d₆) δ 8.98-8.85 (t, J=5.9 Hz, 1H), 8.44-8.29 (s, 1H), 7.99-7.89 (d, J=8.8 Hz, 1H), 7.89-7.72 (d, J=8.6 Hz, 1H), 7.75-7.57 (d, J=8.7 Hz, 1H), 7.11-6.95 (m, 2H), 4.78-4.67 (d, J=5.5 Hz, 1H), 4.67-4.46 (d, J=8.6 Hz, 1H), 4.29-4.15 (s, 2H), 4.15-4.02 (m, 2H), 4.02-3.92 (t, J=5.0 Hz, 2H), 3.90-3.76 (m, 2H), 3.76-3.64 (t, J=5.0 Hz, 2H). MS(EI) m/z: (M⁺, 513).

Example 8

Preparation of 2,2-dichloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl) acetamide (compound 8)

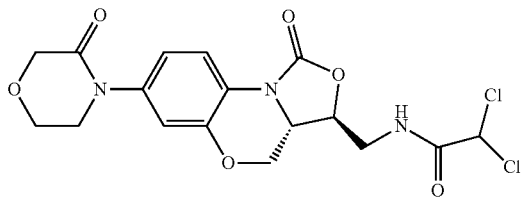 [SMILES: O=C(NC[C@@H]1OC(=O)N2c3ccc(N4CCOCC4=O)cc3OC[C@@H]12)C(Cl)Cl]

Using compound (3S,3 aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (40 mg, 0.178 mmol) and 2,2-dichloro acetyl chloride (27.6 mg, 0.188 mmol) as starting materials, preparation following the method as described in Example 1(f) afforded white solid 20 mg, yield: 37%.

¹H NMR (400 MHz, DMSO-d₆) δ 9.07-8.94 (t, J=5.8 Hz, 1H), 7.94-7.72 (d, J=8.6 Hz, 1H), 7.07-7.04 (d, J=2.3 Hz, 1H), 7.04-6.99 (dd, J=8.7, 2.3 Hz, 1H), 6.55-6.50 (s, 1H), 4.59-4.53 (m, 2H), 4.24-4.10 (s, 2H), 4.07-3.98 (q, J=8.4, 7.0 Hz, 2H), 3.97-3.88 (t, J=5.1 Hz, 2H), 3.71-3.68 (d, J=5.1 Hz, 2H), 3.68-3.64 (m, 2H). MS(EI) m/z: (M⁺, 429).

Example 9

Preparation of 4,5-dichloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)thiophene-2-carboxamide (compound 9)

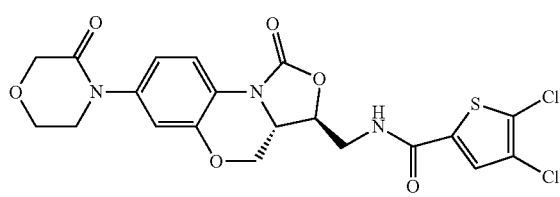 [SMILES: O=C(NC[C@@H]1OC(=O)N2c3ccc(N4CCOCC4=O)cc3OC[C@@H]12)c1cc(Cl)c(Cl)s1]

Using compound (3S,3aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (80 mg, 0.251 mmol) and 4,5-dichlorothiophene-2-formyl chloride (81 mg, 0.301 mmol) as starting materials, preparation following the method as described in Example 1(f) afforded white solid 50 mg, yield: 40%.

¹H NMR (400 MHz, DMSO-d₆) δ 9.18-9.04 (t, J=5.9 Hz, 1H), 7.95-7.89 (s, 1H), 7.89-7.81 (d, J=8.7 Hz, 1H), 7.08-7.04 (d, J=2.2 Hz, 1H), 7.07-6.99 (m, 1H), 4.71-4.46 (J=7.7 Hz, 2H), 4.22-4.12 (s, 2H), 4.10-4.00 (m, 2H), 4.00-3.90 (t, J=5.0 Hz, 2H), 3.87-3.71 (t, J=5.7 Hz, 2H), 3.71-3.63 (t, J=5.3 Hz, 2H). MS(ESI) m/z: [(M−1)⁺, 496].

Example 10

Preparation of 2-chloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)thiophene-5-carboxamide (compound 10)

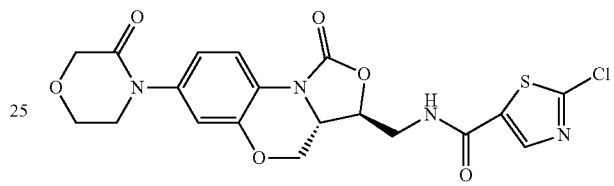

Using compound (3S,3aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (80 mg, 0.251 mmol) and 2-chlorothiazolyl-5-formyl chloride (55 mg, 0.301 mmol) as starting materials, preparation following the method as described in Example 1(f) afforded light yellow solid 60 mg, yield: 51.5%.

¹H NMR (400 MHz, DMSO-d₆) δ 9.31-9.11 (t, J=6.0 Hz, 1H), 8.41-8.33 (s, 1H), 7.94-7.77 (d, J=8.7 Hz, 1H), 7.08-7.04 (d, J=2.3 Hz, 1H), 7.04-6.99 (dd, J=8.7, 2.4 Hz, 1H), 4.73-4.46 (m, 2H), 4.23-4.13 (s, 2H), 4.10-4.01 (m, 2H), 4.00-3.87 (dd, J=5.9, 4.0 Hz, 2H), 3.85-3.72 (t, J=5.5 Hz, 2H), 3.72-3.60 (dd, J=6.0, 4.3 Hz, 2H). MS(EI) m/z: (M⁺, 464).

Example 11

Preparation of 5-chloro-N-(((3S,3aS)-1-oxo-7-(7-oxo-1,4-dioxy-8-azaspiro[4.5]heptan-8-yl)-1,3,3a,4-tetrahydrobenzo[b]oxazolo[3,4-d][1,4]oxazin-3-yl)methyl)thiophene-2-carboxamide (compound 11)

(a) 1,4-dioxy-8-azaspiro[4.5]heptan-7-one

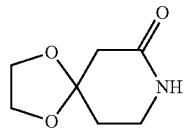 [SMILES: O=C1CC2(CCN1)OCCO2]

2,4-piperidinedione (300 mg, 2.65 mmol) was suspended in 25 ml of toluene. Ethylene glycol (329 mg, 5.3 mmol) and p-toluenesulfonic acid monohydrate (100 mg, 0.53 mmol) were added, and water was removed from the resulting mixture by reflux at 110° C. TLC (DCM/MeOH=10/1) was employed to monitor the reaction. After the reaction completed, aqueous solution of sodium bicarbonate was added, and the resulting mixture was extracted with EA (30 ml×4). The organic phase was combined, washed with water and saturated saline solution for two times respectively, dried over anhydrous sodium sulfate, filtered, and the solvent was evaporated. Column chromatography (DCM/MeOH=50/1) afforded white solid 220 mg, yield: 52.8%.

¹H NMR (300 MHz, CDCl₃) δ 6.88-6.57 (s, 1H), 4.07-3.79 (dt, J=6.4, 3.1 Hz, 4H), 3.46-3.25 (t, J=6.2 Hz, 2H), 2.67-2.52 (s, 2H), 1.96-1.81 (t, J=6.1 Hz, 2H). MS(ESI) m/z: [(M+23)⁺, 180.2].

(b) (3R,3aS)-3-((t-butyldimethylsiloxy)methyl)-7-(7-oxo-1,4-dioxy-8-azaspiro[4.5]heptan-8-yl)-3a,4-dihydrobenzo[b]oxazolo[3,4-d][1,4]oxazin-1 (3H)-one

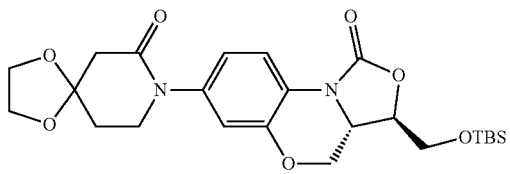 [SMILES: CC(C)(C)[Si](C)(C)OC[C@@H]1OC(=O)N2c3ccc(N4CCC5(CC4=O)OCCO5)cc3OC[C@@H]12]

Using 1,4-dioxy-8-azaspiro[4.5]heptan-7-one (0.46 g, 2.899 mmol), compound A (the same as compound A in Example 1) (1.00 g, 2.415 mmol), Pd₂(dba)₃ (0.15 g, 0.169 mmol), Xantphos (0.14 g, 0.242 mmol), and cesium carbonate (1.96 g, 6.038 mmol) as starting materials, dioxane as solvent, preparation following the method as described in Example 1(a) afforded golden solid 0.43 g, yield 36.3%.

¹H NMR (300 MHz, CDCl₃) δ 8.05-7.98 (m, 1H), 6.92-6.89 (d, J=1.5 Hz, 1H), 6.90-6.86 (m, 1H), 4.49-4.41 (m, 1H), 4.31-4.23 (q, J=5.4 Hz, 1H), 4.15-4.07 (m, 1H), 4.07-3.98 (q, J=5.3 Hz, 4H), 3.95-3.90 (m, 2H), 3.90-3.83 (m, 2H), 3.72-3.64 (t, J=6.1 Hz, 2H), 2.80-2.76 (s, 2H), 2.14-2.07 (t, J=6.2 Hz, 2H), 0.94-0.85 (d, J=1.3 Hz, 9H), 0.13-0.06 (m, 6H). MS(ESI) m/z: [(M+1)⁺, 491.4].

(c) (3R,3aS)-3-(hydroxymethyl)-7-(7-oxo-1,4-dioxy-8-azaspiro[4.5]heptan-8-yl)-3a,4-dihydrobenzo[b]oxazolo[3,4-d][1,4]oxazin-1 (3H)-one

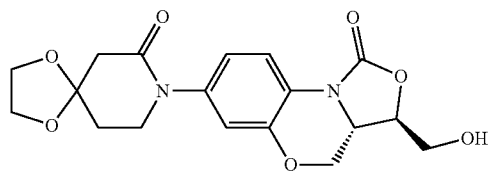 [SMILES: O=C1CC2(CCN1c1ccc3c(c1)OC[C@H]1[C@H](CO)OC(=O)N31)OCCO2]

Using compound (3R,3aS)-3-((t-butyldimethylsiloxy)methyl)-7-(7-oxo-1,4-dioxy-8-azaspiro[4.5]heptan-8-yl)-3a,4-dihydrobenzo[b]oxazolo[3,4-d][1,4]oxazin-1(3H)-one (0.43 g, 0.876 mmol), and TBAF (0.46 g, 1.753 mmol) as starting materials, DCM as solvent, preparation following the method as described in Example 1(b) afforded white solid 0.31 g, yield 94.0%.

¹H NMR (400 MHz, CDCl₃) δ 8.08-7.97 (m, 1H), 6.91-6.90 (s, 1H), 6.90-6.87 (m, 1H), 4.50-4.42 (dd, J=10.6, 3.2 Hz, 1H), 4.38-4.27 (dt, J=7.0, 4.3 Hz, 1H), 4.16-4.07 (m, 1H), 2.14-2.06 (m, 2H), 4.08-3.97 (tdd, J=7.0, 3.9, 1.9 Hz, 4H), 3.97-3.91 (m, 1H), 3.90-3.85 (m, 1H), 3.85-3.79 (m, 1H), 3.71-3.65 (m, 2H), 2.81-2.73 (t, J=1.0 Hz, 2H), 1.01-0.94 (t, J=7.4 Hz, 1H). MS(ESI) m/z: [(M+1)⁺, 377.3].

(d) ((3R,3aS)-1-oxo-7-(7-oxo-1,4-dioxy-8-azaspiro[4.5]heptan-8-yl)-1,3,3a,4-tetrahydrobenzo[b]oxazolo[3,4-d][1,4]oxazin-3-yl)methylmethanesulfonate

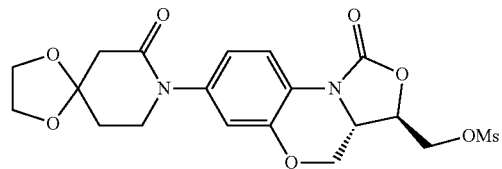 [SMILES: CS(=O)(=O)OC[C@@H]1OC(=O)N2c3ccc(N4CCC5(CC4=O)OCCO5)cc3OC[C@@H]12]

Using compound (3R,3aS)-3-(hydroxymethyl)-7-(7-oxo-1,4-dioxy-8-azaspiro[4.5]heptan-8-yl)-3a,4-dihydrobenzo[b]oxazolo[3,4-d][1,4]oxazin-1 (3H)-one (0.31 g, 0.824 mmol), MSCl (0.14 g, 1.235 mmol), and Et₃N (0.17 g, 1.648 mmol) as starting materials, DCM as solvent, preparation following the method as described in Example 1(c) afforded white solid 0.31 g, yield: 82.8%.

¹H NMR (400 MHz, CDCl₃) δ 8.04-7.96 (d, J=9.2 Hz, 2H), 6.96-6.87 (m, 4H), 4.58-4.47 (m, 8H), 4.14-4.08 (m, 1H), 4.09-3.98 (m, 7H), 3.97-3.86 (t, J=10.3 Hz, 2H), 3.72-3.63 (t, J=6.3 Hz, 4H), 3.17-3.11 (s, 6H), 2.81-2.76 (s, 4H), 2.16-2.06 (t, J=6.2 Hz, 4H). MS(ESI) m/z: [(M+23)⁺, 477.3].

(e) 2-(((3S,3aS)-1-oxo-7-(7-oxo-1,4-dioxy-8-azaspiro[4.5]heptan-8-yl)-1,3,3a,4-tetrahydrobenzo[b]oxazolo[3,4-d][1,4]oxazin-3-yl)methyl)isoindolin-1,3-dione

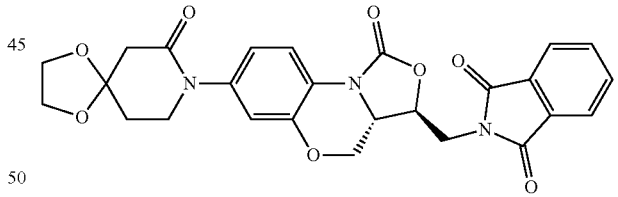

Using compound ((3R,3aS)-1-oxo-7-(7-oxo-1,4-dioxy-8-azaspiro[4.5]heptan-8-yl)-1,3,3a,4-tetrahydrobenzo[b]oxazolo[3,4-d][1,4]oxazin-3-yl)methylmethanesulfonate (0.31 g, 0.682 mmol), and phthalimide potassium (0.19 g, 1.023 mmol) as starting materials, DMF as solvent, preparation following the method as described in Example 1(d) afforded white solid 0.22 g, yield 63.8%.

¹H NMR (400 MHz, CDCl₃) δ 8.03-7.94 (m, 1H), 7.94-7.86 (m, 2H), 7.83-7.73 (dd, J=5.4, 3.0 Hz, 2H), 6.93-6.89 (s, 1H), 6.89-6.86 (s, 1H), 4.70-4.59 (q, J=6.3 Hz, 1H), 4.51-4.41 (dt, J=10.8, 2.5 Hz, 1H), 4.28-4.17 (m, 1H), 4.11-4.06 (s, 1H), 4.05-3.96 (m, 4H), 3.93-3.82 (t, J=10.3 Hz, 1H), 3.82-3.74 (t, J=6.9 Hz, 1H), 3.70-3.64 (t, J=6.2 Hz, 2H), 2.79-2.75 (s, 2H), 2.14-2.06 (t, J=6.2 Hz, 2H). MS(EI) m/z: (M⁺, 505).

(f) (3S,3aS)-3-(aminomethyl)-7-(7-oxo-1,4-dioxy-8-azaspiro[4.5]heptan-8-yl)-3a,4-dihydrobenzo[b]oxazolo[3,4-d][1,4]oxazin-1 (3H)-one

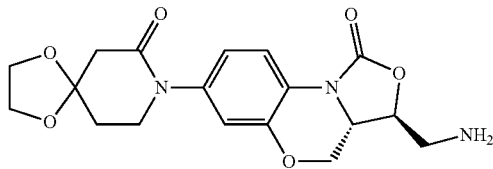 [SMILES: NC[C@@H]1OC(=O)N2c3ccc(N4CCC5(CC4=O)OCCO5)cc3OC[C@@H]12]

Using compound 2-(((3S,3aS)-1-oxo-7-(7-oxo-1,4-dioxy-8-azaspiro[4.5]heptan-8-yl)-1,3,3a,4-tetrahydrobenzo[b]oxazolo[3,4-d][1,4]oxazin-3-yl)methyl)isoindolin-1,3-dione (0.21 g, 0.415 mmol), and methylamine alcohol (0.03 g, 0.830 mmol) as starting materials, ethanol as solvent, preparation following the method as described in Example 1(e) afforded white solid 0.12 g, yield 76.9%.

(g) 5-chloro-N-(((3S,3 aS)-1-oxo-7-(7-oxo-1,4-dioxy-8-azaspiro[4.5]heptan-8-yl)-1,3,3a,4-tetrahydrobenzo[b]oxazolo[3,4-d][1,4]oxazin-3-yl)methyl)thiophene-2-carboxamide

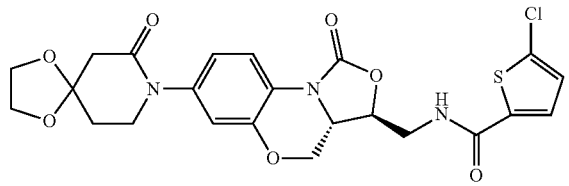 [SMILES: O=C(NC[C@@H]1OC(=O)N2c3ccc(N4CCC5(CC4=O)OCCO5)cc3OC[C@@H]12)c1ccc(Cl)s1]

Compound (3S,3aS)-3-(aminomethyl)-7-(7-oxo-1,4-dioxy-8-azaspiro[4.5]heptan-8-yl)-3a,4-dihydrobenzo[b]oxazolo[3,4-d][1,4]oxazin-1 (3H)-one (0.12 g, 0.320 mmol) was dissolved in a mixed solvent of DCM (10 ml) and DMF (2 ml). 5-chlorothiophene-2-carboxylic acid (0.08 g, 0.480 mmol) and Et$_3$N (0.10 g, 0.960 mmol) were added, and HATU (0.22 g, 0.576 mmol) were added under ice bath. The resulting mixture was agitated at room temperature for 3 h. TLC (DCM/MeOH=10/1) was employed to monitor the reaction. After the reaction completed, 20 ml of water was added, and the mixture was extracted with EA (20 ml×3). The organic phase was combined, washed with water and saturated saline solution for two times respectively, dried over anhydrous sodium sulfate, filtered, and the solvent was evaporated. Column chromatography (DCM/MeOH=50/1) afforded white solid 0.11 g, yield 66.2%.

$^1$H NMR (400 MHz, DMSO-d$_6$) δ 9.06-8.97 (t, J=5.8 Hz, 1H), 7.88-7.80 (m, 1H), 7.74-7.68 (d, J=4.0 Hz, 1H), 7.24-7.19 (d, J=3.9 Hz, 1H), 6.91-6.85 (h, J=2.3 Hz, 2H), 4.64-4.57 (q, J=5.5 Hz, 1H), 4.56-4.51 (m, 1H), 4.11-4.00 (m, 2H), 3.98-3.92 (m, 4H), 3.75-3.70 (t, J=5.7 Hz, 2H), 3.63-3.56 (t, J=6.3 Hz, 2H), 2.64-2.62 (s, 2H), 2.09-2.01 (t, J=6.3 Hz, 2H). MS(ESI) m/z: [(M+23)$^+$, 542.4].

Example 12

Preparation of 5-chloro-N-(((3S,3aS)-7-((R)-4-methoxyl-2-oxopiperidin-1-yl)-1-oxo-1,3,3a,4-tetrahydrobenzo[b]oxazolo[3,4-d][1,4]oxazin-3-yl)methyl)-thiophene-2-carboxamide (compound 12)

(a) (R) 4-cyano-3-methoxyl butyric acid ethyl ester

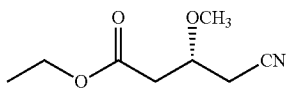

(R)4-cyano-3-hydroxy butyric acid ethyl ester (1.5 g, 9.54 mmol) was dissolved in iodomethane (20 ml). Silver oxide solid (3.3 g, 14.32 mmol) was added, and the reaction mixture was agitated at room temperature overnight. TLC (PE/EA=2/1) was employed to monitor the reaction. After the reaction completed, the silver oxide solid was removed by filtration, and the solvent was evaporated. Column chromatography (PE/EA=10/1) afforded colorless transparent liquid 1.0 g, yield 63.1%.

$^1$H NMR (400 MHz, CDCl$_3$) δ 4.22-4.11 (q, J=7.1 Hz, 1H), 4.00-3.86 (tt, J=6.3, 5.4 Hz, 0H), 3.49-3.40 (s, 2H), 2.80-2.54 (m, 2H), 1.34-1.23 (t, J=7.2 Hz, 2H). MS(ESI) m/z: [(M+1)$^+$, 172.2].

(b) (R)-4-methoxylpiperidin-2-one

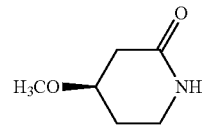

(R) 4-cyano-3-methoxyl butyric acid ethyl ester (1.0 g, 5.84 mmol) was dissolved in methanol (20 ml). PtO$_2$.3H$_2$O (0.16 g, 0.584 mmol) was added and the resulting mixture was allowed to react under hydrogen pressure (50 psi) for 20 h. TLC (DCM/MeOH=10/1) was employed to monitor the reaction. After the reaction completed, the reaction mixture was filtered and dried by spinning. Column chromatography (DCM/MeOH-50/1) afforded colorless transparent liquid 0.5 g, yield 66.3%.

$^1$H NMR (400 MHz, CDCl$_3$) δ 7.26-7.15 (s, 1H), 3.69-3.60 (m, 1H), 3.46-3.36 (m, 1H), 3.35-3.30 (s, 3H), 3.24-3.13 (dddd, J=11.9, 6.7, 5.2, 2.3 Hz, 1H), 2.61-2.33 (m, 2H), 1.98-1.77 (m, 2H). MS(ESI) m/z: [(M+23)$^+$, 152.2].

(c) (3R,3 aS)-3-((t-butyldimethylsiloxy)methyl)-7-((R)-4-methoxyl-2-oxopiperidin-1-yl)-3a,4-dihydrobenzo[b]oxazolo[3,4-d][1,4]oxazin-1 (3H)-one

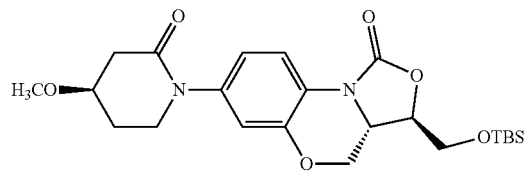 [SMILES: CO[C@@H]1CCN(c2ccc3c(c2)OC[C@H]2[C@H](CO[Si](C)(C)C(C)(C)C)OC(=O)N32)C(=O)C1]

Using compound (R)-4-methoxylpiperidin-2-one (0.98 g, 7.62 mmol), compound A (the same as in Example 1) (2.63 g, 6.35 mmol), Pd₂(dba)₃ (0.29 g, 0.318 mmol), Xantphos (0.29 g, 0.508 mmol), and cesium carbonate (4.14 g, 12.7 mmol) as starting materials, dioxane as solvent, preparation following the method as described in Example 1 (a) afforded golden oily liquid 1.5 g, yield 51.1%.

¹H NMR (400 MHz, CDCl₃) δ 8.12-7.96 (d, J=8.4 Hz, 1H), 6.97-679 (m, 2H), 4.51-4.40 (dd, J=10.5, 3.1 Hz, 1H), 4.34-4.21 (q, J=5.0, 4.3 Hz, 1H), 4.21-4.07 (ddd, J=9.8, 6.5, 3.2 Hz, 1H), 4.00-3.68 (m, 5H), 3.65-3.47 (dd, J=12.1, 6.0 Hz, 1H), 3.45-3.33 (s, 3H), 2.89-2.54 (m, 2H), 2.33-1.92 (m, 2H), 1.02-0.82 (s, 9H), 0.21-0.05 (s, 6H). MS(ESI) m/z: [(M+1)⁺, 463.5].

(d) (3R,3aS)-3-(hydroxymethyl)-7-((R)-4-methoxyl-2-oxopiperidin-1-yl)-3a,4-dihydrobenzo[b]oxazolo[3,4-d][1,4]oxazin-1 (3H)-one

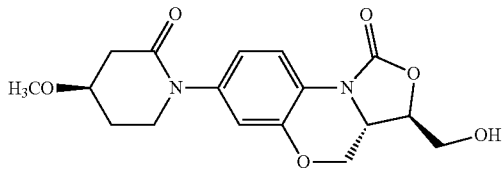 [SMILES: CO[C@@H]1CCN(c2ccc3c(c2)OC[C@H]2[C@H](CO)OC(=O)N32)C(=O)C1]

Using compound (3R,3aS)-3-((t-butyldimethylsiloxy)methyl)-7-((R)-4-methoxyl-2-oxopiperidin-1-yl)-3a,4-dihydrobenzo[b]oxazolo[3,4-d][1,4]oxazin-1(3H)-one (1.5 g, 3.24 mmol), and TBAF (1.27 g, 4.86 mmol) as starting materials, DCM as solvent, preparation following the method as described in Example 1 (b) afforded white solid 0.85 g, yield 75.0%.

¹H NMR (400 MHz, CDCl₃) δ 8.10-7.87 (d, J=8.5 Hz, 1H), 6.99-6.77 (m, 2H), 4.52-4.39 (dd, J=10.6, 3.2 Hz, 1H), 4.32-4.21 (dd, J=7.9, 3.5 Hz, 1H), 4.15-4.04 (m, 1H), 3.96-3.68 (m, 5H), 3.58-3.45 (dt, J=11.8, 5.4 Hz, 1H), 3.46-3.34 (s, 3H), 3.00-2.95 (t, J=6.3 Hz, 1H), 2.80-2.61 (m, 2H), 2.15-2.01 (m, 2H). MS(ESI) m/z: [(M+1)⁺, 349.4].

(e) (3R,3aS)-7-((R)-4-methoxyl-2-oxopiperidin-1-yl)-1-oxo-1,3,3a,4-tetrahydrobenzo[b]oxazolo[3,4-d][1,4]oxazin-3-yl)methyl-methanesulfonate

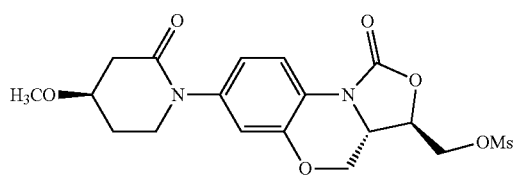

Using compound (3R,3aS)-3-(hydroxymethyl)-7-((R)-4-methoxyl-2-oxopiperidin-1-yl)-3a,4-dihydrobenzo[b]oxazolo[3,4-d][1,4]oxazin-1 (3H)-one (0.85 g, 2.440 mmol), MsCl (0.42 g, 3.660 mmol), and Et₃N (4.93 g, 4.880 mmol) as starting materials, DCM as solvent, preparation following the method as described in Example 1(c) afforded white solid 0.89 g, yield 85%.

¹H NMR (400 MHz, CDCl₃) δ 8.03-7.96 (d, J=9.2 Hz, 1H), 6.94-6.89 (m, 2H), 4.59-4.44 (m, 3H), 4.05-3.98 (m, 1H), 3.94-3.86 (m, 1H), 3.84-3.75 (tq, J=8.5, 4.8, 4.0 Hz, 2H), 3.56-3.47 (dt, J=11.8, 5.6 Hz, 1H), 3.44-3.40 (s, 3H), 3.17-3.12 (s, 3H), 2.83-2.62 (m, 2H), 2.17-2.03 (m, 1H). MS(ESI) m/z: [(M+1)⁺, 427.4].

(f) 2-(((3S,3aS)-7-((R)-4-methoxyl-2-oxopiperidin-1-yl)-1-oxo-1,3,3a,4-tetrahydrobenzo[b]oxazolo[3,4-d][1,4]oxazin-3-yl)methyl)-isoindolin-1,3-dione

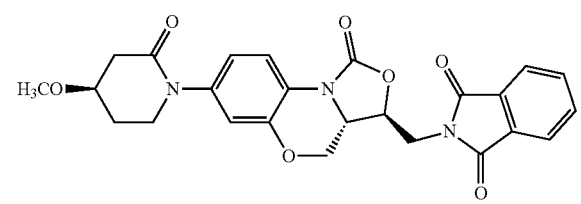 [SMILES: CO[C@@H]1CCN(c2ccc3c(c2)OC[C@H]2[C@H](CN4C(=O)c5ccccc5C4=O)OC(=O)N32)C(=O)C1]

Using compound (3R,3aS)-7-((R)-4-methoxyl-2-oxopiperidin-1-yl)-1-oxo-1,3,3a,4-tetrahydrobenzo[b]oxazolo[3,4-d][1,4]oxazin-3-yl)methyl-methanesulfonate (0.89 g, 2.087 mmol), and phthalimide potassium (0.58 g, 3.130 mmol) as starting materials, DMF as solvent, preparation following the method as described in Example 1 (d) afforded white solid 0.79 g, yield 80%.

¹H NMR (400 MHz, CDCl₃) δ 8.00-7.95 (d, J=8.2 Hz, 1H), 7.94-7.90 (dd, J=5.5, 3.0 Hz, 2H), 7.82-7.78 (dd, J=5.4, 3.1 Hz, 2H), 6.93-6.87 (m, 2H), 4.69-4.63 (q, J=6.6 Hz, 1H), 4.51-4.45 (dd, J=10.6, 3.1 Hz, 1H), 4.28-4.21 (m, 1H), 4.11-4.03 (m, 3H), 3.93-3.86 (t, J=10.3 Hz, 1H), 3.83-3.74 (dt, J=12.2, 4.3 Hz, 2H), 3.55-3.47 (dt, J=11.8, 5.7 Hz, 1H), 3.44-3.39 (s, 3H), 2.83-2.62 (m, 2H), 2.16-2.02 (m, 2H). MS(ESI) m/z: [(M+1)⁺, 478.2].

(g) (3S,3aS)-3-(aminomethyl)-7-((R)-4-methoxyl-2-oxopiperidin-1-yl)-3,3a,4-dihydrobenzo[b]oxazolo[3,4-d][1,4]oxazin-1 (3H)-one

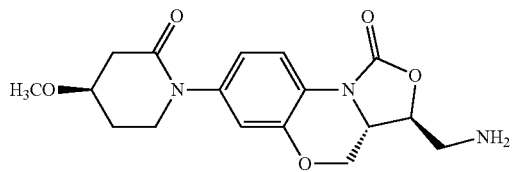 [SMILES: CO[C@@H]1CCN(c2ccc3c(c2)OC[C@H]2[C@H](CN)OC(=O)N32)C(=O)C1]

Using compound 2-(((3S,3aS)-7-((R)-4-methoxyl-2-oxopiperidin-1-yl)-1-oxo-1,3,3a,4-tetrahydrobenzo[b]oxazolo[3,4-d][1,4]oxazin-3-yl)methyl)-isoindolin-1,3-dione (0.79 g, 1.655 mmol), and methylamine alcohol (0.15 g, 4.963 mmol) as starting materials, ethanol as solvent, preparation following the method as described in Example 1 (e) afforded white solid 0.45 g, yield 78.0%.

¹H NMR (400 MHz, CDCl₃) δ 4.54-4.48 (dd, J=10.5, 3.1 Hz, 1H), 4.34-4.27 (q, J=5.8, 5.0 Hz, 1H), 4.10-4.02 (ddd, J=10.0, 6.9, 3.1 Hz, 1H), 3.96-3.87 (t, J=10.3 Hz, 1H), 3.85-3.74 (ddt, J=12.3, 8.5, 4.2 Hz, 2H), 3.22-3.06 (qd, J=13.7, 5.0 Hz, 2H), 2.83-2.61 (m, 2H), 2.19-2.01 (m, 2H). MS(ESI) m/z: [(M+1)⁺, 348.4].

(h) 5-chloro-N-(((3S,3aS)-7-((R)-4-methoxyl-2-oxopiperidin-1-yl)-1-oxo-1,3,3a,4-tetrahydrobenzo[b]oxazolo[3,4-d][1,4]oxazin-3-yl)methyl)-thiophene-2-carboxamide

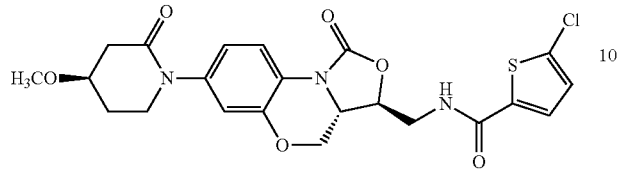

Using compound (3S,3 aS)-3-(aminomethyl)-7-((R)-4-methoxyl-2-oxopiperidin-1-yl)-3,3a,4-dihydrobenzo[b]oxazolo[3,4-d][1,4]oxazin-1 (3H)-one (0.45 g, 1.295 mmol), 5-chlorothiophene-2-carboxylic acid (0.32 g, 1.943 mmol), HATU (0.98 g, 2.590 mmol), and Et$_3$N (0.39 g, 3.885 mmol) as starting materials, DCM as solvent, preparation following the method as described in Example 11 (g) afforded white solid 0.43 g, yield 67.8%.

$^1$H NMR (400 MHz, CDCl$_3$) δ 8.03-7.87 (d, J=9.3 Hz, 1H), 7.63-7.50 (t, J=6.1 Hz, 1H), 7.44-7.36 (d, J=4.1 Hz, 1H), 6.97-6.78 (m, 3H), 4.51-4.30 (m, 2H), 4.05-3.89 (ddd, J=10.2, 7.2, 3.1 Hz, 1H), 3.84-3.66 (m, 5H), 3.57-3.45 (dt, J=11.8, 5.5 Hz, 1H), 3.44-3.38 (s, 3H), 2.89-2.53 (m, 2H), 2.23-1.95 (m, 2H). MS(ESI) m/z: [(M+1)$^+$, 492.4].

Example 13

Preparation of 5-chloro-N-(((3S,3aS)-7-((S)-4-methoxyl-2-oxopiperidin-1-yl)-1-oxo-1,3,3a,4-tetrahydrobenzo[b]oxazolo[3,4-d][1,4]oxazin-3-yl)methyl)-thiophene-2-carboxamide (compound 13)

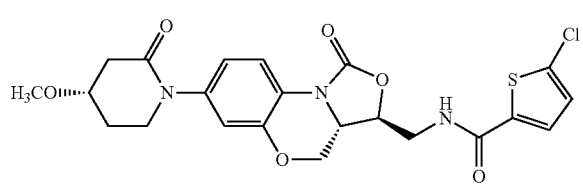 [SMILES: CO[C@H]1CCN(c2ccc3c(c2)OC[C@H]2[C@H](CNC(=O)c4ccc(Cl)s4)OC(=O)N32)C(=O)C1]

Using compound (S) 4-cyano-3-methoxyl butyric acid ethyl ester as starting materials, preparation following the method as described in Example 12 afforded compound 5-chloro-N-(((3S,3aS)-7-((S)-4-methoxyl-2-oxopiperidin-1-yl)-1-oxo-1,3,3a,4-tetrahydrobenzo[b]oxazolo[3,4-d][1,4]oxazin-3-yl)methyl)-thiophene-2-carboxamide.

$^1$H NMR (400 MHz, CDCl$_3$) δ 8.22-7.86 (d, J=8.8 Hz, 1H), 7.58-7.45 (s, 1H), 7.44-7.35 (s, 1H), 7.00-6.68 (m, 3H), 4.50-4.35 (t, J=11.8 Hz, 2H), 4.04-3.94 (s, 1H), 3.88-3.69 (m, 5H), 3.46-3.38 (s, 3H), 2.88-2.56 (m, 2H), 2.23-2.09 (d, J=6.7 Hz, 2H). MS(ESI) m/z: [(M+1)+, 492.4].

Example 14

Preparation of 5-chloro-N-(((3S,3aS)-1-oxo-7-(2-oxooxazol-3-yl)-1,3,3a,4-tetrahydrobenzo[b]oxazolo[3,4-d][1,4]oxazin-3-yl)methyl)thiophene-2-carboxamide (compound 14)

(a) (3R,3aS)-3-((t-butyldimethylsiloxy)methyl)-7-(2-oxooxazol-3-yl)-3a,4-dihydrobenzo[b]oxazolo[3,4-d][1,4]oxazin-1 (3H)-one

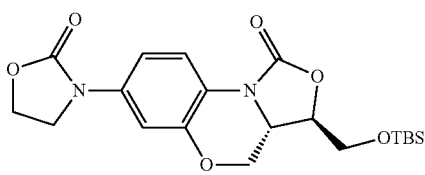 [SMILES: CC(C)(C)[Si](C)(C)OC[C@@H]1OC(=O)N2c3ccc(N4CCOC4=O)cc3OC[C@@H]12]

Using compound A (the same as compound A in Example 1) (0.53 g, 1.276 mmol), oxazol-2-one (0.20 g, 2.297 mmol), Pd$_2$(dba)$_3$ (0.06 g, 0.0638 mmol), Xantphos (0.06 g, 0.1021 mmol), and cesium carbonate (0.83 g, 2.552 mmol) as starting materials, dioxane as solvent, preparation following the method as described in Example 1(a) afforded pale yellow solid 0.41 g, yield 80.8%.

$^1$H NMR (400 MHz, CDCl$_3$) δ 8.03-7.90 (d, J=8.9 Hz, 1H), 7.47-7.34 (d, J=2.5 Hz, 1H), 7.12-6.91 (dd, J=8.9, 2.6 Hz, 1H), 4.55-4.40 (m, 3H), 4.38-4.28 (ddd, J=6.5, 5.6, 4.0 Hz, 1H), 4.15-4.08 (ddd, J=9.9, 6.5, 3.2 Hz, 1H), 4.09-3.99 (m, 2H), 3.99-3.88 (m, 3H), 1.02-0.83 (s, 9H), 0.29-0.02 (d, J=2.8 Hz, 6H). MS(EI) m/z: (M$^+$, 420).

(b) (3R,3 aS)-3-(hydroxymethyl)-7-(2-oxooxazol-3-yl)-3a,4-dihydrobenzo[b]oxazolo[3,4-d][1,4]oxazin-1 (3H)-one

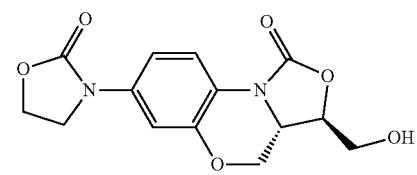 [SMILES: O=C1OCCN1c1ccc2c(c1)OC[C@H]1[C@H](CO)OC(=O)N21]

Using compound (3R,3aS)-3-((t-butyldimethylsiloxy)methyl)-7-(2-oxooxazol-3-yl)-3a,4-dihydrobenzo[b]oxazolo[3,4-d][1,4]oxazin-1(3H)-one (0.38 g, 0.904 mmol), and TBAF (0.47 g, 1.807 mmol) as starting materials, THF as solvent, preparation following the method as described in Example 1(b) afforded white solid 0.29 g, yield 99.9%.

$^1$H NMR (500 MHz, DMSO-d$_6$) δ7.89-7.72 (d, J=8.9 Hz, 1H), 7.37-7.22 (d, J=2.5 Hz, 1H), 7.19-7.08 (dd, J=9.0, 2.5 Hz, 1H), 5.38-5.25 (s, 1H), 4.61-4.50 (m, 1H), 4.50-4.35 (m, 3H), 4.15-3.93 (m, 4H), 3.85-3.59 (m, 2H). MS(EI) m/z: (M$^+$, 306).

(c) ((3R,3aS)-1-oxo-7-(2-oxooxazol-3-yl)-1,3,3a,4-tetrahydrobenzo[b]oxazolo[3,4-d][1,4]oxazin-3-yl)methylmethanesulfonate

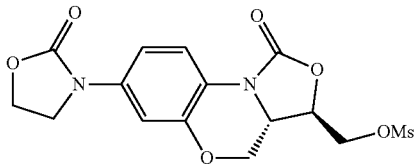 [SMILES: CS(=O)(=O)OC[C@@H]1OC(=O)N2c3ccc(N4CCOC4=O)cc3OC[C@@H]12]

Using compound (3R,3aS)-3-(hydroxymethyl)-7-(2-oxooxazol-3-yl)-3a,4-dihydrobenzo[b]oxazolo[3,4-d][1,4]oxazin-1 (3H)-one (0.29 g, 0.947 mmol), MSCl (0.16 g, 1.420 mmol), and Et$_3$N (0.19 g, 1.894 mmol) as starting materials, preparation following the method as described in Example 1(c) afforded white solid 0.36 g, yield: 98.9%.

$^1$H NMR (400 MHz, DMSO-d$_6$) δ 7.88-7.76 (d, J=8.9 Hz, 1H), 7.37-7.28 (d, J=2.5 Hz, 1H), 7.22-7.10 (dd, J=8.9, 2.6 Hz, 1H), 4.88-4.71 (d, J=2.8 Hz, 1H), 4.69-4.52 (m; 3H), 4.52-4.36 (t, J=8.0 Hz, 2H), 4.17-3.96 (m, 4H), 3.39-3.33 (s, 3H). MS(EI) m/z: (M$^+$, 384).

(d) 2-(((3S,3 aS)-1-oxo-7-(2-oxooxazol-3-yl)-1,3,3a,4-tetrahydrobenzo[1)]oxazolo[3,4-d][1,4]oxazin-3-yl)methyl)isoindolin-1,3-dione

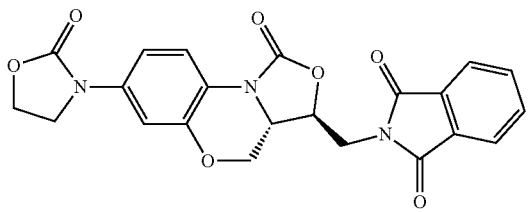 [SMILES: O=C1c2ccccc2C(=O)N1C[C@@H]1OC(=O)N2c3ccc(N4CCOC4=O)cc3OC[C@@H]12]

Using compound ((3R,3 aS)-1-oxo-7-(2-oxooxazol-3-yl)-1,3,3a,4-tetrahydrobenzo[b]oxazolo[3,4-d][1,4]oxazin-3-yl)methylmethanesulfonate (0.36 g, 0.947 mmol), phthalimide potassium (0.26 g, 185.22 mmol) as starting materials, DMF as solvent, preparation following the method as described in Example 1(d) afforded white solid 0.26 g, yield 63.8%.

$^1$H NMR (400 MHz, DMSO-d$_6$) δ8.05-7.85 (m, 4H), 7.83-7.73 (d, J=9.0 Hz, 1H), 7.35-7.24 (s, 1H), 7.20-7.08 (d, J=8.8 Hz, 1H), 4.79-4.59 (m, 2H), 4.51-4.36 (t, J=7.9 Hz, 2H), 4.24-3.92 (m, 6H). MS(EI) m/z (M$^+$, 435).

(e) (3S,3 aS)-3-(aminomethyl)-7-(2-oxooxazol-3-yl)-3a,4-dihydrobenzo[b]oxazolo[3,4-d][1,4]oxazin-1 (3H)-one

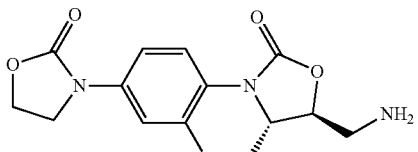

Using compound 2-(((3S,3aS)-1-oxo-7-(2-oxooxazol-3-yl)-1,3,3a,4-tetrahydrobenzo[b]oxazolo[3,4-d][1,4]oxazin-3-yl)methyl)isoindolin-1,3-dione (0.26 g, 0.586 mmol), and methylamine alcohol (0.15 g, 4.686 mmol) as starting materials, ethanol as solvent, preparation following the method as described in Example 1(e) afforded a crude product, which was directly subjected to the next step of reaction without purification.

(f) 5-chloro-N-(((3S,3aS)-1-oxo-7-(2-oxooxazol-3-yl)-1,3,3a,4-tetrahydrobenzo[b]oxazolo[3,4-d][1,4]oxazin-3-yl)methyl)thiophene-2-carboxamide

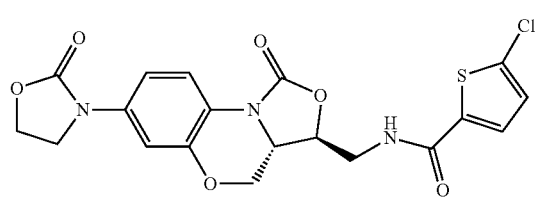 [SMILES: O=C(NC[C@@H]1OC(=O)N2c3ccc(N4CCOC4=O)cc3OC[C@@H]12)c1ccc(Cl)s1]

Using compound (3S,3aS)-3-(aminomethyl)-7-(2-oxooxazol-3-yl)-3a,4-dihydrobenzo[b]oxazolo[3,4-d][1,4]oxazin-1 (3H)-one, 5-chlorothiophene-2-carboxylic acid (0.12 g, 0.737 mmol), HATU (0.38 g, 0.982 mmol), and Et$_3$N (0.15 g, 1.473 mmol) as starting materials, DCM (10 ml) and DMF (2 ml) as a mixed solvent, preparation following the method as described in Example 11 (g) afforded white solid 0.17 g, yield 76.9%.

$^1$H NMR (400 MHz, DMSO-d$_6$) δ9.21-8.83 (t, J=5.8 Hz, 1H), 7.95-7.78 (d, J=8.9 Hz, 1H), 7.77-7.63 (d, J=4.2 Hz, 1H), 7.31-7.26 (d, J=2.5 Hz, 1H), 7.24-7.20 (d, J=4.1 Hz, 1H), 7.18-7.11 (dd, J=8.9, 2.6 Hz, 1H), 4.65-4.51 (m, 2H), 4.48-4.37 (t, J=8.0 Hz, 2H), 4.13-3.96 (m, 4H), 3.78-3.68 (d, J=5.7 Hz, 2H). MS(EI) m/z: (M$^+$, 449).

Example 15

Preparation of 2-((2-chloroethyl)thio)-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)acetamide (compound 15)

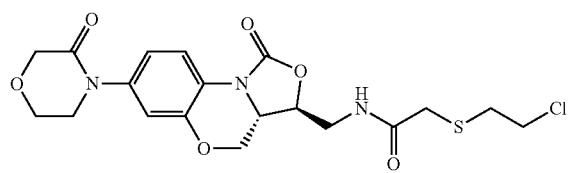 [SMILES: O=C(CSCCCl)NC[C@@H]1OC(=O)N2c3ccc(N4CCOCC4=O)cc3OC[C@@H]12]

Using compound 2-((2-chloroethyl)thio) acetic acid (58 mg, 0.377 mmol), compound (3S,3aS)-3-aminomethyl-7-(3-oxomorpholin-4-yl)-3a,4-dihydrobenzo[b]oxazolo[3,4-d][1,4]oxazin-1 (3H)-one (the product of step (e) in Example 1) (80 mg, 0.251 mmol), TEA (76.2 mg, 0.753 mmol), and HATU (171 mg, 0.452 mmol) as starting materials, preparation following the method as described in Example 11 (g) afforded white solid 70 mg, yield 61.3%.

$^1$H NMR (400 MHz, DMSO-d$_6$) δ 8.56-8.46 (t, J=6.0 Hz, 1H), 7.90-7.82 (d, J=8.8 Hz, 1H), 7.09-7.04 (s, 1H), 7.04-6.98 (d, J=8.3 Hz, 1H), 4.61-4.47 (m, 2H), 4.23-4.13 (s, 2H), 4.08-3.97 (m, 2H), 3.97-3.90 (t, J=5.1 Hz, 2H), 3.82-3.72 (t,

J=7.5 Hz, 2H), 3.71-3.64 (t, J=5.1 Hz, 2H), 3.64-3.52 (qd, J=10.3, 7.2, 5.3 Hz, 2H), 3.27-3.19 (s, 2H), 2.97-2.86 (t, J=7.5 Hz, 2H). MS(EI) m/z: (M⁺, 455).

Example 16

Preparation of 5-chloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)pyridinecarboxamide (compound 16)

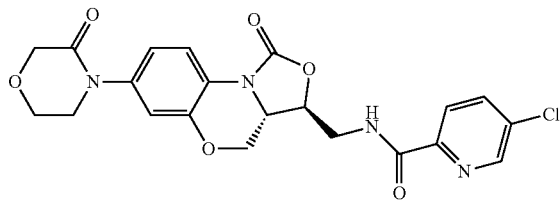 [SMILES: O=C(NC[C@@H]1OC(=O)N2c3ccc(N4CCOCC4=O)cc3OC[C@@H]12)c1ccc(Cl)cn1]

Using compound (3S,3 aS)-3-aminomethyl-7-(3-oxomorpholin-4-yl)-3a,4-dihydrobenzo[b]oxazolo[3,4-d][1,4]oxazin-1 (3H)-one (60 mg, 0.188 mmol) (the product of step (e) in Example 1), 5-chloropyridin-2-carboxylic acid (36 mg, 0.225 mmol), HATU (107 mg, 0.282 mmol), and TEA (38 mg, 0.376 mmol) as starting materials, preparation following the method as described in Example 11 (g) afforded white solid compound 74 mg, yield: 85.85%.

¹H NMR (300 MHz, DMSO-d₆) δ 9.20 (s, 1H), 8.75 (s, 1H), 8.16 (d, J=9.1 Hz, 1H), 8.08 (d, J=8.4 Hz, 1H), 7.85 (d, J=8.7 Hz, 1H), 7.09-6.99 (m, 2H), 4.66 (d, J=5.4 Hz, 1H), 4.52 (d, J=10.2 Hz, 1H), 4.19 (s, 3H), 4.05 (t, J=9.9 Hz, 1H), 3.95 (d, J=4.6 Hz, 2H), 3.79 (s, 2H), 3.70 (s, 2H). MS(EI) m/z: (M⁺, 458).

Example 17

Preparation of 4-chloro-N-(((3S,3aS)-1-oxo-7-(3-oxomorpholin-4-yl)-1,3,3a,4-tetrahydrobenzo[b]oxazolo[3,4-d][1,4]oxazin-3-yl)methyl)benzamide (compound 17)

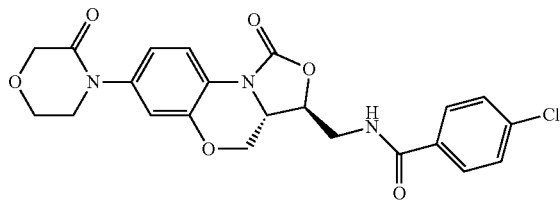 [SMILES: O=C(NC[C@@H]1OC(=O)N2c3ccc(N4CCOCC4=O)cc3OC[C@@H]12)c1ccc(Cl)cc1]

Using compound (3S,3aS)-3-aminomethyl-7-(3-oxomorpholin-4-yl)-3a,4-dihydrobenzo[b]oxazolo[3,4-d][1,4]oxazin-1(3H)-one (the product of step (e) in Example 1) (60 mg, 0.188 mmol), p-chlorobenzoic acid (35 mg, 0.225 mmol), HATU (107 mg, 0.282 mmol), and TEA (38 mg, 0.376 mmol) as starting materials, preparation following the method as described in Example 11 (g) afforded white solid compound 72 mg, yield: 83.68%.

¹H NMR (300 MHz, DMSO-d₆) δ 8.97 (t, J=5.7 Hz, 1H), 7.87 (dd, J=13.0, 8.6 Hz, 3H), 7.56 (d, J=8.6 Hz, 2H), 7.11-6.96 (m, 2H), 4.67-4.52 (m, 2H), 4.17 (s, 2H), 4.08 (dt, J=19.5, 6.2 Hz, 2H), 3.98-3.91 (m, 2H), 3.76 (t, J=5.5 Hz, 2H), 3.72-3.64 (m, 2H). MS(ESI) m/z: [(M+23)⁺, 480.1].

Example 18

Preparation of N¹-(5-chlorothien-2-yl)-N²-(((3S, 3aS)-1-oxo-7-(3-oxomorpholin-4-yl)-1,3,3a,4-tetrahydrobenzo[b]oxazolo[3,4-d][1,4]oxazin-3-yl)methyl)oxamide (compound 18)

(a) 2-(5-chlorothiophene-2-amino)-2-oxalic acid

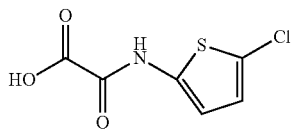 [SMILES: O=C(O)C(=O)Nc1ccc(Cl)s1]

Compound methyl 2-(5-chlorothiophene-2-amino)-2-oxalate (108 mg, 0.492 mmol) was dissolved in 10 ml DCM. 5 ml solution of KOH (42 mg, 0.738 mmol) in methanol was added and stirred at temperature for 2 h. The reaction mixture was acidized by 1N hydrochloric acid, extracted with EA (15 ml×3), dried over anhydrous sodium sulfate, and dried by spinning to afford white solid 82 mg, yield 81.2%.

¹H NMR (400 MHz, DMSO-d₆) δ 12.29 (s, 1H), 6.94 (d, J=4.2 Hz, 1H), 6.84 (d, J=4.2 Hz, 1H). MS(EI) m/z: [M⁺, 205].

(b) N¹-(5-chlorothien-2-yl)-N²-(((3S,3 aS)-1-oxo-7-(3-oxomorpholin-4-yl)-1,3,3a,4-tetrahydrobenzo[b]oxazolo[3,4-d][1,4]oxazin-3-yl)methyl)oxamide

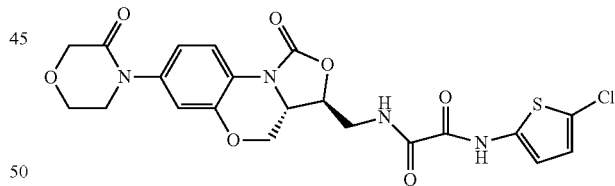

Using compound (3S,3aS)-3-aminomethyl-7-(3-oxomorpholin-4-yl)-3a,4-dihydrobenzo[b]oxazolo[3,4-d][1,4]oxazin-1(3H)-one (the product of step (e) in Example 1) (60 mg, 0.188 mmol), 2-(5-chloro-thiophene-2-amino)-2-oxalic acid (47 mg, 0.225 mmol), HATU (107 mg, 0.282 mmol), and TEA (38 mg, 0.376 mmol) as starting materials, DCM as solvent, preparation following the method as described in Example 11 (g) afforded white solid 71 mg, yield 74.54%.

¹H NMR (300 MHz, DMSO-d₆) δ 12.35 (s, 1H), 9.41 (t, J=6.2 Hz, 1H), 7.84 (d, J=8.7 Hz, 1H), 7.05 (d, J=2.3 Hz, 1H), 7.01 (dd, J=8.7, 2.3 Hz, 1H), 6.95 (d, J=4.2 Hz, 1H), 6.90 (d, J=4.2 Hz, 1H), 4.63-4.52 (m, 2H), 4.18 (s, 2H), 4.16-4.11 (m, 1H), 4.03 (t, J=10.2 Hz, 1H), 3.99-3.89 (m, 2H), 3.75-3.64 (m, 4H). MS(EI) m/z: (M⁺, 506).

Example 19

Preparation of N¹-(5-chloropyridin-2-yl)-N²-(((3S,3aS)-1-oxo-7-(3-oxomorpholin-4-yl)-1,3,3a,4-tetrahydrobenzo[b]oxazolo[3,4-d][1,4]oxazin-3-yl)methyl)oxamide (compound 19)

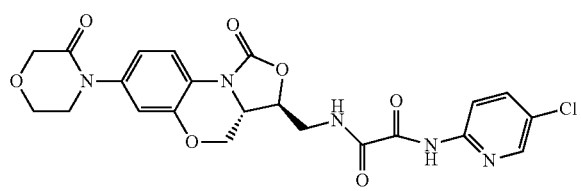 [SMILES: O=C(NC[C@@H]1OC(=O)N2c3ccc(N4CCOCC4=O)cc3OC[C@@H]12)C(=O)Nc1ccc(Cl)cn1]

Using compound (3S,3aS)-3-aminomethyl-7-(3-oxomorpholin-4-yl)-3a,4-dihydrobenzo[b]oxazolo[3,4-d][1,4]oxazin-1(3H)-one (the product of step (e) in Example 1) (60 mg, 0.188 mmol), 2-(5-chloropyridin-2-amino)-2-oxalic acid (45 mg, 0.225 mmol), HATU (107 mg, 0.282 mmol), and TEA (38 mg, 0.376 mmol) as starting materials, DCM as solvent, preparation following the method as described in Example 11 (g) afforded white solid 76 mg, yield 80.59%.

¹H NMR (300 MHz, DMSO-d₆) δ 10.37 (s, 1H), 9.46 (t, J=6.1 Hz, 1H), 8.53-8.44 (m, 1H), 8.14-7.98 (m, 2H), 7.86 (dd, J=6.0, 4.3 Hz, 1H), 7.12-6.97 (m, 2H), 4.67-4.54 (m, 2H), 4.22-4.11 (m, 3H), 4.10-3.99 (m, 2H), 3.96 (dd, J=5.9, 4.2 Hz, 2H), 3.71 (dd, J=11.2, 7.5 Hz, 4H). MS(ESI) m/z: [(M−1)⁺, 499.9].

Example 20

Preparation of N¹-(4-chlorophenyl)-N²-(((3S,3aS)-1-oxo-7-(3-oxomorpholin-4-yl)-1,3,3a,4-tetrahydrobenzo[b]oxazolo[3,4-d][1,4]oxazin-3-yl)methyl)oxamide (compound 20)

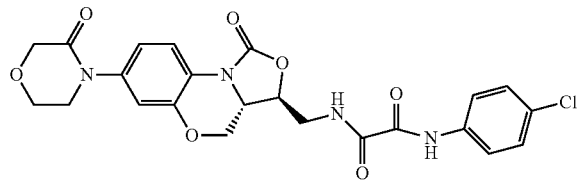 [SMILES: O=C(NC[C@@H]1OC(=O)N2c3ccc(N4CCOCC4=O)cc3OC[C@@H]12)C(=O)Nc1ccc(Cl)cc1]

Using compound (3S,3aS)-3-aminomethyl-7-(3-oxomorpholin-4-yl)-3a,4-dihydrobenzo[b]oxazolo[3,4-d][1,4]oxazin-1(3H)-one (the product of step (e) in Example 1) (60 mg, 0.188 mmol), 2-(4-chlorobenzylamino)-2-oxalic acid (45 mg, 0.225 mmol), HATU (107 mg, 0.282 mmol), and TEA (38 mg, 0.376 mmol) as starting materials, DCM as solvent, preparation following the method as described in Example 11 (g) afforded white solid 68 mg, yield 72.26%.

¹H NMR (300 MHz, DMSO-d₆) δ 10.88 (s, 1H), 9.34 (s, 1H), 7.93-7.83 (m, 3H), 7.44 (d, J=8.7 Hz, 2H), 7.10-7.00 (m, 2H), 4.60 (dd, J=14.2, 8.4 Hz, 2H), 4.19 (s, 3H), 4.11-3.91 (m, 3H), 3.70 (t, J=5.1 Hz, 4H). MS(ESI) m/z: [(M+1)⁺, 501.2].

Example 21

Preparation of 1-(5-chlorothien-2-yl)-3-(((3S,3aS)-1-oxo-7-(3-oxomorpholin-4-yl)-1,3,3a,4-tetrahydrobenzo[b]oxazolo[3,4-d][1,4]oxazin-3-yl)methyl)urea (compound 21)

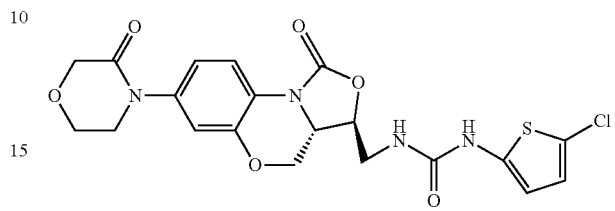

Compound (3S,3aS)-3-aminomethyl-7-(3-oxomorpholin-4-yl)-3a,4-dihydrobenzo[b]oxazolo[3,4-d][1,4]oxazin-1(3H)-one (the product of step (e) in Example 1) (98 mg, 0.307 mmol) was dissolved in 10 ml DCM. TEA (46 mg, 0.45 mmol) was added and the reaction mixture was flushed with Ar. 2-chloro-5-thienylisocyanate (58.8 mg, 0.368 mmol) was added on ice bath, and the resulting mixture was agitated at room temperature overnight. TLC (DCM/MeOH=10/1) was employed to monitor the reaction. After the reaction completed, low boiling point solvent was evaporated under reduced pressure. Column chromatography (DCM/MeOH=100/1) afforded 87 mg white solid, yield: 59.2%.

¹H NMR (400 MHz, DMSO-d₆) δ 9.83 (s, 1H), 7.85 (d, J=8.7 Hz, 1H), 7.08-6.99 (m, 2H), 6.81-6.73 (m, 2H), 6.25 (d, J=4.1 Hz, 1H), 4.54 (dd, J=12.1, 6.2 Hz, 2H), 4.17 (s, 2H), 4.08-3.98 (m, 2H), 3.97-3.91 (m, 2H), 3.72-3.65 (m, 2H), 3.58 (t, J=5.4 Hz, 2H). MS(ESI) m/z: [(M+23)⁺, 501.3].

Example 22

Preparation of 1-(4-chlorophenyl)-3-(((3S,3aS)-1-oxo-7-(3-oxomorpholin-4-yl)-1,3,3a,4-tetrahydrobenzo[b]oxazolo[3,4-d][1,4]oxazin-3-yl)methyl)urea (compound 22)

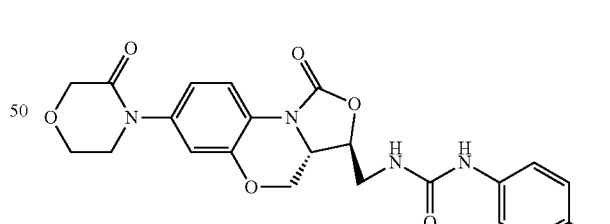

Using compound (3S,3aS)-3-aminomethyl-7-(3-oxomorpholin-4-yl)-3a,4-dihydrobenzo[b]oxazolo[3,4-d][1,4]oxazin-1(3H)-one (the product of step (e) in Example 1) (60 mg, 0.188 mmol), p-chlorophenylisocyanate (35 mg, 0.225 mmol), and TEA (28 mg, 0.282 mmol) as starting materials, DCM as solvent, preparation following the method as described in Example 21 afforded white compound 75 mg, yield 84.4%.

¹H NMR (300 MHz, DMSO-d₆) δ 8.75 (s, 1H), 7.84 (d, J=8.6 Hz, 1H), 7.44-7.37 (m, 2H), 7.29-7.21 (m, 2H), 7.06-

6.96 (m, 2H), 6.58 (s, 1H), 4.55 (d, J=7.2 Hz, 2H), 4.16 (s, 2H), 4.06-3.98 (m, 2H), 3.96-3.89 (m, 2H), 3.70-3.62 (m, 2H), 3.57 (s, 2H). MS(ESI) m/z: [(M+23)⁺, 495.3].

Example 23

Preparation of 5-chloro-N-(((3S,3aS)-1-oxo-7-(2-oxopiperazin-1-yl)-1,3,3a,4-tetrahydrobenzo[b]oxazolo[3,4-d][1,4]oxazin-3-yl)methyl)thiophene-2-carboxamide (compound 23)

(a) 4-((3R,3aS)-3-((t-butyldimethylsilyl)oxy)methyl)-1-oxo-1,3,3a,4-tetrahydrobenzo[b]oxazolo[3,4-d][1,4]oxazin-7-yl)-3-oxopiperazin-1-carboxylic acid benzyl ester

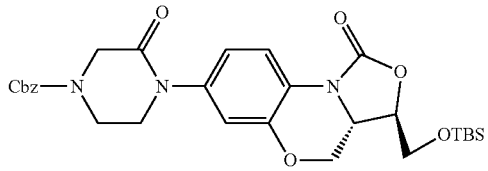 [SMILES: CC(C)(C)[Si](C)(C)OC[C@@H]1OC(=O)N2c3ccc(N4CCN(C(=O)OCc5ccccc5)CC4=O)cc3OC[C@@H]12]

Using compound A (the same as in Example 1) (2 g, 4.83 mmol), 3-oxopiperazin carboxylic acid benzyl ester (1.7 g, 7.25 mmol), cesium carbonate (3.935 g, 0.012 mol), Pd₂(dba)₃ (0.31 g, 0.338 mmol), and Xantphos (0.28 g, 0.483 mmol) as starting materials, preparation following the method as described in Example 1 (a) afforded white solid 1.049 g, yield: 38.2%.

¹H NMR (400 MHz, CDCl₃) δ 8.03 (d, J=8.7 Hz, 1H), 7.41-7.32 (m, 5H), 6.94-6.86 (m, 2H), 5.19 (s, 2H), 4.46 (dd, J=10.5, 3.2 Hz, 1H), 4.32 (s, 2H), 4.28 (dd, J=11.2, 4.8 Hz, 1H), 4.11 (s, 1H), 3.91 (dd, J=8.2, 3.0 Hz, 3H), 3.88-3.82 (m, 2H), 3.71 (s, 2H), 0.89 (s, 9H), 0.11 (d, J=2.6 Hz, 6H). MS(EI) m/z: (M⁺, 567).

(b) 4-((3R,3aS)-3-(hydroxymethyl)-1-oxo-1,3,3a,4-tetrahydrobenzo[b]oxazolo[3,4-d][1,4]oxazin-7-yl)-3-oxopiperazin-1-carboxylic acid benzyl ester

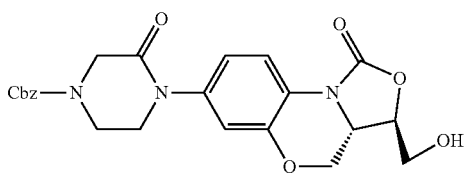 [SMILES: O=C(OCc1ccccc1)N1CCN(c2ccc3c(c2)OC[C@H]2[C@H](CO)OC(=O)N32)C(=O)C1]

Using compound 4-((3R,3aS)-3-((t-butyldimethylsilyl)oxy)methyl)-1-oxo-1,3,3a,4-tetrahydrobenzo[b]oxazolo[3,4-d][1,4]oxazin-7-yl)-3-oxopiperazin-1-carboxylic acid benzyl ester (1.049 g, 1.85 mmol), tetra-n-butylammonium fluoride (1M, 3.7 ml) as starting materials, preparation following the method as described in Example 1 (b) afforded 0.81 g white solid, yield: 96.68%.

¹H NMR (400 MHz, CDCl₃) δ 8.03 (d, J=8.7 Hz, 1H), 7.42-7.30 (m, 5H), 6.92 (d, J=2.2 Hz, 1H), 6.88 (dd, J=8.7, 2.3 Hz, 1H), 5.19 (s, 2H), 4.47 (dd, J=10.6, 3.2 Hz, 1H), 4.34-4.28 (m, 3H), 4.14 (ddd, J=10.1, 7.0, 3.2 Hz, 1H), 3.95 (dd, J=12.3, 4.3 Hz, 1H), 3.85 (ddd, J=16.2, 13.6, 7.2 Hz, 4H), 3.71 (s, 2H). MS(EI) m/z: (M+, 453).

(c) 4-((3R,3aS)-3-((methylsulfonyloxy)methyl)-1-oxo-1,3,3a,4-tetrahydrobenzo[b]oxazolo[3,4-d][1,4]oxazin-7-yl)-3-oxopiperazin-1-carboxylic acid benzyl ester

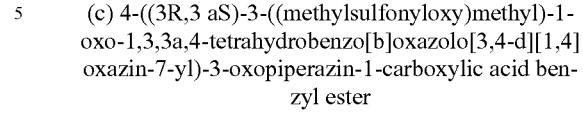

Using compound 4-((3R,3aS)-3-(hydroxymethyl)-1-oxo-1,3,3a,4-tetrahydrobenzo[b]oxazolo[3,4-d][1,4]oxazin-7-yl)-3-oxopiperazin-1-carboxylic acid benzyl ester (0.946 g, 2.088 mmol), methylsulfonyl chloride (0.359 g, 3.13 mmol), and TEA (0.422 g, 4.18 mmol) as starting materials, preparation following the method as described in Example 1 (c) afforded white solid 0.916 g, yield: 82.52%.

¹H NMR (400 MHz, CDCl₃) δ 8.03 (d, J=8.8 Hz, 1H), 7.42-7.30 (m, 5H), 6.91 (d, J=2.2 Hz, 1H), 6.87 (dd, J=8.8, 2.2 Hz, 1H), 5.19 (s, 2H), 4.47 (dd, J=10.6, 3.2 Hz, 1H), 4.34-4.28 (m, 3H), 4.14 (ddd, J=10.1, 7.0, 3.2 Hz, 1H), 3.95 (dd, J=12.3, 4.3 Hz, 1H), 3.90 (ddd, J=16.2, 13.6, 7.2 Hz, 4H), 3.73 (s, 2H), 3.28 (s, 3H). MS(EI) m/z: (M+, 531).

(d) 4-((3S,3aS)-3-((1,3-dioxo-isoindolin-2-yl)methyl)-1-oxo-1,3,3a,4-tetrahydrobenzo[b]oxazolo[3,4-d][1,4]oxazin-7-yl)-3-oxopiperazin-1-carboxylic acid benzyl ester

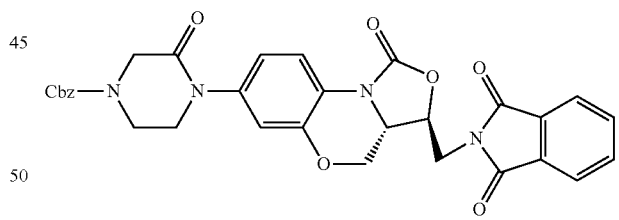

Using compound 4-((3R,3aS)-3-((methylsulfonyloxy)methyl)-1-oxo-1,3,3a,4-tetrahydrobenzo[b]oxazolo[3,4-d][1,4]oxazin-7-yl)-3-oxopiperazin-1-carboxylic acid benzyl ester (0.916 g, 1.725 mmol), and phthalimide potassium (0.479 g, 2.558 mmol) as starting materials, preparation following the method as described in Example 1 (d) afforded white solid 0.794 g, yield: 79.1%.

¹H NMR (400 MHz, CDCl₃) δ 8.00 (d, J=8.6 Hz, 1H), 7.90 (dd, J=5.3, 3.1 Hz, 2H), 7.78 (dd, J=5.5, 3.1 Hz, 2H), 7.42-7.32 (m, 5H), 6.95-6.86 (m, 2H), 5.18 (s, 2H), 4.64 (dd, J=12.2, 6.6 Hz, 1H), 4.47 (dd, J=10.6, 3.1 Hz, 1H), 4.31 (s, 2H), 4.23 (dd, J=14.3, 6.8 Hz, 1H), 4.06 (ddd, J=11.7, 8.7, 4.3 Hz, 2H), 3.92-3.81 (m, 3H), 3.70 (s, 2H). MS(EI) m/z: (M⁺, 582).

(e) 4-((3S,3aS)-3-(aminomethyl)-1-oxo-1,3,3a,4-tetrahydrobenzo[b]oxazolo[3,4-d][1,4]oxazin-7-yl)-3-oxopiperazin-1-carboxylic acid benzyl ester

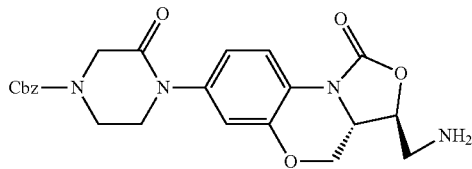 [SMILES: NC[C@@H]1OC(=O)N2c3ccc(N4CCN(C(=O)OCc5ccccc5)CC4=O)cc3OC[C@@H]12]

Using compound 4-((3S,3aS)-3-(0,3-dioxo-isoindolin-2-yl)methyl)-1-oxo-1,3,3a,4-tetrahydrobenzo[b]oxazolo[3,4-d][1,4]oxazin-7-yl)-3-oxopiperazin-1-carboxylic acid benzyl ester (0.729 g, 1.25 mmol), and 21 ml of methylamine alcohol solution as starting materials, preparation following the method as described in Example 1 (e) afforded a crude product, which was directly subjected to the next step of reaction without purification.

(f) 4-((3S,3aS)-3-((5-chlorothiophene-2-formamido)methyl)-1-oxo-1,3,3a,4-tetrahydrobenzo[b]oxazolo[3,4-d][1,4]oxazin-7-yl)-3-oxopiperazin-1-carboxylic acid benzyl ester

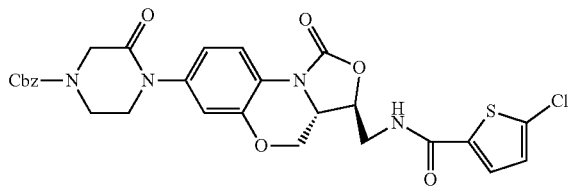 [SMILES: O=C(NC[C@@H]1OC(=O)N2c3ccc(N4CCN(C(=O)OCc5ccccc5)CC4=O)cc3OC[C@@H]12)c1ccc(Cl)s1]

Using the crude 4-((3S,3aS)-3-(aminomethyl)-1-oxo-1,3,3a,4-tetrahydrobenzo[b]oxazolo[3,4-d][1,4]oxazin-7-yl)-3-oxopiperazin-1-carboxylic acid benzyl ester prepared above, 5-chlorothiophene-2-formyl chloride (0.2 g, 1.1 mmol), and TEA (0.186 g, 1.84 mmol) as starting materials, preparation following the method as described in Example 1 (f) afforded white compound 0.44 g, two step yield: 58.9%.

$^1$H NMR (400 MHz, CDCl$_3$) δ 7.99 (d, J=8.7 Hz, 1H), 7.40-7.32 (m, 6H), 6.92-6.85 (m, 3H), 6.77 (s, 1H), 5.18 (s, 2H), 4.53 (dd, J=10.5, 3.1 Hz, 1H), 4.50-4.42 (m, 1H), 4.31 (s, 2H), 4.02-3.93 (m, 1H), 3.90-3.78 (m, 5H), 3.70 (s, 2H). MS(ESI) m/z: (M$^+$, 597).

(g) 5-chloro-N-(((3S,3aS)-1-oxo-7-(2-oxopiperazin-1-yl)-1,3,3a,4-tetrahydrobenzo[b]oxazolo[3,4-d][1,4]oxazin-3-yl)methyl)thiophene-2-carboxamide

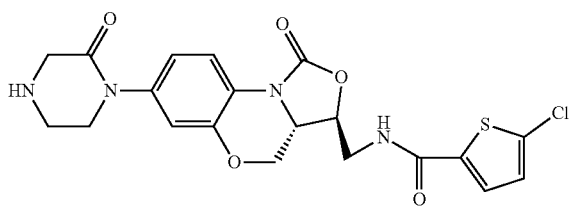 [SMILES: O=C(NC[C@@H]1OC(=O)N2c3ccc(N4CCNCC4=O)cc3OC[C@@H]12)c1ccc(Cl)s1]

Compound 4-((3S,3aS)-3-((5-chlorothiophene-2-formamido)methyl)-1-oxo-1,3,3a,4-tetrahydrobenzo[b]oxazolo[3,4-d][1,4]oxazin-7-yl)-3-oxopiperazin-1-carboxylic acid benzyl ester (0.86 g, 1.45 mmol) was dissolved in 20 ml DCM and cooled on ice bath. 6.5 ml of dimethyl sulfide was added, and boron trifluoride etherate solution (1.84 ml, 14.47 mmol) was added dropwise. TLC (DCM/MeOH=10/1) was employed to monitor the reaction. After the reaction completed, the layers were separated by adding water (20 ml) and the aqueous phase was extracted with DCM (10 ml×3). The organic phase was combined, dried over anhydrous sodium sulfate, filtered under reduced pressure, and the solvent was evaporated. Column chromatography (DCM/MeOH=30/1) afforded 0.55 g white solid, yield 82.6%.

$^1$H NMR (400 MHz, DMSO-d$_6$) δ 9.00 (t, J=5.7 Hz, 1H), 7.83 (d, J=8.4 Hz, 1H), 7.71 (d, J=4.1 Hz, 1H), 7.21 (d, J=4.1 Hz, 1H), 6.99-6.91 (m, 2H), 5.76 (s, 1H), 4.65-4.50 (m, 2H), 4.13-3.98 (m, 2H), 3.72 (t, J=5.5 Hz, 2H), 3.55 (t, J=5.7 Hz, 2H), 3.37 (s, 2H), 3.00 (t, J=5.4 Hz, 2H). MS(ESI) m/z: [(M+1)$^+$, 463.3].

Example 24

Preparation of 5-chloro-N-(((3S,3aS)-7-(4-methyl-2-oxopiperazin-1-yl)-1-oxo-1,3,3a,4-tetrahydrobenzo[b]oxazolo[3,4-d][1,4]oxazin-3-yl)methyl)thiophene-2-carboxamide (compound 24)

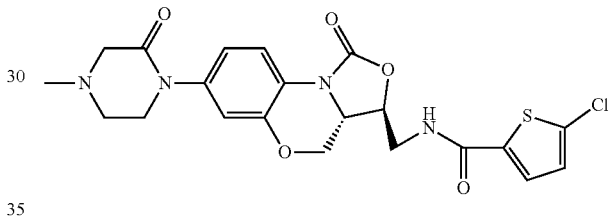

Compound 22 (78 mg, 0.168 mmol) was dissolved in 10 ml of methanol. 37% aqueous solution of formaldehyde (21 mg, 0.253 mmol) and sodium triacetoxyborohydride (0.143 g, 0.674 mmol) were added. TLC (DCM/MeOH=10/1) was employed to monitor the reaction. After the reaction completed, 10 ml of water was added, and the resulting mixture was extracted with EA (10 ml×3). The organic phase was combined, dried over anhydrous sodium sulfate, and the solvent was evaporated. Column chromatography (DCM/MeOH=30/1) afforded 56 g white solid, yield 69.8%.

$^1$H NMR (400 MHz, CDCl$_3$) δ 7.99 (d, J=8.6 Hz, 1H), 7.34 (d, J=4.0 Hz, 1H), 6.90 (dd, J=6.2, 4.0 Hz, 3H), 6.79 (t, J=6.1 Hz, 1H), 4.49 (ddd, J=16.7, 10.4, 4.5 Hz, 2H), 4.04-3.94 (m, 1H), 3.92-3.74 (m, 3H), 3.69 (s, 2H), 3.31 (s, 2H), 2.84 (s, 2H), 2.44 (s, 3H) MS(EI) m/z: (M$^+$, 476).

Example 25

Preparation of 5-chloro-N-(((3S,3aS)-7-(4-ethyl-2-oxopiperazin-1-yl)-1-oxo-1,3,3a,4-tetrahydrobenzo[b]oxazolo[3,4-d][1,4]oxazin-3-yl)methyl)thiophene-2-carboxamide (compound 25)

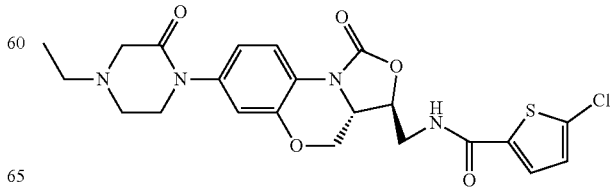

Using compound 22 (40 mg, 0.086 mmol), acetaldehyde (5.7 mg, 0.13 mmo), and sodium triacetoxyborohydride (74 mg, 0.35 mmol), preparation following the method as described in Example 24 afforded 26 mg of white solid, yield 62.3%.

$^1$H NMR (300 MHz, CDCl$_3$) δ 7.97 (d, J=8.8 Hz, 1H), 7.36 (d, J=3.4 Hz, 1H), 7.17 (s, 1H), 6.90 (d, J=6.4 Hz, 3H), 4.45 (dd, J=13.7, 8.2 Hz, 2H), 3.97 (s, 1H), 3.88-3.72 (m, 3H), 3.66 (s, 2H), 3.30 (s, 2H), 2.81 (s, 2H), 2.53 (d, J=7.1 Hz, 2H), 1.14 (t, J=6.9 Hz, 3H). MS(EI) m/z: (M$^+$, 490).

Example 26

Preparation of 5-chloro-N-(((3S,3aS)-1-oxo-7-(2-oxo-4-(phenylsulfonyl) piperazin-1-yl)-1,3,3a,4-tetrahydrobenzo[b]oxazolo[3,4-d][1,4]oxazin-3-yl)methyl)thiophene-2-carboxamide (compound 26)

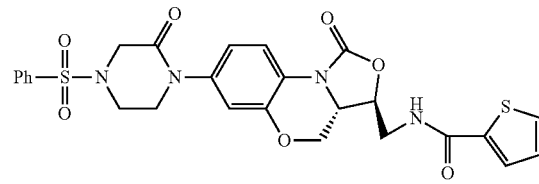

Compound 22 (40 mg, 0.086 mmol) was dissolved in 5 ml of DMF and cooled on ice bath. TEA (16.7 mg, 0.156 mmol) was added and benzenesulfonyl chloride (18.3 mg, 0.104 mmol) was added slowly in dropwise. The ice bath was removed and the mixture was allowed to react for 3 h. TLC (DCM/MeOH=10/1) was employed to monitor the reaction. After the reaction completed, 10 ml of water was added, and the mixture was extracted with EA (8 ml×3). The organic phase was combined, dried over anhydrous sodium sulfate, and the solvent was evaporated. Column chromatography (DCM/MeOH=50/1) afforded white solid 30 mg, yield: 57.6%.

$^1$H NMR (300 MHz, DMSO-d$_6$) δ 8.98 (s, 1H), 7.77 (dd, J=27.8, 19.6 Hz, 7H), 7.19 (s, 1H), 6.80 (s, 2H), 4.53 (s, 2H), 4.02 (s, 2H), 3.73 (s, 5H), 3.60 (s, 3H). MS(EI) m/z: (M$^+$, 490).

Example 27

Preparation of 5-chloro-N-(((3S,3aS)-1-oxo-7-(2-oxo-4-(methylsulfonyl) piperazin-1-yl)-1,3,3a,4-tetrahydrobenzo[b]oxazolo[3,4-d][1,4]oxazin-3-yl)methyl)thiophene-2-carboxamide (compound 27)

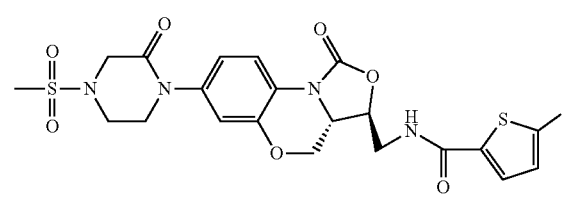

Compound 22 (40 mg, 0.086 mmol) was dissolved in 5 ml of DMF and cooled on ice bath. TEA (16.7 mg, 0.156 mmol) was added, and methylsulfonyl chloride (11.9 mg, 0.104 mmol) was added slowly in dropwise. Preparation following the method as described in Example 26 afforded white solid 40 mg, yield: 85.6%.

$^1$H NMR (400 MHz, DMSO-d$_6$) δ 9.00 (t, J=5.9 Hz, 1H), 7.86 (d, J=8.7 Hz, 1H), 7.71 (d, J=4.1 Hz, 1H), 7.21 (d, J=4.1 Hz, 1H), 7.02 (d, J=2.3 Hz, 1H), 6.98 (dd, J=8.7, 2.3 Hz, 1H), 4.58 (dd, J=15.7, 7.0 Hz, 2H), 4.13-4.01 (m, 2H), 3.93 (s, 2H), 3.73 (q, J=4.9 Hz, 4H), 3.57-3.51 (m, 2H), 3.05 (s, 3H). MS(EI) m/z: (M$^+$, 540).

Example 28

Preparation of N-(((3S,3aS)-7-(4-acetyl-2-oxopiperazin-1-yl) 1-oxo-1,3,3a,4-tetrahydrobenzo[b]oxazolo[3,4-d][1,4]oxazin-3-yl)methyl)5-chlorothiophene-2-carboxamide (compound 28)

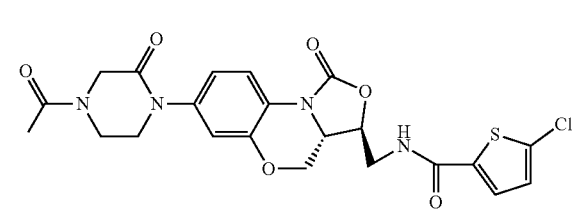 [SMILES: CC(=O)N1CCN(c2ccc3c(c2)OC[C@H]2[C@H](CNC(=O)c4ccc(Cl)s4)OC(=O)N32)C(=O)C1]

Compound 22 (40 mg, 0.086 mmol) was dissolved in 5 ml of DMF. TEA (16.7 mg, 0.156 mmol) and acetyl chloride (18.3 mg, 0.104 mmol) were added. Preparation following the method as described in Example 26 afforded white solid 27 mg, yield: 62%.

$^1$H NMR (400 MHz, CDCl$_3$) δ 7.99 (t, J=9.2 Hz, 1H), 7.35 (d, J=3.8 Hz, 1H), 7.04-6.82 (m, 4H), 4.59-4.44 (m, 2H), 4.34 (d, J=38.9 Hz, 2H), 4.03-3.92 (m, 2H), 3.85 (d, J=10.5 Hz, 4H), 3.71 (dd, J=20.5, 15.1 Hz, 2H), 2.16 (s, 3H). MS(EI) m/z: (M$^+$, 504).

Example 29

Preparation of N-(((3S,3aS)-7-(4-benzyl-2-oxopiperazin-1-yl)1-oxo-1,3,3a,4-tetrahydrobenzo[b]oxazolo[3,4-d][1,4]oxazin-3-yl)methyl)5-chlorothiophene-2-carboxamide (compound 29)

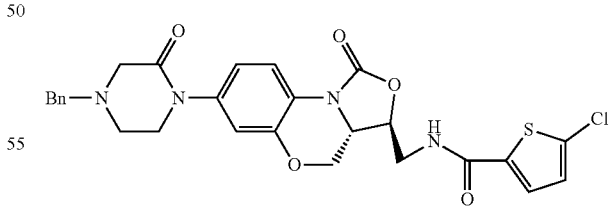

Compound 22 (30 mg, 0.065 mmol) was dissolved in 5 ml of DMF. TEA (13 mg, 0.13 mmol) and benzyl bromide (11.1 mg, 0.065 mmol) were added. Preparation following the method as described in Example 26 afforded white solid 28 mg, yield: 78%.

$^1$H NMR (400 MHz, CDCl$_3$) δ 7.97 (d, J=8.4 Hz, 1H), 7.34 (t, J=4.2 Hz, 5H), 7.32-7.27 (m, 1H), 7.04 (t, J=5.9 Hz, 1H), 6.94-6.83 (m, 3H), 4.45 (ddd, J=17.0, 10.9, 4.3 Hz, 2H), 4.00-3.91 (m, 1H), 3.86-3.69 (m, 3H), 3.63 (d, J=8.7 Hz, 4H), 3.31 (s, 2H), 2.80 (t, J=5.3 Hz, 2H). MS(EI) m/z: (M+, 552).

Example 30

Preparation of 5-chloro-N-(((3S,3aS)-7-(N-methylacetamide)1-oxo-1,3,3a,4-tetrahydrobenzo[b]oxazolo[3,4-d][1,4]oxazin-3-yl)methyl)thiophene-2-carboxamide (compound 30)

(a) N-((3R,3aS)-3-(((t-butyldimethylsilyl)oxy)methyl)-1-oxo-1,3,3a,4-tetrahydrobenzo[b]oxazolo[3,4-d][1,4]oxazin-7-yl)-acetamide

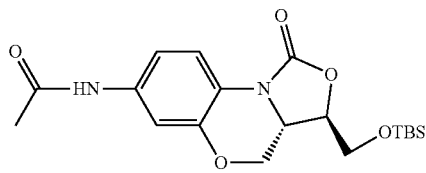 [SMILES: CC(=O)Nc1ccc2c(c1)OC[C@H]1[C@H](CO[Si](C)(C)C(C)(C)C)OC(=O)N21]

Using compound A (the same as in Example 1) (1 g, 2.42 mmol), acetamide (0.214 g, 3.62 mmol), cesium carbonate (1.967 g, 6.04 mmol), Pd$_2$(dba)$_3$ (0.155 g, 0.169 mmol), and Xantphos (0.14 g, 0.242 mmol) as starting materials, preparation following the method as described in Example 1 (a) afforded white solid 0.687 g, yield: 72.56%.

$^1$H NMR (400 MHz, CDCl$_3$) δ 7.88 (d, J=8.7 Hz, 1H), 7.42 (d, J=2.3 Hz, 1H), 7.24 (s, 1H), 6.88 (dd, J=8.8, 2.3 Hz, 1H), 4.44 (dd, J=10.5, 3.2 Hz, 1H), 4.27 (td, J=6.0, 4.1 Hz, 1H), 4.09 (ddd, J=9.8, 6.5, 3.1 Hz, 1H), 3.98-3.83 (m, 3H), 2.16 (s, 3H), 0.89 (d, J=2.9 Hz, 9H), 0.10 (d, J=2.6 Hz, 6H). MS(EI) m/z: (M+, 392).

(b) N-((3R,3aS)-3-(((t-butyldimethylsilyl)oxy)methyl)-1-oxo-1,3,3a,4-tetrahydrobenzo[b]oxazolo[3,4-d][1,4]oxazin-7-yl)-N-methylacetamide

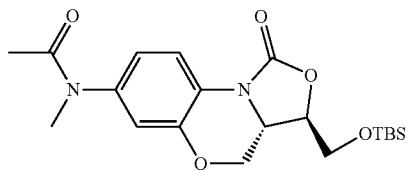 [SMILES: CC(=O)N(C)c1ccc2c(c1)OC[C@H]1[C@H](CO[Si](C)(C)C(C)(C)C)OC(=O)N21]

Compound N-((3R,3aS)-3-(((t-butyldimethylsilyl)oxy)methyl)-1-oxo-1,3,3a,4-tetrahydrobenzo[b]oxazolo[3,4-d][1,4]oxazin-7-yl)-acetamide (0.685 g, 1.747 mmol) was dissolved in 20 ml of THF and cooled on ice-salt bath. 60% NaH (0.14 g, 3.495 mmol) was added. The ice bath was removed, and the reaction mixture was stirred at room temperature for 30 min, and then cooled on ice-salt bath. Iodomethane (0.496 g, 3.495 mmol) was added slowly in dropwise. The ice bath was removed, and the reaction mixture was stirred at room temperature for 3 h. TLC (PE/EA=1/1) was employed to monitor the reaction. After the reaction completed, the reaction was quenched by adding 10 ml of water and then extracted with EA (10 ml×3). The organic phase was combined, dried over anhydrous sodium sulfate, and the solvent was evaporated. Column chromatography (PE/EA=3/1) afforded white solid 0.618 g, yield: 87.11%.

$^1$H NMR (400 MHz, CDCl$_3$) δ 8.02 (d, J=8.5 Hz, 1H), 6.84 (dd, J=8.6, 2.3 Hz, 1H), 6.79 (d, J=2.1 Hz, 1H), 4.49 (dd, J=10.5, 3.2 Hz, 1H), 4.30 (dd, J=10.1, 5.8 Hz, 1H), 4.13 (ddd, J=9.8, 6.5, 3.3 Hz, 1H), 3.98-3.85 (m, 3H), 3.22 (s, 3H), 1.89 (s, 3H), 0.90 (s, 9H), 0.11 (d, J=2.3 Hz, 6H). MS(EI) m/z: (M+, 406).

(c) N-((3R,3aS)-3-(hydroxymethyl)-1-oxo-1,3,3a,4-tetrahydrobenzo[b]oxazolo[3,4-d][1,4]oxazin-7-yl)-N-methylacetamide

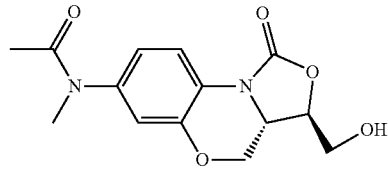 [SMILES: CC(=O)N(C)c1ccc2c(c1)OC[C@H]1[C@H](CO)OC(=O)N21]

Using N-((3R,3aS)-3-(((t-butyldimethylsilyl)oxy)methyl)-1-oxo-1,3,3a,4-tetrahydrobenzo[b]oxazolo[3,4-d][1,4]oxazin-7-yl)-N-methylacetamide (0.617 g, 1.52 mmol), and TBAF (1M, 2 ml) as starting materials, preparation following the method as described in Example 1 (b) afforded white solid 0.384 g, yield: 86.53%.

$^1$H NMR (300 MHz, DMSO-d$_6$) δ 7.87 (d, J=8.5 Hz, 1H), 7.05-6.91 (m, 2H), 5.32 (t, J=5.7 Hz, 1H), 4.62-4.50 (m, 1H), 4.45 (d, J=4.8 Hz, 1H), 4.05 (d, J=5.9 Hz, 2H), 3.82-3.62 (m, 2H), 3.10 (s, 3H), 1.77 (s, 3H). MS(EI) m/z: (M+, 292).

(d) methyl ((3R,3 aS)-7-(N-methylacetamide)-1-oxo-1,3,3a,4-tetrahydrobenzo[b]oxazolo[3,4-d][1,4]oxazin-3-yl) methanesulfonate

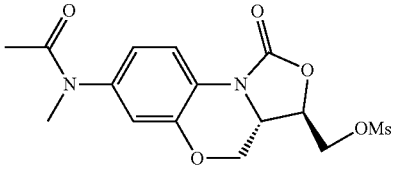 [SMILES: CC(=O)N(C)c1ccc2c(c1)OC[C@H]1[C@H](COS(C)(=O)=O)OC(=O)N21]

Using compound N-((3R,3aS)-3-(hydroxymethyl)-1-oxo-1,3,3a,4-tetrahydrobenzo[b]oxazolo[3,4-d][1,4]oxazin-7-yl)-N-methylacetamide (0.384 g, 1.315 mmol), methylsulfonyl chloride (0.181 g, 1.578 mmol), and TEA (0.266 g, 2.63 mmol) as starting materials, preparation following the method as described in Example 1 (c) afforded white solid 0.45 g, yield 92.48%.

$^1$H NMR (300 MHz, CDCl$_3$) δ 8.01 (d, J=8.6 Hz, 1H), 6.90-6.81 (m, 2H), 4.61-4.53 (m, 4H), 4.16 (s, 1H), 3.95 (t, J=10.3 Hz, 1H), 3.23 (s, 3H), 3.15 (s, 3H), 1.90 (s, 3H). MS(EI) m/z: (M+, 370).

(e) N-((3S,3aS)-3-((1,3-dioxo-isoindolin-2-yl)methyl)-1-oxo-1,3,3a,4-tetrahydrobenzo[b]oxazolo[3,4-d][1,4]oxazin-7-yl)-N-methylacetamide

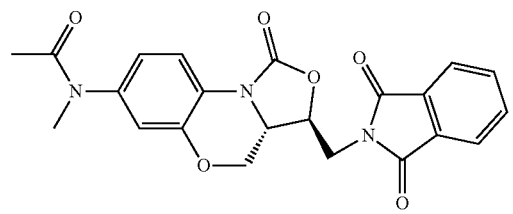 [SMILES: CC(=O)N(C)c1ccc2c(c1)OC[C@H]1[C@H](CN3C(=O)c4ccccc4C3=O)OC(=O)N21]

Using compound methyl ((3R,3 aS)-7-(N-methylacetamide)-1-oxo-1,3,3a,4-tetrahydrobenzo[b]oxazolo[3,4-d][1,4]oxazin-3-yl) methanesulfonate (0.45 g, 1.216 mmol), and phthalimide potassium (0.338 g, 1.824 mmol) as starting materials, preparation following the method as described in Example 1 (d) afforded white solid 0.4 g, yield: 78.13%.

$^1$H NMR (300 MHz, DMSO-d$_6$) δ 7.91 (ddd, J=17.8, 10.0, 7.3 Hz, 5H), 7.09-6.91 (m, 2H), 4.70 (dd, J=18.5, 8.4 Hz, 2H), 4.21 (s, 1H), 4.09 (dd, J=18.0, 7.4 Hz, 3H), 3.11 (s, 3H), 1.79 (s, 3H). MS(EI) m/z: (M+, 421).

(f) N-((3S,3aS)-3-(aminomethyl)-1-oxo-1,3,3a,4-tetrahydrobenzo[b]oxazolo[3,4-d][1,4]oxazin-7-yl)-N-methylacetamide

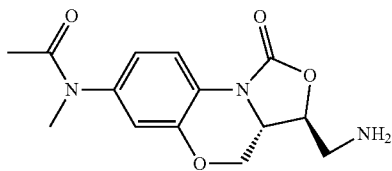 [SMILES: CC(=O)N(C)c1ccc2c(c1)OC[C@H]1[C@H](CN)OC(=O)N21]

Using compound N-((3S,3 aS)-3-((1,3-dioxo-isoindolin-2-yl)methyl)-1-oxo-1,3,3a,4-tetrahydrobenzo[b]oxazolo[3,4-d][1,4]oxazin-7-yl)-N-methylacetamide (0.4 g, 0.95 mmol), and 10 ml of methylamine alcohol solution as starting materials, preparation following the method as described in Example 1 (e) afforded a crude product, which was directly subjected to the next step of reaction.

(g) 5-chloro-N-(((3S,3aS)-7-(N-methylacetamide)1-oxo-1,3,3a,4-tetrahydrobenzo[b]oxazolo[3,4-d][1,4]oxazin-3-yl)methyl)thiophene-2-carboxamide

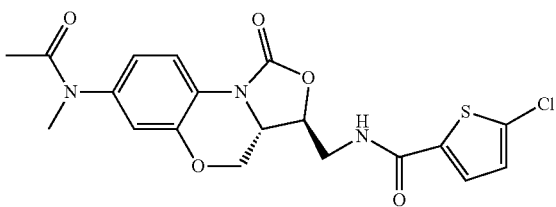 [SMILES: CC(=O)N(C)c1ccc2c(c1)OC[C@H]1[C@H](CNC(=O)c3ccc(Cl)s3)OC(=O)N21]

Using the crude N-((3S,3aS)-3-(aminomethyl)-1-oxo-1,3,3a,4-tetrahydrobenzo[b]oxazolo[3,4-d][1,4]oxazin-7-yl)-N-methylacetamide prepared above and 5-chlorothiophene-2-formyl chloride (0.206 g, 1.14 mmol) as starting materials, preparation following the method as described in Example 1 (f) afforded compound 0.316 g, yield: 76.33% (two steps together).

$^1$H NMR (300 MHz, DMSO-d$_6$) δ 7.91 (ddd, J=17.8, 10.0, 7.3 Hz, 5H), 7.09-6.91 (m, 2H), 4.70 (dd, J=18.5, 8.4 Hz, 2H), 4.21 (s, 1H), 4.09 (dd, J=18.0, 7.4 Hz, 3H), 3.11 (s, 3H), 1.79 (s, 3H). MS(EI) m/z: (M+, 435).

Example 31

Preparation of 5-chloro-N-(((3S,3aS)-7-((R)-4-hydroxy-2-oxopiperidin-1-yl)-1-oxo-1,3,3a,4-tetrahydrobenzo[b]oxazolo[3,4-d][1,4]oxazin-3-yl)methyl)-thiophene-2-carboxamide (compound 31)

(a) (±) 4-hydroxypiperidin-2-one

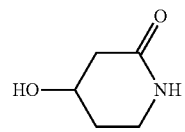

2,4-piperidinedione (1.0 g, 8.84 mmol) was dissolved in MeOH. NaBH$_4$ (0.5 g, 13.26 mmol) was added at 0° C., stirred at 0° C. for 30 min, and the reaction mixture was then placed at room temperature and stirred for 1 h. TLC (DCM/MeOH) was employed to monitor the reaction. After the reaction completed, it was quenched by adding water and dried by spinning. Column chromatography afforded white solid powder 0.8 g, yield 80.0%.

$^1$H NMR (400 MHz, DMSO-d$_6$) δ 7.52-7.28 (s, 1H), 5.06-4.78 (d, J=3.5 Hz, 1H), 4.03-3.78 (dp, J=7.2, 3.9, 3.3 Hz, 1H), 3.28-3.14 (m, 1H), 3.09-2.91 (dtt, J=7.4, 5.2, 2.2 Hz, 1H), 2.42-2.25 (dd, J=17.1, 4.7 Hz, 1H), 2.13-1.93 (dd, J=17.1, 6.1 Hz, 1H), 1.83-1.66 (ddt, J=12.7, 7.9, 3.6 Hz, 1H), 1.69-1.47 (dt, J=13.2, 6.4 Hz, 1H). MS(ESI) m/z: [(M+1)$^+$, 117.1].

(b) (±) 4-(t-butyldiphenylsiloxy) piperidin-2-one

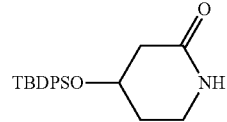

(±) 4-hydroxypiperidin-2-one (0.80 g, 6.94 mmol) was dissolved in DMF. DMAP (0.085 g, 0.694 mmol) and imidazole (0.92 g, 13.88 mmol) were added. After the resulting mixture was stirred evenly, the solution of TBDPS-Cl (2.3 g, 8.33 mmol) in THF was added and stirred at room temperature overnight. After the reaction completed, the reaction mixture was dried by spinning. Column chromatography afforded colorless oily liquid 0.65 g, yield 60%.

$^1$H NMR (300 MHz, CDCl$_3$) δ 7.70-7.49 (m, 4H), 7.53-7.30 (m, 6H), 4.24-4.09 (dt, J=8.9, 3.0 Hz, 1H), 3.62-3.49 (dt, J=13.0, 6.7 Hz, 1H), 3.20-3.08 (dtd, J=11.7, 5.6, 2.3 Hz, 1H), 2.51-2.35 (d, J=4.8 Hz, 2H), 1.83-1.69 (m, 2H), 1.17-1.00 (s, 9H). MS(ESI) m/z: [(M+1)$^+$, 158.3]

(c) (3R,3aS)-3-((t-butyldimethylsiloxy)methyl)-7-((R)-4-(t-butyldiphenylsiloxy)-2-oxopiperidin-1-yl)-3a,4-dihydrobenzo[b]oxazolo[3,4-d][1,4]oxazin-1(3H)-one

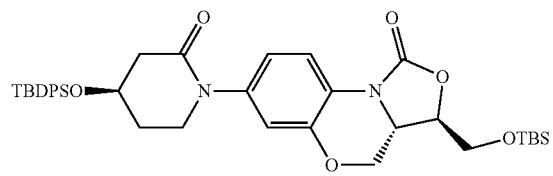

Using compound A (the same as in Example 1) (0.91 g, 2.21 mmol), (±) 4-(t-butyldiphenylsiloxy) piperidin-2-one (0.65 g, 1.84 mmol), cesium carbonate (1.50 g, 4.60 mmol), Pd$_2$(dba)$_3$ (0.12 g, 0.129 mmol), and Xantphos (0.106 g, 0.184 mmol) as starting materials, 1,4-dioxane as solvent, preparation following the method as described in Example 1 (a) afforded golden solid 0.78 g, yield 61.4%.

$^1$H NMR (300 MHz, CDCl$_3$) δ 8.05-7.99 (m, 1H), 7.72-7.63 (ddt, J=8.1, 6.3, 1.7 Hz, 4H), 7.49-7.35 (m, 6H), 6.92-6.89 (m, 1H), 6.89-6.86 (t, J=1.8 Hz, 1H), 3.48-3.37 (m, 1H), 0.92-0.89 (m, 9H), 0.16-0.06 (m, 6H), 4.51-4.39 (ddd, J=10.3, 3.1, 1.4 Hz, 1H), 4.33-4.20 (m, 2H), 4.17-4.05 (ddt, J=8.1, 5.1, 1.5 Hz, 1H), 3.94-3.90 (dd, J=4.7, 1.7 Hz, 2H), 3.87-3.81 (m, 1H), 2.67-2.54 (d, J=4.6 Hz, 2H), 1.97-1.85 (m, 2H), 1.12-1.06 (d, J=1.6 Hz, 9H). MS(ESI) m/z: [(M+1)$^+$, 687.4].

(d) (3R,3aS)-7-((R)-4-(t-butyldiphenylsiloxy)-2-oxopiperidin-1-yl)-3-(hydroxymethyl)-3a,4-dihydrobenzo[b]oxazolo[3,4-d][1,4]oxazin-1 (3H)-one

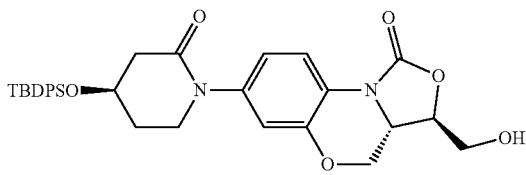

Compound (3R,3 aS)-3-((t-butyldimethylsiloxy)methyl)-7-((R)-4-(t-butyldiphenylsiloxy)-2-oxopiperidin-1-yl)-3a,4-dihydrobenzo[b]oxazolo[3,4-d][1,4]oxazin-1(3H)-one (0.78 g, 1.135 mmol) was dissolved in THF. A solution of BCl$_3$ in dichloromethane (1M, 6.81 ml, 6.81 mmol) was added, stirred at room temperature for 24 h, and dried by spinning. Column chromatography afforded pale yellow solid 0.56 g, yield 86.0%.

$^1$H NMR (300 MHz, CDCl$_3$) δ 8.06-8.00 (d, J=8.3 Hz, 1H), 7.73-7.60 (ddd, J=8.0, 4.9, 1.7 Hz, 4H), 7.50-7.35 (ddd, J=12.5, 8.4, 6.6 Hz, 6H), 6.91-6.84 (m, 2H), 4.51-4.44 (dd, J 10.5, 3.1 Hz, 1H), 4.37-4.30 (dt, J=8.1, 4.0 Hz, 1H), 4.30-4.23 (m, 1H), 4.19-4.09 (ddd, J=10.1, 6.8, 3.1 Hz, 1H), 4.00-3.93 (m, 1H), 3.93-3.88 (m, 1H), 3.88-3.81 (m, 2H), 3.47-3.37 (dt, J=11.1, 5.1 Hz, 1H), 2.67-2.56 (d, J=4.7 Hz, 2H), 1.95-1.87 (q, J=5.7, 5.2 Hz, 2H), 1.13-0.98 (s, 9H). MS(ESI) m/z: [(M+1)$^+$, 573.2].

(e) ((3R,3aS)-7-((R)-4-(t-butyldiphenylsiloxy)-2-oxopiperidin-1-yl)-1-oxo-1,3,3a,4-tetrahydrobenzo[b]oxazolo[3,4-d][1,4]oxazin-3-yl)methyl-methanesulfonate

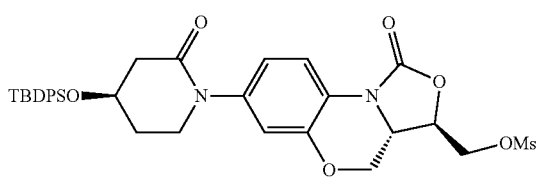

Using compound (3R,3aS)-7-((R)-4-(t-butyldiphenylsiloxy)-2-oxopiperidin-1-yl)-3-(hydroxymethyl)-3a,4-dihydrobenzo[b]oxazolo[3,4-d][1,4]oxazin-1(3H)-one (0.56 g, 1.002 mmol), MsCl (0.14 g, 1.203 mmol), and Et$_3$N (0.20 g, 2.004 mmol) as starting materials, DCM as solvent, preparation following the method as described in Example 1 (c) afforded white solid 0.61 g, yield 96.2%.

$^1$H NMR (300 MHz, CDCl$_3$) δ 8.13-7.85 (d, J=9.3 Hz, 1H), 7.79-7.58 (ddd, J=7.9, 5.0, 1.7 Hz, 4H), 7.55-7.31 (dq, J=8.3, 6.6 Hz, 6H), 7.02-6.78 (m, 2H), 4.69-4.44 (m, 4H), 4.34-4.19 (s, 1H), 4.13-4.01 (s, 1H), 3.97-3.84 (m, 2H), 3.49-3.35 (m, 1H), 3.18-3.05 (s, 3H), 2.71-2.55 (d, J=4.8 Hz, 2H), 2.11-1.84 (d, J=5.3 Hz, 2H), 1.20-0.98 (s, 9H). MS(ESI) m/z: [(M+1)$^+$, 651.4].

2-(((3S,3aS)-7-((R)-4-(t-butyldiphenylsiloxy)-2-oxopiperidin-1-yl)-1-oxo-1,3,3a,4-tetrahydrobenzo[b]oxazolo[3,4-d][1,4]oxazin-3-yl)methyl)-isoindolin-1,3-dione

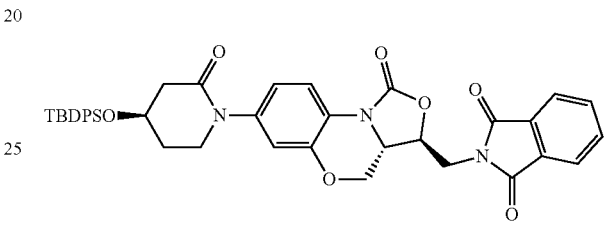

Using compound ((3R,3aS)-7-((R)-4-(t-butyldiphenylsiloxy)-2-oxopiperidin-1-yl)-1-oxo-1,3,3a,4-tetrahydrobenzo[b]oxazolo[3,4-d][1,4]oxazin-3-yl)methyl-methanesulfonate (0.61 g, 1.342 mmol), and phthalimide potassium (0.37 g, 2.013 mmol) as starting materials, DMF as solvent, preparation following the method as described in Example 1 (d) afforded white solid 0.38 g, yield 58.7%.

$^1$H NMR (400 MHz, CDCl$_3$) δ 8.00-7.93 (m, 1H), 7.93-7.84 (m, 2H), 7.81-7.73 (dd, J=5.5, 3.0 Hz, 2H), 7.71-7.63 (tt, J=6.6, 1.5 Hz, 4H), 7.55-7.35 (m, 6H), 6.89-6.87 (m, 1H), 6.87-6.85 (s, 1H), 4.69-4.59 (td, J=6.6, 5.1 Hz, 1H), 4.51-4.42 (dd, J=10.6, 3.1 Hz, 1H), 4.29-4.24 (dt, J=5.8, 2.6 Hz, 1H), 4.24-4.18 (t, J=7.1 Hz, 1H), 2.67-2.52 (d, J=4.4 Hz, 2H), 1.13-1.02 (s, 9H), 1.94-1.83 (m, 2H), 4.11-3.99 (m, 2H), 3.94-3.77 (m, 2H), 3.45-3.36 (dt, J=12.1, 5.2 Hz, 1H). MS(ESI) m/z: [(M+1)$^+$, 702.5].

(g) (3S,3aS)-3-(aminomethyl)-7-((R)-4-(t-butyldiphenylsiloxy)-2-oxopiperidin-1-yl)-3,3a,4-dihydrobenzo[b]oxazolo[3,4-d][1,4]oxazin-1 (3H)-one

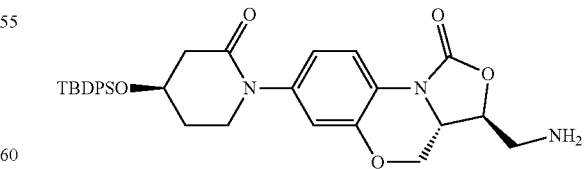

Using compound 2-(((3S,3aS)-7-((R)-4-(t-butyldiphenylsiloxy)-2-oxopiperidin-1-yl)-1-oxo-1,3,3a,4-tetrahydrobenzo[b]oxazolo[3,4-d][1,4]oxazin-3-yl)methyl)-isoindolin-1,3-dione (0.38 g, 0.541 mmol), and methylamine alcohol solution (0.034 g, 1.083 mmol) as starting materials, ethanol as solvent, preparation following the method as described in Example 1 (e) afforded white solid 0.24 g, yield 77.7%.

(h) N-(((3S,3aS)-7-((R)-4-(t-butyldiphenylsiloxy)-2-oxopiperidin-1-yl)-1-oxo-1,3,3a,4-tetrahydrobenzo[b]oxazolo[3,4-d][1,4]oxazin-3-yl)methyl)-5-chlorothiophene-2-carboxamide

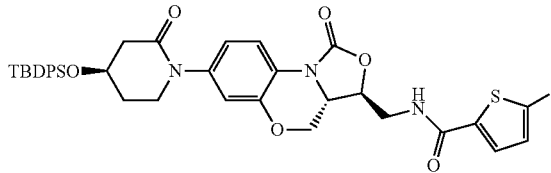

Using compound (3S,3aS)-3-(aminomethyl)-7-((R)-4-(t-butyldiphenylsiloxy)-2-oxopiperidin-1-yl)-3,3a,4-dihydrobenzo[b]oxazolo[3,4-d][1,4]oxazin-1 (3H)-one (0.24 g, 0.420 mmol), 5-chlorothiophene-2-carboxylic acid (0.10 g, 0.630 mmol), HATU (0.32 g, 0.840 mmol), and Et₃N (0.13 g, 1.260 mmol) as starting materials, DCM as solvent, preparation following the method as described in Example 11 (g) afforded white solid 0.36 g, yield 70.6%.

¹H NMR (400 MHz, CDCl₃) δ 8.07-7.90 (d, J=8.2 Hz, 1H), 7.76-7.61 (ddd, J=7.8, 6.1, 1.6 Hz, 4H), 7.49-7.44 (d, J=2.4 Hz, 1H), 7.44-7.34 (m, 5H), 7.16-7.06 (s, 1H), 6.88-6.84 (m, 3H), 4.51-4.40 (m, 2H), 4.30-4.24 (s, 1H), 4.0-3.93 (s, 1H), 3.90-3.80 (m, 2H), 3.80-3.68 (s, 2H), 3.46-3.37 (d, J=11.2 Hz, 1H), 2.62-2.57 (d, J=4.3 Hz, 2H), 1.94-1.88 (s, 2H), 1.11-1.06 (s, 9H). MS(ESI) m/z: [(M+1)⁺, 716.3].

(i) 5-chloro-N-(((3S,3aS)-7-((R)-4-hydroxy-2-oxopiperidin-1-yl)-1-oxo-1,3,3a,4-tetrahydrobenzo[b]oxazolo[3,4-d][1,4]oxazin-3-yl)methyl)-thiophene-2-carboxamide

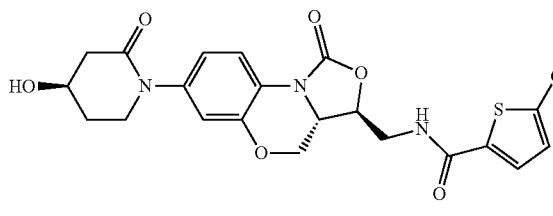

Compound N-(((3S,3aS)-7-((R)-4-(t-butyldiphenylsiloxy)-2-oxopiperidin-1-yl)-1-oxo-1,3,3a,4-tetrahydrobenzo[b]oxazolo[3,4-d][1,4]oxazin-3-yl)methyl)-5-chlorothiophene-2-carboxamide (0.36 g, 0.502 mmol) was dissolved in THF. TBAF (1M/L, 0.50 ml) was added and stirred at room temperature for 2 h. After the reaction completed, the resulting mixture was washed with water, extracted with EA (20 ml×4), dried over anhydrous sodium sulfate, and dried by spinning. Column chromatography afforded white solid 0.13 g, yield 56.2%.

¹H NMR (300 MHz, DMSO-d₆) δ 9.11-8.92 (d, J=5.8 Hz, 1H), 7.86-7.77 (d, J=8.8 Hz, 1H), 7.74-7.69 (d, J=4.1 Hz, 1H), 7.26-7.19 (d, J=4.0 Hz, 1H), 6.93-6.88 (s, 2H), 5.09-5.05 (d, J=3.9 Hz, 1H), 4.64-4.56 (d, J=7.2 Hz, 2H), 4.57-4.51 (d, J=10.8 Hz, 2H), 4.16-4.05 (d, J=6.1 Hz, 3H), 4.04-3.98 (s, 1H), 3.76-3.68 (d, J=6.1 Hz, 2H), 3.68-3.60 (s, 1H), 3.55-3.42 (t, J=6.0 Hz, 1H), 2.66-2.54 (m, 1H), 2.34-2.20 (dd, J=17.0, 6.0 Hz, 1H), 2.08-1.90 (d, J=8.9 Hz, 2H). MS(ESI) m/z: [(M+23)⁺, 500.4].

Example 32

Preparation of 5-chloro-N-(((3S,3aS)-7-((S)-4-hydroxy-2-oxopiperidin-1-yl)-1-oxo-1,3,3a,4-tetrahydrobenzo[b]oxazolo[3,4-d][1.4]oxazin-3-yl)methyl)-thiophene-2-carboxamide (compound 32)

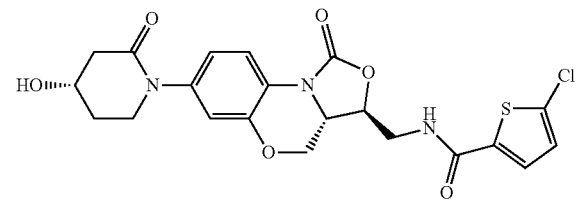 [SMILES: O=C(NC[C@@H]1OC(=O)N2c3ccc(N4CC[C@H](O)CC4=O)cc3OC[C@@H]12)c1ccc(Cl)s1]

The starting materials were the same with that of Example 31. In step (c) of Example 31, column chromatography was used to separate another configuration of compound (3R,3aS)-3-((t-butyldimethylsiloxy)methyl)-7-((S)-4-(t-butyldiphenylsiloxy)-2-oxopiperidin-1-yl)-3a,4-dihydrobenzo[b]oxazolo[3,4-d][1,4]oxazin-1 (3H)-one. Then preparation following the method as described in Example 31 (d-i) afforded compound 31.

¹H NMR (300 MHz, DMSO-d₆) δ 9.05-8.93 (t, J=5.9 Hz, 1H), 7.87-7.77 (d, J=9.0 Hz, 1H), 7.77-7.67 (d, J=4.1 Hz, 1H), 7.25-7.17 (d, J=4.0 Hz, 1H), 6.92-6.83 (m, 2H), 5.12-5.01 (d, J=3.6 Hz, 1H), 4.64-4.55 (dd, J=14.5, 7.4 Hz, 2H), 3.21-3.10 (m, 1H), 4.13-3.97 (t, J=6.2 Hz, 3H), 3.81-3.67 (m, 1H), 3.55-3.40 (dd, J=11.5, 5.4 Hz, 1H), 2.64-2.54 (m, 1H), 2.36-2.19 (dd, J=17.0, 6.0 Hz, 1H), 2.08-1.92 (s, 1H). MS(EI) m/z: [M+, 477].

Example 33

Preparation of 5-chloro-N-(((3S,3aS)-7-((R)-4-fluro-2-oxopiperidin-1-yl)-1-oxo-1,3,3a,4-tetrahydrobenzo[b]oxazolo[3,4-d][1,4]oxazin-3-yl)methyl)-thiophene-2-carboxamide (33)

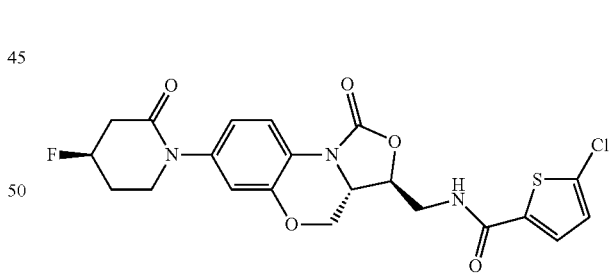

Compound 31 (50 mg, 0.105 mmol) was dissolved in DCM and cooled on ice bath. A solution of DAST in DCM (34 mg, 0.210 mmol) was added under the protection of Ar and stirred at room temperature for 2 h. After the reaction completed, the resulting mixture was dried by spinning. Column chromatography afforded white solid 43 mg, yield 85.0%.

¹H NMR (400 MHz, DMSO-d₆) δ 9.08-8.88 (t, J=5.7 Hz, 1H), 7.91-7.78 (d, J=8.6 Hz, 1H), 7.75-7.66 (d, J=3.9 Hz, 1H), 7.25-7.18 (d, J=3.9 Hz, 1H), 6.96-6.78 (m, 1H), 5.29-5.08 (s, 0H), 4.63-4.42 (m, 2H), 4.12-3.95 (t, J=7.2 Hz, 2H), 3.80-3.66 (t, J=5.6 Hz, 3H), 3.60-3.44 (m, 1H), 2.91-2.74 (m, 1H), 2.67-2.53 (m, 1H), 2.20-2.09 (d, J=6.4 Hz, 1H), 2.05-1.91 (t, J=7.1 Hz, 1H). MS(ESI) m/z: [(M−1)⁺, 477.8].

Example 34

Preparation of 5-chloro-N-(((3S,3aS)-7-((S)-4-fluro-2-oxopiperidin-1-yl)-1-oxo-1,3,3a,4-tetrahydrobenzo[b]oxazolo[3,4-d][1,4]oxazin-3-yl)methyl)-thiophene-2-carboxamide (34)

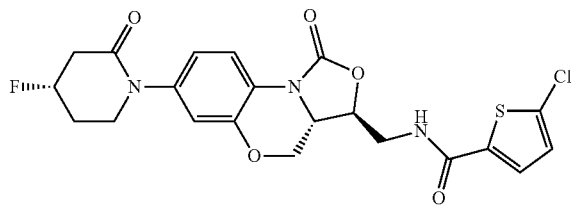 [SMILES: O=C(NC[C@@H]1OC(=O)N2c3ccc(N4CC[C@H](F)CC4=O)cc3OC[C@@H]12)c1ccc(Cl)s1]

Compound 32 (50 mg, 0.105 mmol) was dissolved in DCM and cooled on ice bath. A solution of DAST in DCM (34 mg, 0.210 mmol) was added under the protection of Ar and stirred at room temperature for 2 h. After the reaction completed, the resulting mixture was dried by spinning. Column chromatography afforded white solid 40 mg, yield 79.1%.

$^1$H NMR (400 MHz, DMSO-$d_6$) δ 9.08-8.88 (t, J=5.7 Hz, 1H), 7.91-7.78 (d, J=8.6 Hz, 1H), 7.75-7.66 (d, J=3.9 Hz, 1H), 7.25-7.18 (d, J=3.9 Hz, 1H), 6.96-6.78 (m, 1H), 5.29-5.08 (s, 0H), 4.63-4.42 (m, 2H), 4.12-3.95 (t, J=7.2 Hz, 2H), 3.80-3.66 (t, J=5.6 Hz, 3H), 3.60-3.44 (m, 1H), 2.91-2.74 (m, 1H), 2.67-2.53 (m, 1H), 2.20-2.09 (d, J=6.4 Hz, 1H), 2.05-1.91 (t, J=7.1 Hz, 1H). MS(ESI) m/z: [(M−1)$^+$, 477.9].

Example 35

Preparation of 5-chloro-N-(((3S,3aS)-1-oxo-7-(2-aminosulfonylphenyl)-1,3,3a,4-tetrahydrobenzo[b]oxazolo[3,4-d][1,4]oxazin-3-yl)methyl)thiophene-2-carboxamide (compound 35)

(a) N-(((3S,3aS)-7-bromo-1-oxo-1,3,3a,4-tetrahydrobenzo[b]oxazolo[3,4-d][1,4]oxazin-3-yl)methyl)thiophene-2-carboxamide

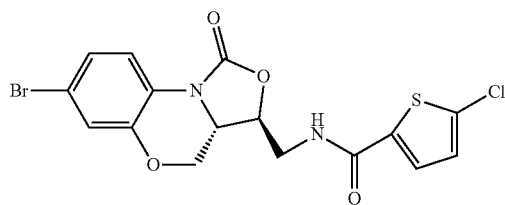 [SMILES: O=C(NC[C@@H]1OC(=O)N2c3ccc(Br)cc3OC[C@@H]12)c1ccc(Cl)s1]

Using compound B

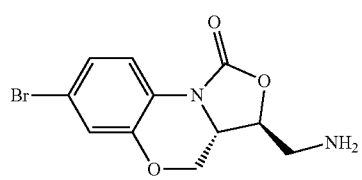 [SMILES: NC[C@@H]1OC(=O)N2c3ccc(Br)cc3OC[C@@H]12]

[Journal of Medicinal Chemistry, 54(21), 7493-7502; 2011] (1 g, 3.36 mmol), 5-chlorothiophene-2-formyl chloride (0.91 g, 5.03 mmol), and TEA (0.678 g, 6.71 mmol) as starting materials, preparation following the method as described in Example 1 (f) afforded white solid 1.208 g, yield 81.2%.

$^1$H NMR (400 MHz, DMSO-$d_6$) δ 8.99 (t, J=5.8 Hz, 1H), 7.81 (d, J=8.7 Hz, 1H), 7.71 (d, J=4.1 Hz, 1H), 7.24-7.14 (m, 3H), 4.64-4.51 (m, 2H), 4.13-4.01 (m, 2H), 3.71 (dd, J=8.2, 3.7 Hz, 2H). MS(EI) m/z: (M$^+$, 444).

(b) 5-chloro-N-(((3S,3 aS)-1-oxo-7-(4,4,5,5-tetramethyl-1,3,2-dioxaborolan-2-yl)-1,3,3a,4-tetrahydrobenzo[b]oxazolo[3,4-d][1,4]oxazin-3-yl)methyl)thiophene-2-carboxamide

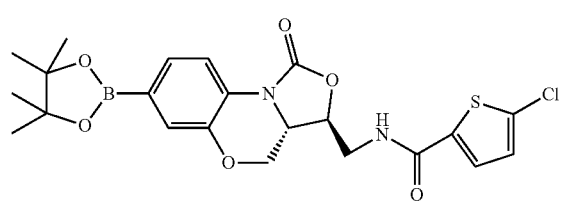 [SMILES: CC1(C)OB(c2ccc3c(c2)OC[C@H]2[C@H](CNC(=O)c4ccc(Cl)s4)OC(=O)N32)OC1(C)C]

Compound N-(((3S,3aS)-7-bromo-1-oxo-1,3,3a,4-tetrahydrobenzo[b]oxazolo[3,4-d][1,4]oxazin-3-yl)methyl)thiophene-2-carboxamide (153 mg, 0.345 mmol) was dissolved in 20 ml of DMSO. Bis(pinacolato)diboron (132 mg, 0.517 mmol) and potassium acetate (102 mg, 1.035 mmol) were added. Under protection of Ar, Pd$_2$ (dppf) CH$_2$Cl$_2$ (29 mg, 0.034 mmol) was added and the mixture was allowed to react at 80° C. for 1 h. TLC (PE/EA=1/1) was employed to monitor the reaction. After the reaction completed, the resulting mixture was diluted by adding EA (50 ml), and then washed with water and saturated saline solution, filtered under reduced pressure, and dried by spinning. Column chromatography (PE/EA=2/1) afforded off-white solid 64 mg, yield: 37.8%.

$^1$H NMR (400 MHz, CDCl$_3$) δ 7.99 (d, J=8.1 Hz, 1H), 7.44-7.36 (m, 2H), 7.30 (d, J=4.0 Hz, 1H), 6.91 (d, J=4.0 Hz, 1H), 6.46 (t, J=6.2 Hz, 1H), 4.55 (dd, J=10.5, 3.0 Hz, 1H), 4.51-4.44 (m, 1H), 4.05-3.98 (m, 1H), 3.94 (ddd, J=14.8, 6.4, 3.1 Hz, 1H), 3.88 (dd, J=16.9, 6.6 Hz, 1H), 3.79 (dt, J=14.9, 6.2 Hz, 1H), 1.32 (s, 12H). MS(EI) m/z: (M$^+$, 490).

(c) 5-chloro-N-(((3S,3aS)-1-oxo-7-(2-t-butylaminosulfonylphenyl)-1,3,3a,4-tetrahydrobenzo[b]oxazolo[3,4-d][1,4]oxazin-3-yl)methyl)thiophene-2-carboxamide

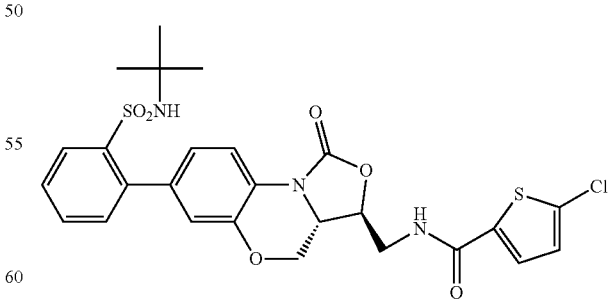

Compound 5-chloro-N-(((3S,3aS)-1-oxo-7-(4,4,5,5-tetramethyl-1,3,2-dioxaborolan-2-yl)-1,3,3a,4-tetrahydrobenzo[b]oxazolo[3,4-d][1,4]oxazin-3-yl)methyl)thiophene-2-carboxamide (60 mg, 0.122 mmol) and N-t-butyl-o-bromobenzenesulfonamide (43 mg, 0.147 mmol)

were dissolved in a mixed solvent of dioxane (5 ml) and water (0.5 ml). Cesium carbonate (80 mg, 0.245 mmol) was added, and tetrakis (triphenylphosphine) palladium (15 mg, 0.012 mmol) was added under the protection of Ar. The resulting mixture was allowed to react under agitation at 80° C. overnight. TLC (PE/EA=1/1) was employed to monitor the reaction. After the reaction completed, the mixture was filtered under reduced pressure, and the solvent was evaporated. Column chromatography (PE/EA=2/1) afforded off-white solid 25 mg, yield: 35.2%.

$^1$H NMR (300 MHz, CDCl$_3$) δ 8.15 (d, J=6.6 Hz, 1H), 8.06 (d, J=8.3 Hz, 1H), 7.72-7.67 (m, 1H), 7.48 (dd, J=7.6, 3.2 Hz, 3H), 7.35 (d, J=4.0 Hz, 1H), 7.15-7.06 (m, 2H), 6.93 (d, J=4.0 Hz, 1H), 6.59 (s, 1H), 4.59 (dd, J=10.4, 2.9 Hz, 1H), 4.56-4.48 (m, 1H), 4.12-4.02 (m, 1H), 4.01-3.78 (m, 3H), 1.05 (s, 9H). MS(EI) m/z: (M$^+$, 575).

(d) 5-chloro-N-(((3S,3aS)-1-oxo-7-(2-aminosulfonylphenyl)-1,3,3a,4-tetrahydrobenzo[b]oxazolo[3,4-d][1,4]oxazin-3-yl)methyl)thiophene-2-carboxamide

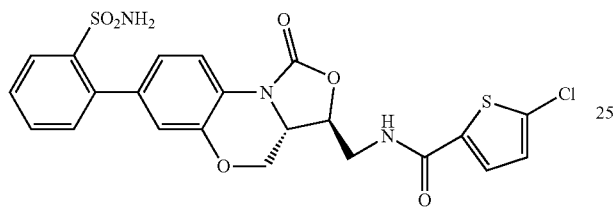

Compound 5-chloro-N-(((3S,3aS)-1-oxo-7-(2-t-butylaminosulfonylphenyl)-1,3,3a,4-tetrahydrobenzo[b]oxazolo[3,4-d][1,4]oxazin-3-yl)methyl)thiophene-2-carboxamide (124 mg, 0.215 mmol) was dissolved in 2 ml of TFA. The resulting mixture was heated to 40° C. and agitated for 2 h. TLC (PE/EA=1/1) was employed to monitor the reaction. After the reaction completed, TFA was evaporated, and the remainder was diluted by 20 ml of EA, washed with 8 ml of water and 8 ml of saturated saline solution for one time each, dried over anhydrous sodium sulfate, and the solvent was evaporated. Column chromatography (PE/EA=2/1) afforded 91 mg of white solid, yield: 81.22%.

$^1$H NMR (300 MHz, DMSO-d$_6$) δ 9.03 (t, J=5.5 Hz, 1H), 8.01 (d, J=7.6 Hz, 1H), 7.87 (d, J=8.6 Hz, 1H), 7.73 (d, J=4.1 Hz, 1H), 7.64-7.52 (m, 2H), 7.30 (d, J=7.3 Hz, 1H), 7.27-7.18 (m, 3H), 7.00 (d, J=7.5 Hz, 2H), 4.60 (dd, J=16.6, 6.9 Hz, 2H), 4.20-4.01 (m, 2H), 3.75 (d, J=5.0 Hz, 2H). MS(EI) m/z: (M$^+$, 519).

Example 36

Preparation of 5-chloro-N-(((3S,3aS)-7-(2-(methylsulfonyl)phenyl)-1-oxo-1,3,3a,4-tetrahydrobenzo[b]oxazolo[3,4-d][1,4]oxazin-3-yl)methyl)thiophene-2-carboxamide (compound 36)

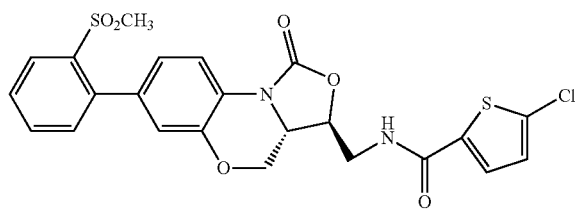 [SMILES: CS(=O)(=O)c1ccccc1-c1ccc2c(c1)OC[C@H]1[C@H](CNC(=O)c3ccc(Cl)s3)OC(=O)N21]

Using compound 5-chloro-N-(((3S,3aS)-1-oxo-7-(4,4,5,5-tetramethyl-1,3,2-dioxaborolan-2-yl)-1,3,3a,4-tetrahydrobenzo[b]oxazolo[3,4-d][1,4]oxazin-3-yl)methyl)thiophene-2-carboxamide (the product of step (b) in Example 35) (50 mg, 0.102 mmol), o-methylsulfonylbromobenzene (29 mg, 0.122 mmol), tetrakis (triphenylphosphine) palladium (12 mg, 0.010 mmol), and cesium carbonate (66 mg, 0.204 mmol) as starting materials, preparation following the method as described in Example 35 (c) afforded off-white solid 19 mg, yield: 35.2%.

$^1$H-NMR (400 MHz, DMSO-d$_6$) δ 9.01 (t, J=5.8 Hz, 1H), 8.08 (dd, J=7.9, 1.2 Hz, 1H), 7.93 (d, J=8.2 Hz, 1H), 7.80-7.70 (m, 2H), 7.70-7.63 (m, 1H), 7.39 (dd, J=7.5, 1.2 Hz, 1H), 7.22 (d, J=4.0 Hz, 1H), 7.07-6.99 (m, 2H), 4.67-4.54 (m, 2H), 4.19-4.06 (m, 2H), 3.73 (d, J 5.6 Hz, 2H), 2.86 (s, 3H). MS(EI) m/z: (M$^+$, 518).

Example 37

Preparation of (3R,3aS)—N-(5-chlorothien-2-yl)-1-oxo-7-(3-oxomorpholin-4-yl)-1,3,3a,4-tetrahydrobenzo[b]oxazolo[3,4-d][1,4]oxazin-3-carboxamide (compound 37)

(a) (3R,3 aS)-1-oxo-7-(3-oxomorpholin-4-yl)-1,3,3a,4-tetrahydrobenzo[b]oxazolo[3,4-d][1,4]oxazin-3-carboxylic acid

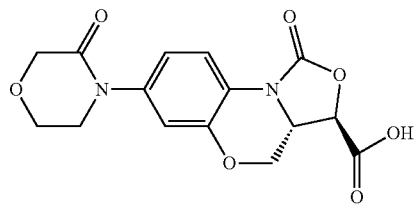 [SMILES: O=C(O)[C@@H]1OC(=O)N2c3ccc(N4CCOCC4=O)cc3OC[C@@H]12]

Compound (3R,3aS)-3-(hydroxymethyl)-7-(3-oxomorpholin-4-yl)-3a,4-dihydrobenzo[b]oxazolo[3,4-d][1,4]oxazin-1 (3H)-one (the product of step (b) in Example 1) (0.38 g, 1.188 mmol) was dissolved in 15 ml of DMSO and cooled on ice bath, to which was added DMP (0.856 g, 2.019 mmol). The resulting mixture was stirred at room temperature for 1 h. TLC (DCM/MeOH=10/1) was employed to monitor the reaction. After the reaction completed, it was quenched by adding 10 ml of aqueous saturated solution of sodium thiosulfate, diluted by 10 ml of water, and extracted with DCM (10 ml×3). The organic phase was combined, and washed with a saturated solution of sodium bicarbonate and a saturated solution of sodium chloride, respectively, and then it was dried over anhydrous sodium sulfate, and the solvent was evaporated. The resulting crude product was directly subjected to the next step of reaction.

The crude product prepared above was dissolved in 10 ml of acetonitrile. NaH$_2$PO$_4$ (37 mg, 0.309 mmol, dissolved in 0.15 ml of water), sodium chlorite (0.151 g, 1.664 mmol, dissolved in 0.3 ml of water), and hydrogen peroxide (0.15 ml) were added, and stirred at room temperature overnight. TLC (DCM/MeOH=5/1) was employed to monitor the reaction. After the reaction completed, the pH value was adjusted to 10 with 10% aqueous solution of NaOH. The reaction mixture was wash with EA (10 ml×3). The pH value of the aqueous phase was adjusted to 3 with 1M aqueous solution of hydrochloric acid. The mixture was then extracted with EA (15 ml×5), dried over anhydrous sodium sulfate, and the solvent was evaporated to afford white solid 173 mg, two-step yield: 43.6%.

¹H NMR (300 MHz, DMSO-d$_6$) δ 7.82 (d, J=8.6 Hz, 1H), 7.09-7.00 (m, 2H), 5.02 (d, J=6.9 Hz, 1H), 4.57 (dd, J=10.6, 3.3 Hz, 1H), 4.36 (ddd, J=10.1, 6.9, 3.3 Hz, 1H), 4.18 (s, 2H), 4.12 (t, J=10.3 Hz, 1H), 3.95 (dd, J=6.2, 3.9 Hz, 2H), 3.73-3.66 (m, 2H). MS(EI) m/z: (M⁺, 334).

(b) (3R,3aS)—N-(5-chlorothien-2-yl)-1-oxo-7-(3-oxomorpholin-4-yl)-1,3,3a,4-tetrahydrobenzo[b]oxazolo[3,4-d][1,4]oxazin-3-carboxamide

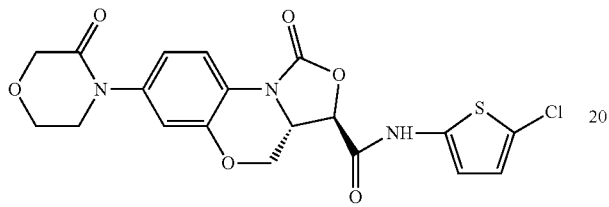

Using compound (3R,3 aS)-1-oxo-7-(3-oxomorpholin-4-yl)-1,3,3a,4-tetrahydrobenzo[b]oxazolo[3,4-d][1,4]oxazin-3-carboxylic acid (90 mg, 0.269 mmol), 5-chlorothiophene-2-amine hydrochloride (55 mg, 0.323 mmol), HATU (154 mg, 0.404 mmol), and TEA (95.3 mg, 0.943 mmol) as starting materials, preparation following the method as described in Example 11 (g) afforded white solid 73 mg, yield: 60.34%.

¹H NMR (300 MHz, DMSO-d$_6$) δ 11.97 (s, 1H), 7.87 (d, J=8.6 Hz, 1H), 7.10 (d, J=2.1 Hz, 1H), 7.06 (dd, J=8.6, 2.3 Hz, 1H), 6.95 (d, J=4.2 Hz, 1H), 6.77 (d, J=4.2 Hz, 1H), 5.15 (d, J=6.9 Hz, 1H), 4.64 (dd, J=10.6, 3.2 Hz, 1H), 4.49-4.34 (m, 1H), 4.30-4.13 (m, 3H), 4.04-3.91 (m, 2H), 3.80-3.65 (m, 2H). MS(EI) m/z: (M+, 449).

Example 38

Preparation of (3R,3aS)—N-(5-chloropyridin-2-yl)-1-oxo-7-(3-oxomorpholin-4-yl)-1,3,3a,4-tetrahydrobenzo[b]oxazolo[3,4-d][1,4]oxazin-3-carboxamide (compound 38)

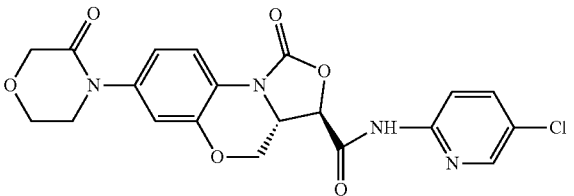 [SMILES: O=C(Nc1ccc(Cl)cn1)[C@@H]1OC(=O)N2c3ccc(N4CCOCC4=O)cc3OC[C@@H]12]

Using compound (3R,3aS)-1-oxo-7-(3-oxomorpholin-4-yl)-1,3,3a,4-tetrahydrobenzo[b]oxazolo[3,4-d][1,4]oxazin-3-carboxylic acid (the product of step (b) in Example 36) (90 mg, 0.24 mmol), 5-chloropyridine-2-amine (37 mg, 0.287 mmol), HATU (137 mg, 0.36 mmol), and TEA (48.4 mg, 0.48 mmol) as starting materials, preparation following the method as described in Example 11 (g) afforded white solid 56 mg, yield: 52.65%.

¹H NMR (3400 MHz, CDCl$_3$) δ 8.86 (s, 1H), 8.31 (d, J=2.2 Hz, 1H), 8.18 (d, J=8.9 Hz, 1H), 8.04 (d, J=8.7 Hz, 1H), 7.73 (dd, J=8.8, 2.5 Hz, 1H), 7.06-6.97 (m, 2H), 4.81-4.72 (m, 2H), 4.40-4.29 (m, 3H), 4.06-3.96 (m, 3H), 3.77-3.71 (m, 2H). MS(EI) m/z: (M⁺, 444).

Example 39

Preparation of 5-chloro-N-(((3S,3aS)-7-(4-methyl-5,6dihydro-4H-1,2,4-oxadiazin-3-yl)-1-oxo-1,3,3a,4-tetrahydrobenzo[b]oxazolo[3,4-d][1,4]oxazin-3-yl)methyl)thiophene-2-carboxamide (compound 39)

(a) (3R,3aS)-3-((t-butyldimethylsiloxy)methyl)-1-oxo-1,3,3a,4-tetrahydrobenzo[b]oxazolo[3,4-d][1,4]oxazin-7-carbonitrile

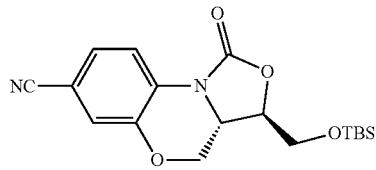 [SMILES: CC(C)(C)[Si](C)(C)OC[C@@H]1OC(=O)N2c3ccc(C#N)cc3OC[C@@H]12]

Compound A (1 g, 2.42 mmol) was dissolved in 20 ml of anhydrous NMP. Sodium carbonate (0.256 g, 2.42 mmol) was added. Under the protection of argon, Pd(OAc)$_2$ (54 mg, 0.242 mmol) and KFe(CN)$_6$.3H$_2$O (0.816 g, 1.93 mmol) were added, and the mixture was allowed to react at 140° C. for 1.5 h. TLC (PE/EA=10/1) was employed to monitor the reaction. The reaction liquid was cooled to room temperature. 20 ml of water was added, and the resulting mixture was extracted with EA (15 ml×3). The organic phase was combined and dried over anhydrous sodium sulfate. The solvent was removed by evaporation to give a crude product, which through column chromatography (PE/EA=8/1) afforded white solid 0.271 g, yield 31.2%.

¹H NMR (400 MHz, CDCl$_3$) 68.18 (d, J=8.5 Hz, 1H), 7.32 (dd, J=8.5, 1.8 Hz, 1H), 7.27 (d, J=1.6 Hz, 1H), 4.55 (dd, J=10.6, 3.3 Hz, 1H), 4.35 (ddd, J=7.0, 5.5, 3.9 Hz, 1H), 4.19 (ddd, J=10.2, 7.0, 3.3 Hz, 1H), 4.02-3.89 (m, 3H), 0.92 (s, 9H), 0.14 (d, J=2.1 Hz, 6H). MS(EI) m/z: (M⁺, 360).

(b) (3R,3aS)-3-(hydroxymethyl)-1-oxo-1,3,3a,4-tetrahydrobenzo[b]oxazolo[3,4-d][1,4]oxazin-7-carbonitrile

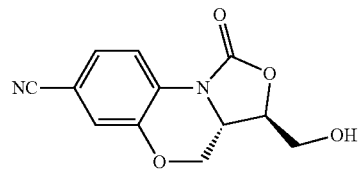 [SMILES: N#Cc1ccc2c(c1)OC[C@H]1[C@H](CO)OC(=O)N21]

Using compound (3R,3 aS)-3-((t-butyldimethylsiloxy)methyl)-1-oxo-1,3,3a,4-tetrahydrobenzo[b]oxazolo[3,4-d][1,4]oxazin-7-carbonitrile (0.538 g, 1.494 mmol), tetra-n-butylammonium fluoride (1M, 2.99 ml) as starting materials, preparation following the method as described in Example 1(b) afforded 0.24 g white solid, yield 65.3%.

¹H NMR (400 MHz, DMSO-d$_6$) δ8.06 (d, J=8.5 Hz, 1H), 7.52 (d, J=1.8 Hz, 1H), 7.46 (d, J=8.5, 1.9 Hz, 1H), 5.34 (t, J=5.7 Hz, 1H), 4.66-4.56 (m, 1H), 4.50 (dd, J=9.4, 4.0 Hz, 1H), 4.14-4.07 (m, 2H), 3.73 (dddd, J=12.4, 10.1, 5.7, 3.9 Hz, 2H). MS(EI) m/z: (M⁺, 246).

(c) ((3R,3aS)-7-cyano-1-oxo-1,3,3a,4-tetrahydrobenzo[b]oxazolo[3,4-d][1,4]oxazin-3-yl)methyl-methanesulfonate

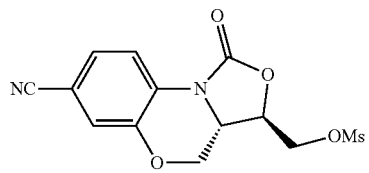 [SMILES: CS(=O)(=O)OC[C@@H]1OC(=O)N2c3ccc(C#N)cc3OC[C@@H]12]

Using compound (3R,3 aS)-3-(hydroxymethyl)-1-oxo-1,3,3a,4-tetrahydrobenzo[b]oxazolo[3,4-d][1,4]oxazin-7-carbonitrile (0.255 g, 0.98 mmol), methylsulfonyl chloride (0.168 g, 1.46 mmol), and TEA (0.197 g, 1.95 mmol) as starting materials, preparation following the method as described in Example 1(c) afforded white solid 0.314 g, yield: 93.5%.

$^1$H NMR (400 MHz, DMSO-$d_6$) δ 8.05 (d, J=8.5 Hz, 1H), 7.54 (d, J=1.6 Hz, 1H), 7.48 (dd, J=8.5, 1.8 Hz, 1H), 4.82 (s, 1H), 4.70-4.55 (m, 3H), 4.17-4.09 (m, 2H), 3.29 (s, 3H). MS(EI) m/z: (M$^+$, 324).

(d) (3S,3 aS)-3-((1,3-dioxoisoindolin-2-yl)methyl)-1-oxo-1,3,3a,4-tetrahydrobenzo[b]oxazolo[3,4-d][1,4]oxazin-7-carbonitrile

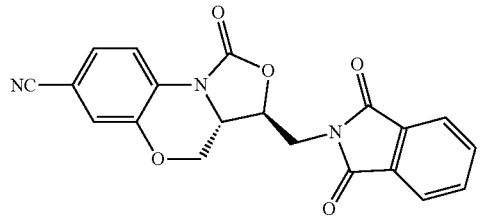 [SMILES: N#Cc1ccc2c(c1)OC[C@H]1[C@H](CN3C(=O)c4ccccc4C3=O)OC(=O)N21]

Using compound ((3R,3aS)-7-cyano-1-oxo-1,3,3a,4-tetrahydrobenzo[b]oxazolo[3,4-d][1,4]oxazin-3-yl)methyl-methanesulfonate (0.31 g, 0.957 mmol) and phthalimide potassium (0.266 g, 1.435 mmol) as starting materials, preparation following the method as described in Example 1(d) afforded white solid 0.286 g, yield: 79.71%.

$^1$H NMR (400 MHz, DMSO-$d_6$) δ 8.04 (d, J=8.5 Hz, 1H), 7.91 (dt, J=6.6, 3.5 Hz, 2H), 7.87 (dt, J=5.1, 3.5 Hz, 2H), 7.51 (d, J=1.8 Hz, 1H), 7.45 (dd, J=8.5, 1.9 Hz, 1H), 4.78-4.68 (m, 2H), 4.28-4.22 (m, 1H), 4.15-4.08 (m, 3H). MS(EI) m/z: (M$^+$, 375).

(e) (3S,3 aS)-3-(aminomethyl)-1-oxo-1,3,3a,4-tetrahydrobenzo[b]oxazolo[3,4-d][1,4]oxazin-7-carbonitrile

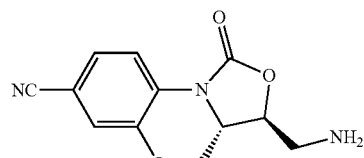

Using (3S,3 aS)-3-((1,3-dioxoisoindolin-2-yl)methyl)-1-oxo-1,3,3a,4-tetrahydrobenzo[b]oxazolo[3,4-d][1,4]oxazin-7-carbonitrile (0.286 g, 0.763 mmol) and 1 ml of methylamine alcohol solution as starting materials, preparation following the method as described in Example 1(e) afforded a crude product, which was directly subjected to the next step of reaction without purification.

(f) 5-chloro-N-(((3S,3 aS)-7-cyano-1-oxo-1,3,3a,4-tetrahydrobenzo[b]oxazolo[3,4-d][1,4]oxazin-3-yl)methyl)thiophene-2-carboxamide

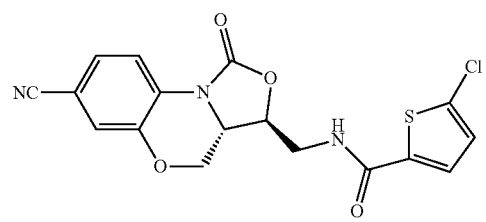 [SMILES: N#Cc1ccc2c(c1)OC[C@H]1[C@H](CNC(=O)c3ccc(Cl)s3)OC(=O)N21]

Using the crude (3S,3aS)-3-(aminomethyl)-1-oxo-1,3,3a,4-tetrahydrobenzo[b]oxazolo[3,4-d][1,4]oxazin-7-carbonitrile, 5-chlorothiophene-2-formyl chloride (0.166 g, 0.915 mmol), and TEA (0.154 g, 1.525 mmol) as starting materials, preparation following the method as described in Example 1(f) afforded white compound 0.225 g, two-step yield: 75.68%.

$^1$H NMR (400 MHz, DMSO-$d_6$) δ 9.01 (t, J=5.8 Hz, 1H), 8.07 (d, J=8.5 Hz, 1H), 7.71 (d, J=4.1 Hz, 1H), 7.52 (d, J=1.8 Hz, 1H), 7.46 (dd, J=8.5, 1.9 Hz, 1H), 7.21 (d, J=4.1 Hz, 1H), 4.62 (t, J=7.0 Hz, 2H), 4.18-4.07 (m, 2H), 3.73 (t, J=6.1 Hz, 2H). MS(ESI) m/z: [(M+35)$^+$, 423.9].

(g) 5-chloro-N-(((3S,3aS)-7-(4-methyl-5,6-dihydro-4H-1,2,4oxadiazin-3-yl)-1-oxo-1,3,3a,4-tetrahydrobenzo[b]oxazolo[3,4-d][1,4]oxazin-3-yl)methyl)thiophene-2-carboxamide

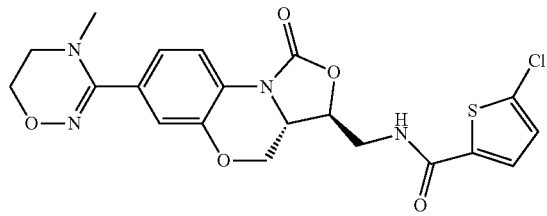 [SMILES: CN1CCON=C1c1ccc2c(c1)OC[C@H]1[C@H](CNC(=O)c3ccc(Cl)s3)OC(=O)N21]

Compound 5-chloro-N-(((3S,3 aS)-7-cyano-1-oxo-1,3,3a,4-tetrahydrobenzo[b]oxazolo[3,4-d][1,4]oxazin-3-yl)methyl)thiophene-2-carboxamide (85 mg, 0.218 mmol) was dissolved in 7 ml of anhydrous methanol and cooled to 0° C. The reaction mixture was bubbled with hydrogen chloride gas for 2 h and then gradually raised to room temperature, stirring until the starting materials completely disappeared. The solvent was evaporated under reduced pressure. The residue was dissolved in 8 ml of glacial acetic acid, to which was added 2-(aminooxy)-N-methylethylamine (98 mg, 1.09 mmol). The resulting mixture was refluxed at 120° C. for 16 h. After the reaction completed, the solvent was evaporated. Column chromatography (DCM/MeOH-80/1, 50/1, 30/1) afforded white solid 13 mg, yield: 12.88%.

¹H NMR (400 MHz, CDCl₃) δ 8.01 (d, J=8.4 Hz, 1H), 7.45 (d, J=4.0 Hz, 1H), 7.36 (t, J=4.8 Hz, 1H), 7.04 (d, J=8.5 Hz, 1H), 7.00 (d, J=1.5 Hz, 1H), 6.88 (d, J=4.0 Hz, 1H), 4.50 (dd, J=10.4, 2.5 Hz, 2H), 4.11 (t, J=4.5 Hz, 2H), 3.98 (dd, J=12.2, 5.3 Hz, 1H), 3.84-3.70 (m, 3H), 3.45 (t, J=4.5 Hz, 2H), 2.78 (s, 3H). MS(EI) m/z: (M⁺, 462).

Example 40

Preparation of 5-chloro-N-(((3S,3aR)-1-oxo-7-(3-oxomorpholin-4-yl)-1,3,3a,4-tetrahydrobenzo[b]oxazolo[3,4-d][1,4]oxazin-3-yl)methyl)thiophene-2-carboxamide (compound 40)

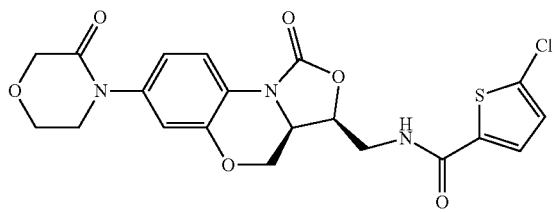 [SMILES: O=C(NC[C@@H]1OC(=O)N2c3ccc(N4CCOCC4=O)cc3OC[C@H]12)c1ccc(Cl)s1]

(a) (3R,3aR)-3-((t-butyldimethylsiloxy)methyl)-7-(3-oxomorpholin-4-yl)-3a,4-dihydrobenzo[b]oxazolo[3,4-d][1,4]oxazin-1 (3H)-one

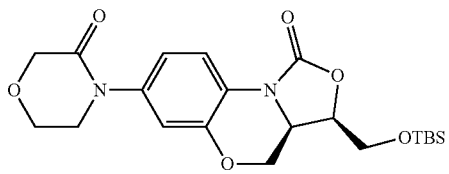 [SMILES: CC(C)(C)[Si](C)(C)OC[C@@H]1OC(=O)N2c3ccc(N4CCOCC4=O)cc3OC[C@H]12]

Using compound C

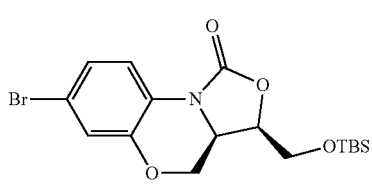 [SMILES: CC(C)(C)[Si](C)(C)OC[C@@H]1OC(=O)N2c3ccc(Br)cc3OC[C@H]12]

[Journal of Medicinal Chemistry, 54(21), 7493-7502; 2011] (1 g, 12.08 mmol), morpholone (0.336 g, 3.62 mmol), cesium carbonate (1.97 g, 6.04 mmol), Pd₂(dba)₃ (0.155 g, 0.169 mmol), and Xantphos (0.14 g, 0.242 mmol) as starting materials, preparation following the method as described in Example 1 (a) afforded off-white solid 0.597 g, yield 56.95%.

¹H NMR (300 MHz, DMSO-d₆) δ 7.88 (d, J=8.5 Hz, 1H), 7.09-6.92 (m, 2H), 4.65 (d, J=7.6 Hz, 2H), 4.21 (s, 2H), 3.99 (ddd, J=16.0, 15.6, 5.9 Hz, 6H), 3.77 (dd, J=5.9, 4.3 Hz, 2H), 0.88-0.83 (m, 9H), 0.08 (d, J=0.5 Hz, 6H). MS(EI) m/z: (M⁺, 434).

(b) (3R,3aR)-3-(hydroxymethyl)-7-(3-oxomorpholin-4-yl)-3a,4-dihydrobenzo[b]oxazolo[3,4-d][1,4]oxazin-1 (3H)-one

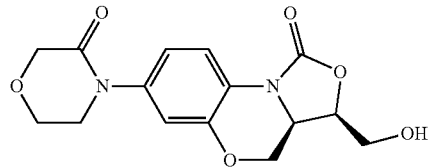

Using compound (3R,3 aR)-3-((t-butyldimethylsiloxy)methyl)-7-(3-oxomorpholin-4-yl)-3a,4-dihydrobenzo[b]oxazolo[3,4-d][1,4]oxazin-1(3H)-one (0.597 g, 1.38 mmol) prepared above in (a), and tetra-n-butylammonium fluoride (1M, 2.8 ml) as starting materials, preparation following the method as described in Example 1 (b) afforded 0.283 g of white solid, yield 64.3%.

¹H NMR (400 MHz, DMSO-d₆) δ 7.90 (d, J=8.7 Hz, 1H), 7.05 (d, J=2.3 Hz, 1H), 6.96 (dd, J=8.7, 2.3 Hz, 1H), 5.33 (t, J=5.7 Hz, 1H), 4.50 (m, 1H), 4.51 (q, J=4.5 Hz, 1H), 4.27 (s, 2H), 4.10 (dd, J=4.5, 1.7 Hz, 2H), 3.98 (m, 2H), 3.88-3.62 (m, 4H). MS(EI) m/z: (M⁺, 320).

(c) ((3R,3 aR)-1-oxo-7-(3-oxomorpholin-4-yl)-1,3,3a,4-tetrahydrobenzo[b]oxazolo[3,4-d][1,4]oxazin-3-yl)methylmethanesulfonate

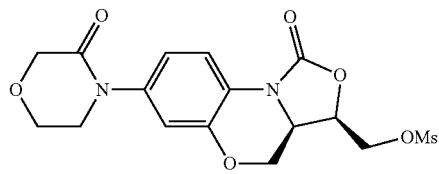 [SMILES: CS(=O)(=O)OC[C@@H]1OC(=O)N2c3ccc(N4CCOCC4=O)cc3OC[C@H]12]

Using compound (3R,3aR)-3-(hydroxymethyl)-7-(3-oxomorpholin-4-yl)-3a,4-dihydrobenzo[b]oxazolo[3,4-d][1,4]oxazin-1 (3H)-one (3 g, 9.375 mmol) prepared above in (b), methylsulfonyl chloride (1.288 g, 11.25 mmol), and TEA (2.6 ml) as starting materials, preparation following the method as described in Example 1 (c) afforded white solid 2.98 g, yield: 79.79%.

¹H NMR (400 MHz, DMSO-d₆) δ 7.91 (d, J=8.1 Hz, 1H), 7.13 (d, J=2.3 Hz, 1H), 7.03 (dd, J=8.1, 2.3 Hz, 1H), 4.88 (s, 1H), 4.69 (m, 3H), 4.25 (s, 2H), 4.17 (d, J=5.2 Hz, 2H), 3.96 (m, 2H), 3.77 (m, 2H), 3.29 (s, 3H). MS(EI) m/z: (M⁺, 398).

(d) 2-(((3S,3 aR)-1-oxo-7-(3-oxomorpholin-4-yl)-1,3,3a,4-tetrahydrobenzo[b]oxazolo[3,4-d][1,4]oxazin-3-yl)methyl)isoindolin-1,3-dione

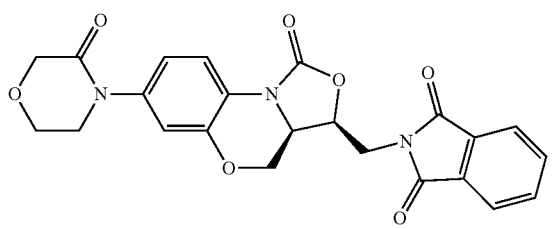 [SMILES: O=C1c2ccccc2C(=O)N1C[C@@H]1OC(=O)N2c3ccc(N4CCOCC4=O)cc3OC[C@H]12]

Using compound ((3R,3 aR)-1-oxo-7-(3-oxomorpholin-4-yl)-1,3,3a,4-tetrahydrobenzo[b]oxazolo[3,4-d][1,4]oxazin-3-yl)methylmethanesulfonate (2.98 g, 7.48 mmol) prepared above in (a) and phthalimide potassium (2.08 g, 11.22 mmol) as starting materials, preparation following the method as described in Example 1 (d) afforded white solid 2.76 g, yield: 82.1%.

$^1$H NMR (400 MHz, CDCl$_3$) δ 8.11 (d, J=8.7 Hz, 1H), 7.91 (dd, J=5.5, 3.0 Hz, 2H), 7.79 (dd, J=5.5, 3.0 Hz, 2H), 7.09 (d, J=2.4 Hz, 1H), 6.99 (dd, J=8.7, 2.4 Hz, 1H), 4.68 (dd, J=11.7, 6.8 Hz, 1H), 4.50 (dd, J=10.6, 3.1 Hz, 1H), 4.38 (s, 2H), 4.23 (dd, J=14.3, 6.8 Hz, 1H), 4.11-3.99 (m, 4H), 3.88 (t, J=10.3 Hz, 1H), 3.74-3.69 (m, 2H). MS(EI) m/z: (M$^+$, 449).

(e) (3S,3aR)-3-aminomethyl-7-(3-oxomorpholin-4-yl)-3a,4-dihydrobenzo[b]oxazolo[3,4-d][1,4]oxazin-1 (3H)-one

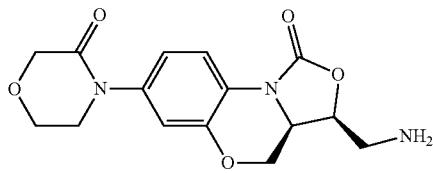 [SMILES: NC[C@@H]1OC(=O)N2c3ccc(N4CCOCC4=O)cc3OC[C@H]12]

Using compound 2-(((3S,3aR)-1-oxo-7-(3-oxomorpholin-4-yl)-1,3,3a,4-tetrahydrobenzo[b]oxazolo[3,4-d][1,4]oxazin-3-yl)methyl)isoindolin-1,3-dione (2.76 g, 6.15 mmol) prepared above in (d) and 50 ml of methylamine alcohol solution as starting materials, preparation following the method as described in Example 1 (e) afforded a crude product, which was directly subjected to the next step of reaction.

(f) 5-chloro-N-(((3S,3aR)-1-oxo-7-(3-oxomorpholin-4-yl)-1,3,3a,4-tetrahydrobenzo[b]oxazolo[3,4-d][1,4]oxazin-3-yl)methyl)thiophene-2-carboxamide

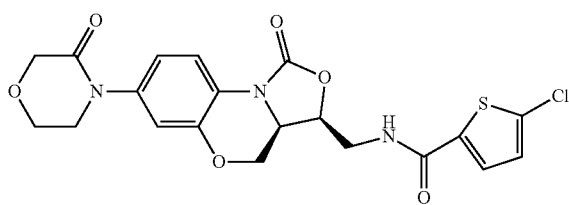 [SMILES: O=C(NC[C@@H]1OC(=O)N2c3ccc(N4CCOCC4=O)cc3OC[C@H]12)c1ccc(Cl)s1]

Using the crude compound (3S,3 aR)-3-aminomethyl-7-(3-oxomorpholin-4-yl)-3a,4-dihydrobenzo[b]oxazolo[3,4-d][1,4]oxazin-1 (3H)-one prepared above in (e) without purification, TEA (1.7 ml, 12.29 mmol), and 5-chlorothiophene-2-formyl chloride (1.335 g, 7.376 mmol) as starting materials, preparation following the method as described in Example 1 (f) afforded white solid 2.02 g, yield: 70.8% (two steps together).

$^1$H NMR (400 MHz, DMSO-d$_6$) δ 9.00 (t, J=5.7 Hz, 1H), 7.95 (d, J=8.7 Hz, 1H), 7.69 (d, J=4.1 Hz, 1H), 7.19 (d, J=4.0 Hz, 1H), 7.15 (d, J=2.3 Hz, 1H), 7.11 (dd, J=8.7, 2.3 Hz, 1H), 4.66-4.57 (m, 2H), 4.21 (s, 2H), 4.08 (m, 2H), 3.97-3.92 (m, 2H), 3.73 (t, J=5.5 Hz, 2H), 3.71-3.66 (m, 2H). MS(ESI) m/z: [(M+23)$^+$, 486.3].

Biological Activity Test

1, FXa Inhibitory Activity Assay of the Compound According to the Present Invention Experimental principle and method: FXa cuts the Arg carboxyl end in the substrate N-Z-D-Arg-Gly-Arg-pDA in vitro and releases p-nitrophenylamine which has specific absorption at 405 nm wavelength. The amount of the substrate generated is determined at 405 nm to evaluate the activity of the compound to inhibit the human recombinant FXa in vitro.

Human plasma coagulation factor Xa was purchased from Calbiochem; the substrate N-Z-D-Arg-Gly-Arg-pDA was purchased from chromogenic. The subject compound, enzyme and the reaction buffer were mixed and preincubated at 37° C. for 10 mins. The substrate was added. The absorption at 405 nm wavelength was measured continuously over 20 mins. At the same time, a blank control group (without enzyme, 100% inhibition rate) and a negative control group (replace the subject compound with DMSO, 0% inhibition rate) were set up. The reaction system was 100 μl (50 μl of Tris buffer, 10 μl of compound, 20 μl (0.027 U/ml) of enzyme, 20 μl (300 μM) of substrate). Each concentration of each sample was assayed in triplicate. The experiment was carried out for 2 times independently.

The subject compound was each dissolved in DMSO to give a 10 mM stock solution, which was then diluted to various concentrations with reaction buffer when use. The positive control group was rivaroxaban (Brand name: Xarelto, approved for sale in Canada and the European Union on September 16$^{th}$ and October 1$^{st}$ of 2008.)

TABLE 2

Inhibitory activity data of part of the compounds of the present invention on FXa

| Compound | IC$_{50}$ (nM) |
|---|---|
| 1 | 2.25 ± 0.01 |
| 2 | 6.68 ± 0.79 |
| 17 | 12.22 ± 10.52 |
| 33 | 14.97 ± 1.60 |
| 34 | 19.27 ± 3.39 |
| 35 | 19.56 ± 16.93 |
| 36 | 12.16 ± 4.08 |
| rivaroxaban | 19.71 ± 0.7 |

It can be seen from the data of Table 2 that the compounds of the present invention nave excellent biological activity. For example, Compounds 1, 2, 17, 33, 34, 35, and 36 have potent in vitro inhibitory activity on FXa; particularly, the FXa inhibitory activity of compounds 1, 2, 17, and 36 are significantly superior to that of the positive drug rivaroxaban.

2, In Vivo Pharmacokinetic Assay of the Compound of the Present Invention in Rats Healthy male SD rats, body weight 200-220 g, randomly divided into 6 groups with each group 3-4 rats, were administered with the subject compound via intragastric administration and intravenous injection, respectively. The specific regimes are shown in the following Table 3:

TABLE 3

Administration regime of the in vivo pharmacokinetic assay in rats.

| Group | Compound | Administration Route | Dosage (mg/kg) | Administration volume (ml/kg) |
|---|---|---|---|---|
| 1 | 1 | intragastric administration | 10 | 10 |
| 2 | 1 | intravenous injection | 3.0 | 5.0 |

TABLE 3-continued

Administration regime of the in vivo pharmacokinetic assay in rats.

| Group | Compound | Administration Route | Dosage (mg/kg) | Administration volume (ml/kg) |
|---|---|---|---|---|
| 3 | 2 | intragastric administration | 9.0 | 10 |
| 4 | 2 | intravenous injection | 4.5 | 5.0 |
| 5 | rivaroxaban | intragastric administration | 10 | 10 |
| 6 | rivaroxaban | intravenous injection | 3.0 | 5.0 |

The subject compound was prepared with 5% DMSO/5% Twain 80/90% saline into solution for administration. Rivaroxaban intragastric administration group was prepared with 5% DMSO/5% Twain −80/90% saline, which produced a suspension, and the intravenous administration group was prepared with 10% DMSO/10% Twain −80/80% PEG400 (50%).

The rats were fasted for 12 hrs before experiment, free water-drinking, and were all fed 2 h after administration. Blood sampling time and sample treatment:

intragastric administration: 0.25, 0.5, 1.0, 2.0, 3.0, 4.0, 6.0, 8.0, and 24 h after administration;

intravenous administration: 5 min, 0.25, 0.5, 1.0, 2.0, 4.0, 6.0, 8.0, and 24 h after administration.

At the time points defined above, 0.3 ml of venous blood was taken from the posterior venous plexus of rats to heparinized tubes, centrifuged at 11000 rpm for 5 mins to separate the plasma, which was then frozen at −20° C. in a refrigerator.

1) Measurement of Prothrombin Time (PT)

Principle: An excessive amount of tissue thromboplastin (infusion of preparations such as human brain, rabbit brain, placenta, and lung tissue) and calcium ion are added to the plasma to be tested, thereby converting prothrombin into thrombin, and the latter converts fibrinogen into fibrin. The time needed for plasma coagulation is observed as prothrombin time. This experiment is the most commonly used screening test for the evaluation of an extrinsic coagulation system.

Test method: To the rabbit sodium citrate anticoagulant plasma (3.8% sodium citrate, 1:9 mixture) were added various concentrations of the compounds to be tested. PT reagents (PRECIL, Beijing) were used to measure the prothrombin activation time. The compound concentration that prolonged the PT time by 1 time, when compared with the blank control, was recorded as PT2, thereby evaluating the anticoagulant activity of the compounds.

2) Measurement of Activated Partial Thromboplastin Time (APTT)

Principle: At 37° C., using Kaolin to activate factors □ and □; using cephalin (partial thromboplastin) to replace platelet factor 3; and in the presence of $Ca^{2+}$, the time needed for the coagulation of plasma which lacks of platelet is observed as activated partial thromboplastin time. This experiment is a screening test which is sensitive and commonly used for the endogenous blood coagulation system.

Test method: To the rabbit sodium citrate anticoagulant plasma (3.8% sodium citrate, 1:9 mixture) were added various concentrations of the compounds to be tested. APTT reagents (PRECIL, Beijing) were used to measure the prothrombin activation time. The compound concentration that prolonged the APTT time by 1 time, when compared with the

TABLE 4

Pharmacokinetic data in rats

| | Compound 1 | | Compound 2 | | rivaroxaban | |
|---|---|---|---|---|---|---|
| | Oral administration (10 mg/Kg) | Intravenous injection (3 mg/Kg) | Oral administration (9 mg/Kg) | Intravenous injection (4.5 mg/Kg) | Oral administration (10 mg/Kg) | Intravenous injection (3 mg/Kg) |
| $T_{max}$ (h) | 0.75 | | 0.67 | | 0.56 | |
| $C_{max}$ (ng/mL) | 11901 | | 6927 | | 440 | |
| $AUC_{0-t}$ (ngh/mL) | 32529 | 15324 | 26119 | 31057 | 1608 | 10548 |
| $AUC_{0-\infty}$ (ngh/mL) | 33044 | 15339 | 28527 | 33562 | 2242 | 10575 |
| MRT(h) | 2.23 | 1.03 | 3.40 | 3.04 | 7.01 | 0.88 |
| $T_{1/2}$ (h) | 1.33 | 1.00 | 2.10 | 1.95 | 4.64 | 0.98 |
| CLz (L/h/Kg) | | 0.201 | | 0.137 | | 0.285 |
| Vss (L/Kg) | | 0.201 | | 0.406 | | 0.250 |
| F(%) | 63.7 | | 42.0 | | 4.6 | |

Excellent metabolic property is a key parameter for drugability of a compound. The pharmacokinetic experiments demonstrate that the compounds of the present invention have ideal pharmacokinetic characteristics, and their oral bioavailability is far more superior to that of the control drug, rivaroxaban.

3, In Vitro Anticoagulant Activity Assay of the Compound of the Present Invention Experimental Principle and Method:

The experiment used PRECIL C2000-1 immunomagnetic single channel semi-automated blood coagulation analyzer to measure blood coagulation time.

blank control, was recorded as APTT2, thereby evaluating the anticoagulant activity of the compounds.

3) Measurement of Thromboplastin Time (TT)

Principle: At 37° C., a "standard" thrombin solution is added to plasma, and the time needed for the coagulation of plasma is evaluated. This parameter reflects the activity of thrombin.

Test method: To the rabbit sodium citrate anticoagulant plasma (3.8% sodium citrate, 1:9 mixture) were added various concentrations of the compounds to be tested. TT reagents (PRECIL, Beijing) were used. The anticoagulant activity of the compounds was evaluated in comparison with the control group.

Experimental Contents:

Rabbit sodium citrate anticoagulant plasma (3.8% sodium citrate plasma, 1:9 mixture) was purchased from Guangzhou Ruite Bio company; PRECIL C2000-1 immunomagnetic single channel semi-automated blood coagulation analyzer and PRECIL blood coagulation 3-item reagents were purchased from Beijing PRECIL instrument company. The experiment had drug groups and a blank control group (using the same concentration of DMSO in stead of the subject compound; the plasma concentration of DMSO <0.1%, reaction time recorded as normal coagulation time). Each concentration of each sample was assayed in 3-6 duplicate wells, and the experiment was independently carried out for 2-3 times.

TABLE 5

In vitro anticoagulant activity data

| Compound | PT$_2$ (μM) | APTT$_2$ (μM) | TT |
|---|---|---|---|
| 1 | 0.184 | 0.141 | No compound affected TT at 10 μM. |
| 2 | 1.06 | 0.932 | |
| rivaroxaban | 0.399 | 0.315 | |

The data in Table 5 shows that the compounds of the present invention have very strong anticoagulant activity. They all significantly prolonged the PT time and APTT time of rabbit sodium citrate anticoagulant plasma. Furthermore, the anticoagulant activity of Compound 1 is superior to rivaroxaban. Additionally, the compounds of the present invention do not affect the activity of thrombin, and thus it is possible to reduce the risk of hemorrhage.

3, In Vivo Anticoagulant Activity Assay of the Compound of the Present Invention Experimental Method:

Male SD rats were randomly divided into 9 groups, which were solvent PEG400/anhydrous ethanol/water [40%/10%/50%] (5 ml/kg), rivaroxaban 2 mg/kg, 3 mg/kg, 6 mg/kg, 10 mg/kg, and Compound 1 2 mg/kg, 3 mg/kg, 6 mg/kg, and 10 mg/kg, respectively. The rats were fasted for 12 h, then weighted, and treated by intragastric administration. After 45 min, the rats were anesthetized with chloral hydrate (350 mg/kg), immobilized, and the left common carotid artery was exposed by surgery. The artery and the surrounding tissue were separated by plastic wrap. Electrical stimulation was started 1 h after intragastric administration.

The stimulation electrode of the BT87-4 tester for experimental in vivo thrombus formation was placed at the end of the blood vessels proximal to the heart. 3 mA current was used for a 2 min of stimulation. The instrument started the timer automatically when the stimulation began. The stimulation switch was turned off when the stimulation ended. The stimulation electrode was removed, and a thermostat probe was placed at the end of the artery on the stimulation site, which end is distal to the heart. At the time of 600 seconds, the pointer of the thermostat panel was slowly moved to the position of 0. The time from the start of simulation to the alarm of the instrument was recorded as the time of blood vessel blockage (or the time of thrombus formation). If a drug has antithrombosis effect, the time of thrombus formation (time of blood vessel blockage) will be prolonged. IBM SPSS Statistics 20 software was used for the t test of the experimental data. The experimental results are shown in FIG. 1.

Figure 2:
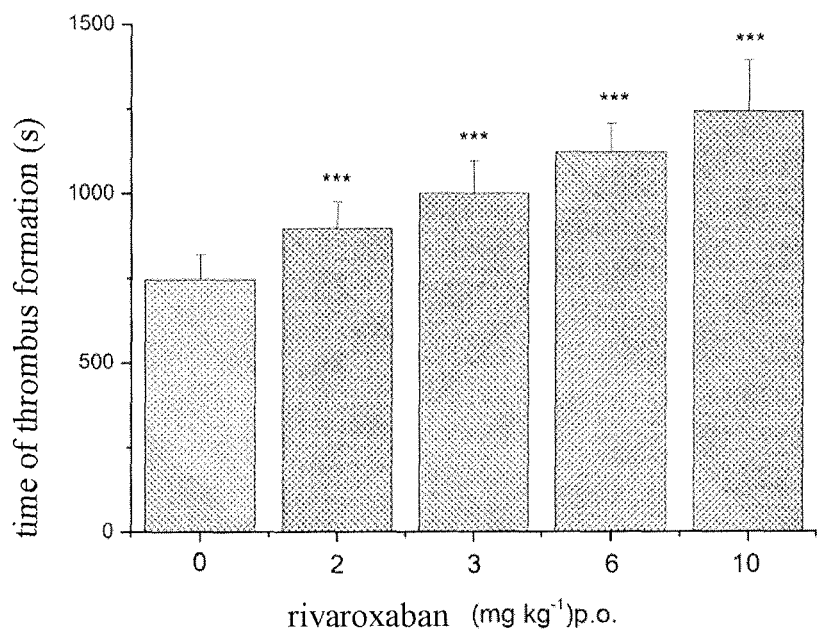
FIG. 2 depicts the effect of various dosages of the positive control rivaroxaban on the time of thrombogenesis.

From FIG. 1 and FIG. 2, it can be seen that the two compounds both had remarkable and dose-dependent effect of prolonging the time of thrombus formation. The effect of Compound 1 is stronger than that of the positive control rivaroxaban.

The ED50s of Compound 1 of the present invention and rivaroxaban for prolonging the thrombus formation time were 2.97 mg/kg and 4.53 mg/kg, respectively. This experiment indicates that the antithrombotic activity of the compounds of the present invention is significantly superior to that of the positive control, rivaroxaban. The activity of Compound 1 is 1.53 times of that of rivaroxaban, indicating that the compounds of the present invention can be an excellent anticoagulant agent for the treatment of thrombus-related diseases.

The invention claimed is:

1. An oxazolidone compound represented by the following formula (I), an enantiomer, diastereoisomer and racemate thereof as well as their mixtures, and a pharmaceutically acceptable salt thereof;

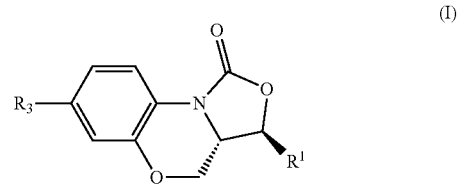

wherein, $R_1$ is —CH$_2$NHCOR$_2$, —CH$_2$CH$_2$NHCOR$_2$, —CONHR$_2$, —CONHCH$_2$R$_2$, —CH$_2$NHCONHR$_2$ or —CH$_2$NHCOCONHR$_2$;

$R_2$ is substituted or unsubstituted —(CH$_2$)$_n$—X—C$_m$H$_{2m+1}$, substituted or unsubstituted phenyl, substituted or unsubstituted 5- or 6-membered heterocyclic group, or substituted or unsubstituted benzo 5- or 6-membered heterocyclic group;

in said substituted or unsubstituted —(CH$_2$)$_n$—X—C$_m$H$_{2m+1}$, X is NH, O or S, and n and m are each an integer and n+m<6;

in the circumstance of substituted —(CH$_2$)$_n$—X—C$_m$H$_{2m+1}$, the substituent of C$_1$-C$_6$ alkyl or —(CH$_2$)$_n$—X—C$_m$H$_{2m+1}$ is a radical selected from the group consisting of: halogen, cyano, nitro, amino, aminomethyl, C$_1$-C$_8$ alkoxy, C$_3$-C$_7$ cycloalkyl or aminoformyl;

in the circumstance of substituted phenyl, the substituent of phenyl is a radical selected from the group consisting of: halogen, —NO$_2$, —CHO, —CF$_3$, —CONR$_4$R$_5$, —COR$_4$, —NHR$_5$, —NHCOR$_4$, —OR$_5$, —SO$_2$R$_4$, —SO$_2$NHR$_5$ or C$_1$-C$_3$ alkyl; said R$_4$ is C$_1$-C$_3$ alkyl, R$_5$ is H or C$_1$-C$_3$ alkyl;

said 5- or 6-membered heterocyclic group or benzo 5- or 6-membered heterocyclic group contains at least one heteroatom selected from N, O or S;

in the circumstance of substituted 5- or 6-membered heterocyclic group or substituted benzo 5- or 6-membered heterocyclic group, the substituent of 5- or 6-membered heterocyclic group or benzo 5- or 6-membered heterocyclic group is a radical selected from the group consisting of: halogen, —NO$_2$, —CHO, —CF$_3$, —CONR$_4$R$_5$, —NHR$_5$, —NHCOR$_4$, —OR$_5$, —SO$_2$R$_4$, —SO$_2$NHR$_5$, C$_1$-C$_3$ alkyl; said R$_4$ is C$_1$-C$_3$ alkyl, R$_5$ is H or C$_1$-C$_3$ alkyl;

R$_3$ is substituted or unsubstituted C$_1$~C$_3$ amido, substituted or unsubstituted phenyl or substituted or unsubstituted 5- or 6-membered aromatic or non-aromatic heterocyclic group;

in the circumstance of substituted C$_1$~C$_3$ amido, the H on N of said C$_1$~C$_3$ amido is substituted with C$_1$~C$_3$ alkyl;

in the circumstance of substituted phenyl, the substituent of phenyl is a radical selected from the group consisting of: F, Cl, Br, CN, —NO$_2$, —CF$_3$, —CONR$_4$R$_5$, —COR$_4$, —NHR$_5$, —NHCOR$_4$, —OR$_5$, —SO$_2$R$_4$, —SO$_2$NHR$_5$ or C$_1$-C$_3$ alkyl; said R$_4$ is C$_1$-C$_3$ alkyl, R$_5$ is H or C$_1$-C$_3$ alkyl;

said 5- or 6-membered aromatic heterocyclic group contains at least one heteroatom selected from N, O or S, and in the circumstance of substituted 5- or 6-membered aromatic heterocyclic group, the substituent of 5- or 6-membered aromatic heterocyclic group is a radical selected from the group consisting of: F, Cl, Br, CN, —NO$_2$, —CF$_3$, —CONR$_4$R$_5$, —COR$_4$, —NHR$_5$, —NHCOR$_4$, —OR$_5$, —SO$_2$R$_4$, —SO$_2$NHR$_5$ or C$_1$-C$_3$ alkyl; said R$_4$ is C$_1$-C$_3$ alkyl, R$_5$ is H or C$_1$-C$_3$ alkyl;

said 5- or 6-membered non-aromatic heterocyclic group contains at least one heteroatom selected from N, O or S, and said heterocyclic group can further form a spiroring with another 3 to 6-membered heterocyclic group; and in the circumstance of substituted 5- or 6-membered non-aromatic heterocyclic group, the substituent of 5- or 6-membered non-aromatic heterocyclic group is a radical selected from the group consisting of: oxo, F, Cl, Br, C$_1$-C$_3$ alkyl, CN, —NO$_2$, —CF$_3$, —CONR$_4$R$_5$, —COR$_4$, —COPh, —NHR$_5$, =NH, —NHCOR$_4$, —OR$_5$, —CH$_2$Ph, —SO$_2$R$_4$, —SO$_2$Ph, —SO$_2$NHR$_5$; said R$_4$ is C$_1$-C$_3$ alkyl, R$_5$ is H or C$_1$-C$_3$ alkyl.

2. The compound according to claim 1, an enantiomer, diastereoisomer and racemate thereof as well as their mixtures, and a pharmaceutically acceptable salt thereof, wherein, said R$_1$ is —CH$_2$NHCOR$_2$, —CONHR$_2$, —CH$_2$NHCONHR$_2$ or —CH$_2$NHCOCONHR$_2$;

said R$_2$ is substituted or unsubstituted —(CH$_2$)$_n$—X—C$_m$H$_{2m+1}$, substituted or unsubstituted phenyl, substituted or unsubstituted 5- or 6-membered heterocyclic group, or substituted or unsubstituted benzo 5- or 6-membered heterocyclic group;

in said substituted or unsubstituted —(CH$_2$)$_n$—X—C$_m$H$_{2m+1}$, X is NH, O or S, and n and m are each an integer and n+m<6;

in the circumstance of substituted —(CH$_2$)$_n$—X—C$_m$H$_{2m+1}$, the substituent of —(CH$_2$)$_n$—X—C$_m$H$_{2m+1}$ is halogen;

in the circumstance of substituted phenyl, the substituent of phenyl is a radical selected from the group consisting of: halogen, —OR$_5$; said R$_5$ is H or C$_1$-C$_3$ alkyl;

said 5- or 6-membered heterocyclic group or benzo 5- or 6-membered heterocyclic group contains at least one heteroatom selected from N, O or S;

in the circumstance of substituted 5- or 6-membered heterocyclic group or substituted benzo 5- or 6-membered heterocyclic group, the substituent of 5- or 6-membered heterocyclic group or benzo 5- or 6-membered heterocyclic group is halogen or —OR$_5$; said R$_5$ is H or C$_1$-C$_3$ alkyl;

said R$_3$ is N-methylacetamido, substituted or unsubstituted phenyl or substituted or unsubstituted 5- or 6-membered non-aromatic heterocyclic group;

in the circumstance of substituted phenyl, the substituent of phenyl is a radical selected from the group consisting of: —SO$_2$R$_4$, —SO$_2$NHR$_5$; said R$_4$ is C$_1$-C$_3$ alkyl, preferably methyl, R$_5$ is H or C$_1$-C$_3$ alkyl, preferably, H;

said 5- or 6-membered non-aromatic heterocyclic group contains at least one heteroatom selected from N, O or S, and said heterocyclic group can further form a spiroring with another 5 to 6-membered heterocyclic group; and in the circumstance of substituted 5- or 6-membered non-aromatic heterocyclic group, the substituent of 5- or 6-membered non-aromatic heterocyclic group is a radical selected from the group consisting of: oxo, F, Cl, Br, C$_1$-C$_3$ alkyl, —COR$_4$, =NH, —OR$_5$, —CH$_2$Ph, —SO$_2$R$_4$, —SO$_2$Ph; said R$_4$ is C$_1$-C$_3$ alkyl, R$_5$ is H or C$_1$-C$_3$ alkyl.

3. The compound according to claim 1, an enantiomer, diastereoisomer and racemate thereof as well as their mixtures, and a pharmaceutically acceptable salt thereof, wherein, said R$_1$ is —CH$_2$NHCOR$_2$, —CONHR$_2$, —CH$_2$NHCONHR$_2$ or —CH$_2$NHCOCONHR$_2$;

said R$_2$ is

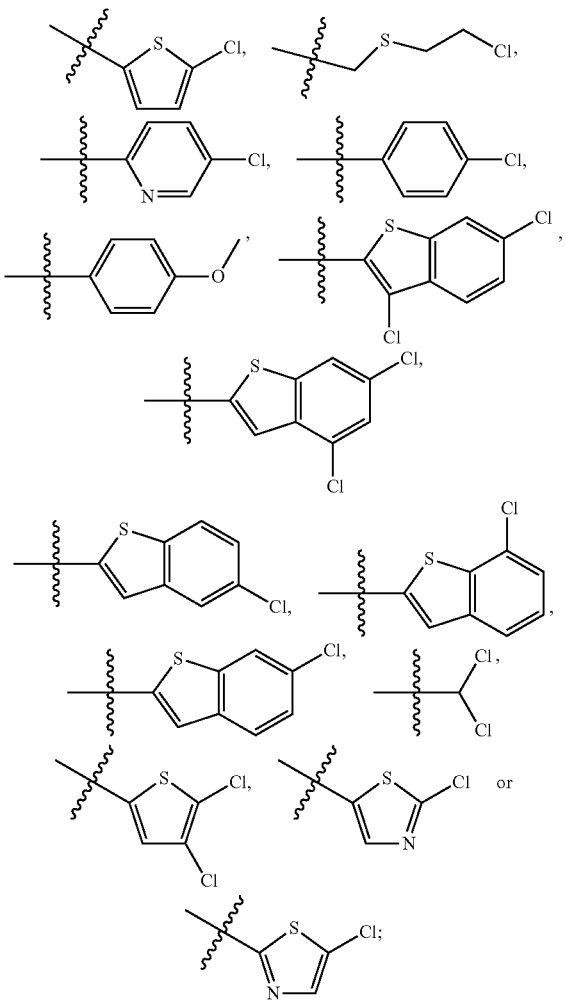

and/or said R$_3$ is

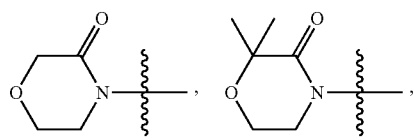

-continued
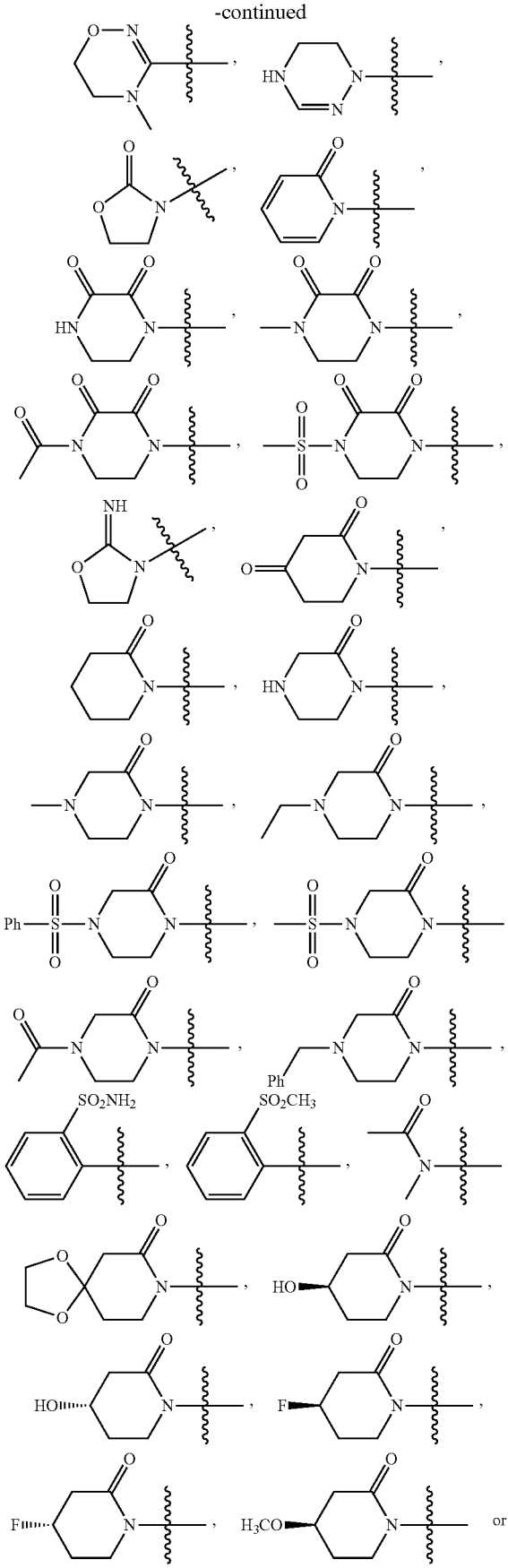
-continued
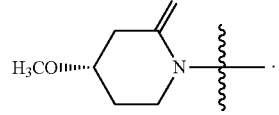
4. The compound according to claim 1, an enantiomer, diastereoisomer and racemate thereof as well as their mixtures, and a pharmaceutically acceptable salt thereof, wherein,
said compound is the following compound:
Compound 1
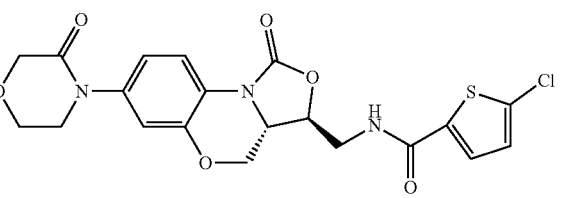
Compound 2
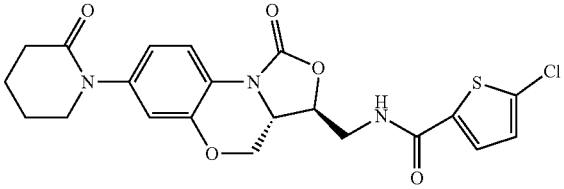
Compound 3
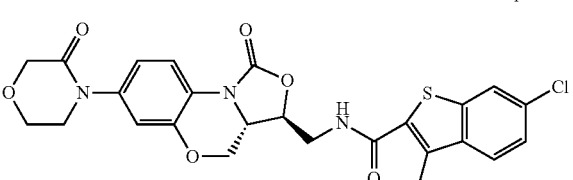
Compound 4
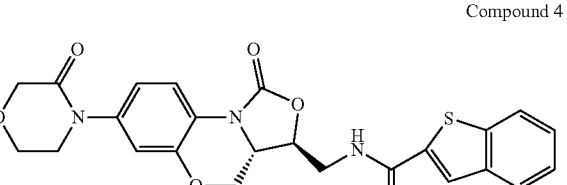
Compound 5
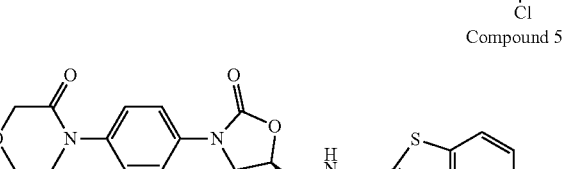
Compound 6
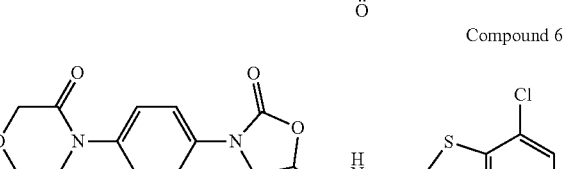

Compound 7
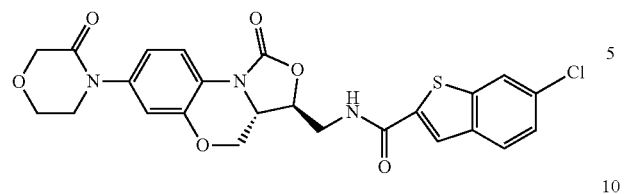
Compound 8
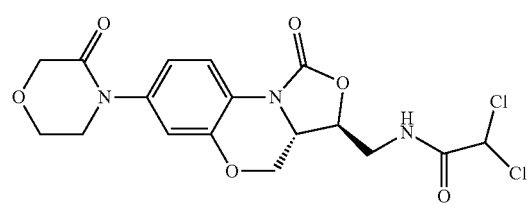
Compound 9
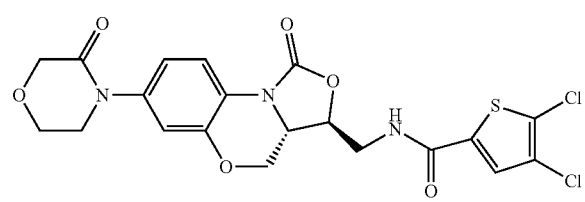
Compound 10
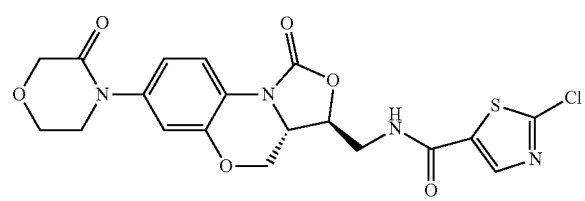
Compound 11
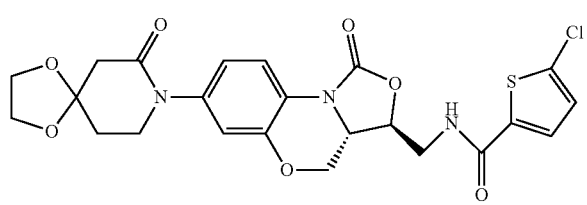
Compound 12
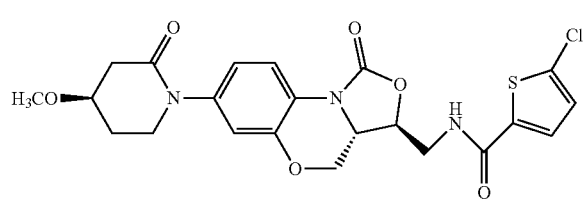
Compound 13
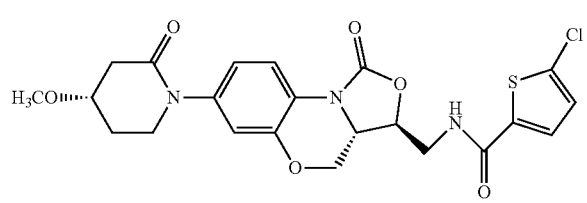
Compound 14
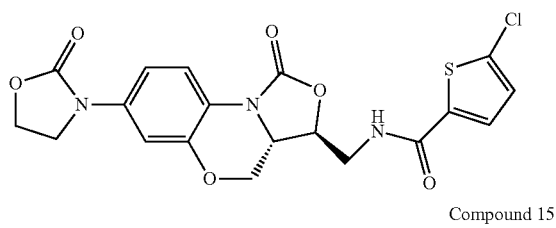
Compound 15
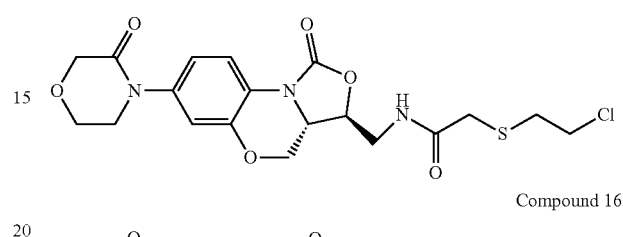
Compound 16
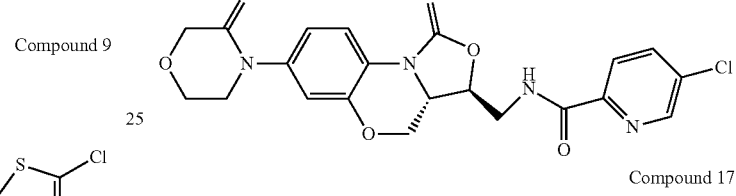
Compound 17
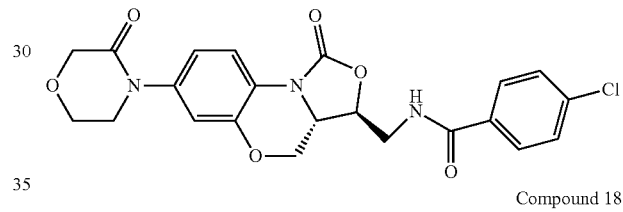
Compound 18
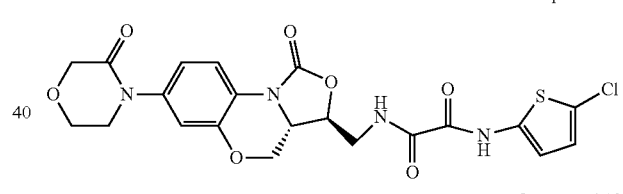
Compound 19
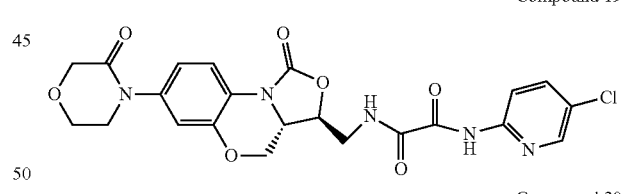
Compound 20
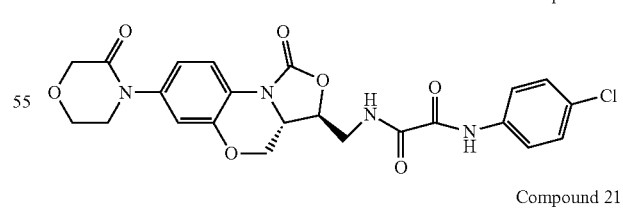
Compound 21
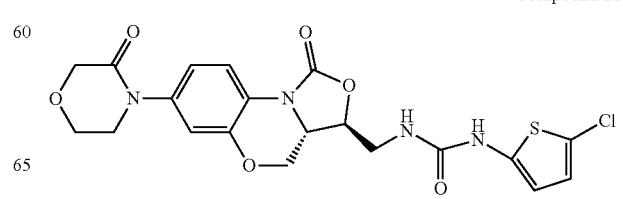

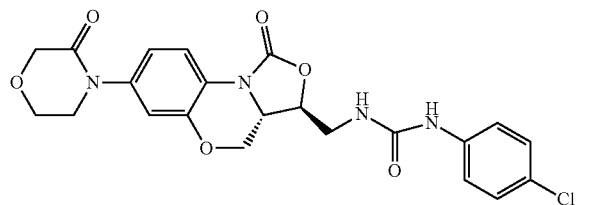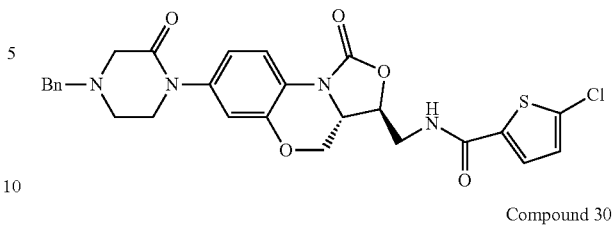

Compound 36
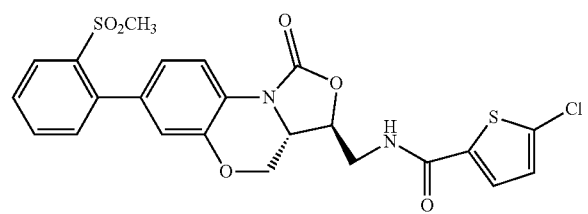
Compound 39
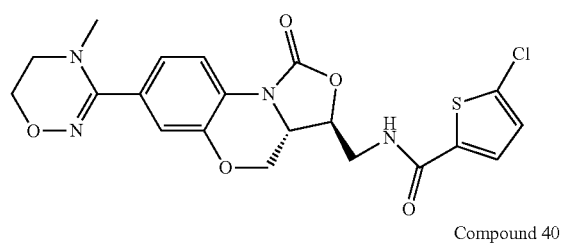
Compound 40
Compound 37
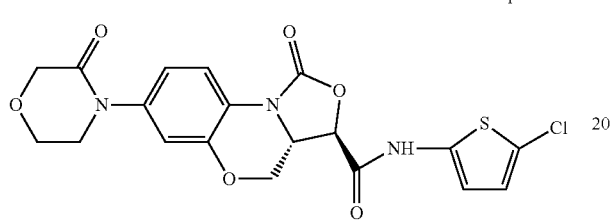
5. A method for preparing the compound represented by formula (I),
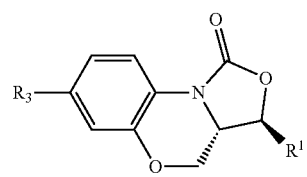
(I)
Compound 38
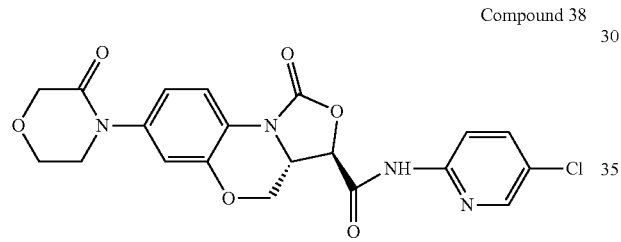
wherein, $R_1$ and $R_3$ are defined as in claim 1;
wherein, the method is selected from one of the following methods:
Method 1
  Route 1
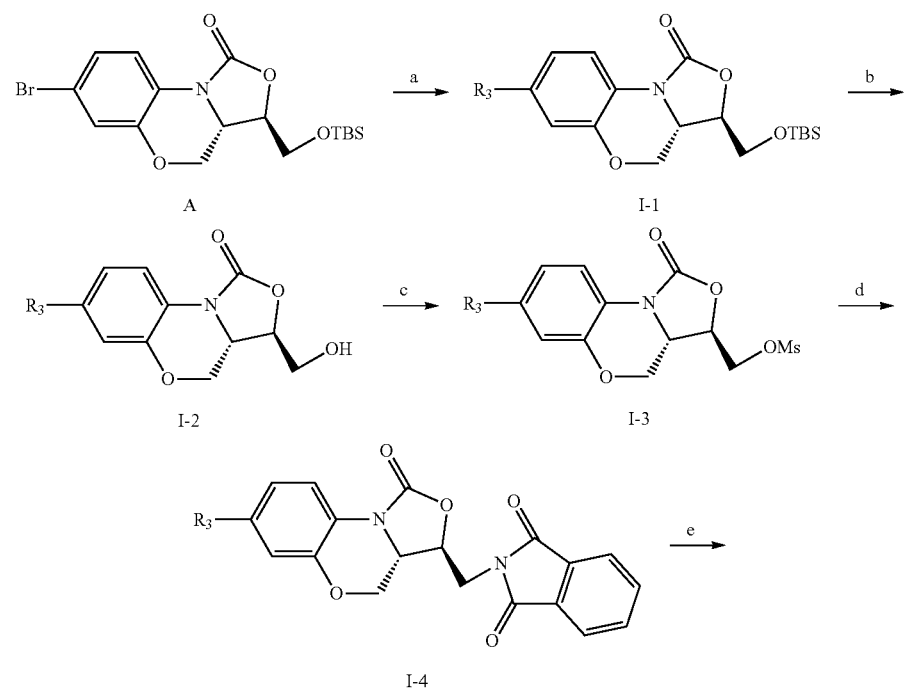

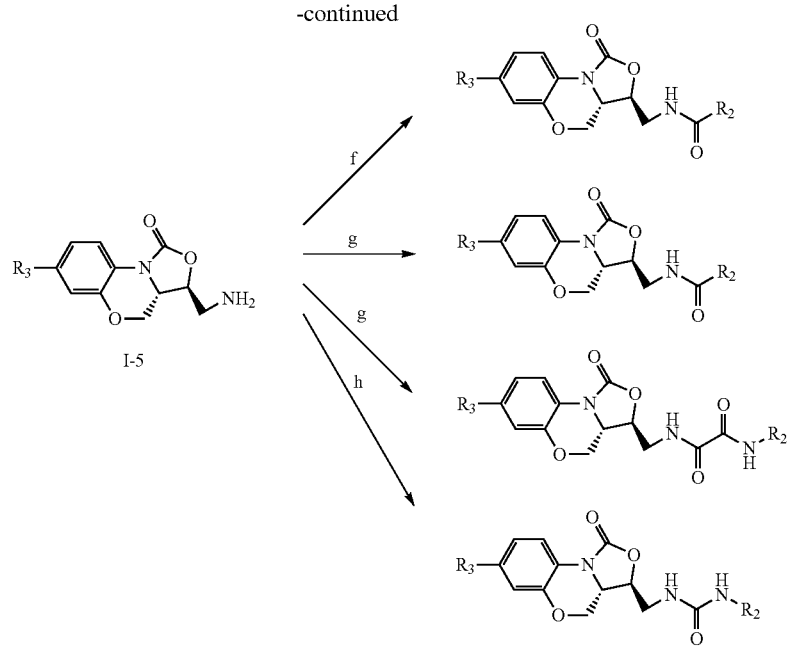

a, compound A and compound R₃H react, with the catalysation by a palladium-containing catalyst, in the presence of a phosphine-containing ligand, in a polar aprotic solvent under alkaline condition, under the protection of inert gas at a temperature from room temperature to 120° C. for 2-48 hours, to give compound I-1;

b, compound I-1 reacts, in the presence of a fluorine-containing reagent, in a polar aprotic solvent, at room temperature for 1-3 hours, to remove the protecting group t-butyldimethylsilyl (TBS), thereby giving compound I-2;

c, compound I-2 and methylsulfonyl chloride (MsCl) react, in the presence of an organic base, in a polar aprotic solvent, at a temperature from −10° C. to room temperature for 1-3 hours, to give the corresponding compound I-3;

d, compound I-3 and phthalimide potassium react, in a polar aprotic solvent, at a temperature from room temperature to 100° C. for 1-24 hours, to give the corresponding compound I-4;

e, compound I-4 and methylamine alcohol solution react in a polar solvent at a temperature from room temperature to 80° C. for 1-12 hours, to give the corresponding compound I-5;

f, compound I-5 and R₂ substituted acyl chloride, in the presence of an organic base, in a polar aprotic solvent, at a temperature from −10° C. to room temperature for 1-3 hours, to give the corresponding compound;

g, compound I-5 and R₂ substituted carboxylic acid or amino oxalic acid substituted with R₂ at its N position react, in the presence of a condensation agent and an organic base, in a polar solvent, at room temperature for 1-6 hours, to give the corresponding compound;

h, compound I-5 and R₂ substituted isocyanate react, in a solvent at a temperature from room temperature to 110° C. for 3-24 hours, to give the corresponding product;

Method 2
Route 5

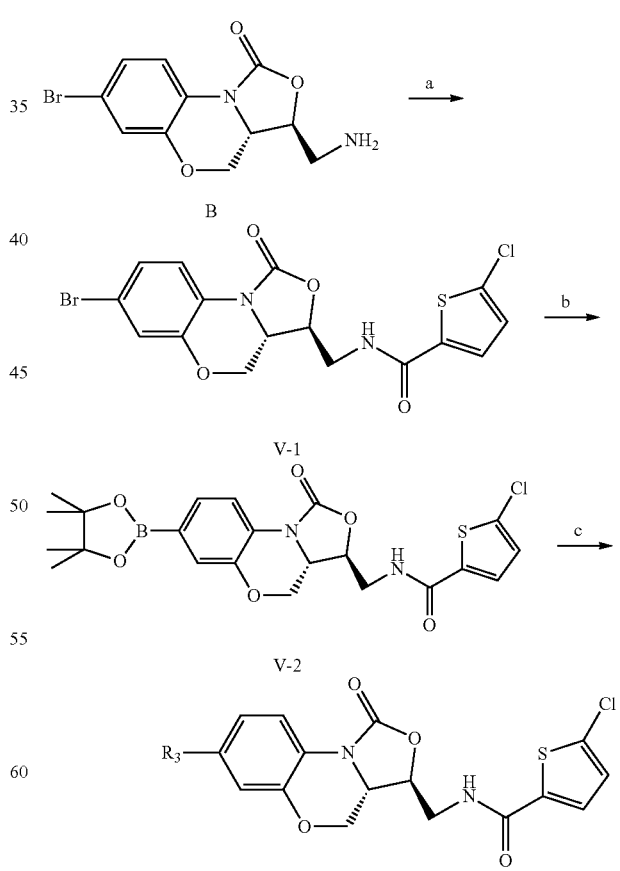

a, compound B and 2-chlorothiophene-5-formyl chloride react, in the presence of an organic base, in a polar aprotic solvent, at a temperature from −10° C. to room temperature for 1-3 hours, to give compound V-1;

b, compound V-1 and bis(pinacolato)diboron react, with the catalysation by a palladium-containing catalyst, in the presence of a phosphine-containing ligand, in a polar solvent under alkaline condition, under the protection of inert gas at a temperature from room temperature to 110° C. for 0.5-48 hours, to give compound V-2;

c, compound V-2 and the bromide $R_3Br$ react, with the catalysation by a palladium-containing catalyst, in a polar solvent under alkaline condition, under the protection of inert gas at a temperature from room temperature to 120° C. for 2-24 hours, to give the corresponding compound;

Method 3

Route 6

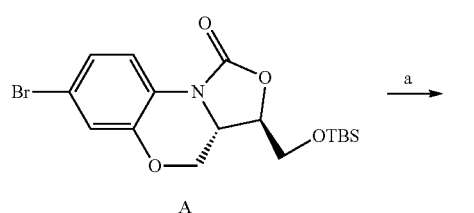

A

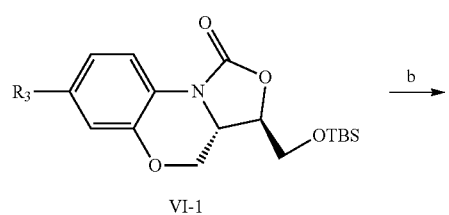

VI-1

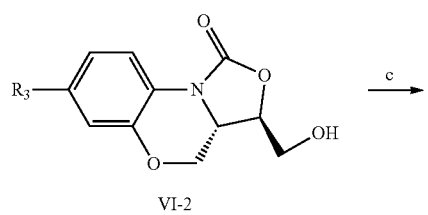

VI-2

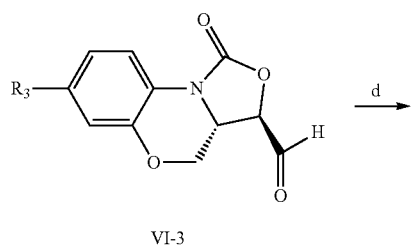

VI-3

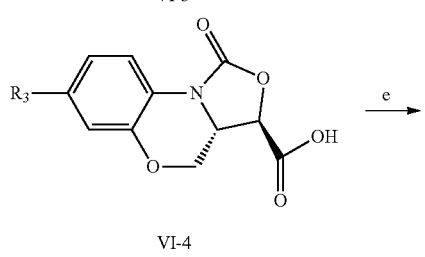

VI-4

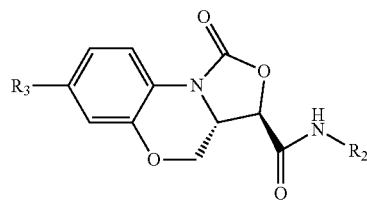

a, compound A and compound $R_3H$ react, with the catalysation by a palladium-containing catalyst, in the presence of a phosphine-containing ligand, in a polar aprotic solvent under alkaline condition, under the protection of inert gas at a temperature from room temperature to 120° C. for 2-48 hours, to give compound VI-1;

b, compound VI-1 reacts, in the presence of a fluorine-containing reagent, in a polar aprotic solvent, at room temperature for 1-3 hours, to remove the protecting group t-butyldimethylsilyl, thereby giving compound VI-2;

c, compound VI-2 reacts with an oxidizing agent in a polar aprotic solvent at a temperature from 0° C. to room temperature for 1-6 hours, to give the corresponding compound VI-3;

d, compound VI-3 reacts with an oxidizing agent in a polar aprotic solvent and a buffer solution at room temperature for 1-24 hours to give the corresponding compound VI-4;

e, compound VI-4 and a $R_2$ substituted amine react, in the presence of a condensation agent and an organic base, in a polar aprotic solvent, at room temperature for 1-6 hours, to give the corresponding compound;

Method 4

Route 7

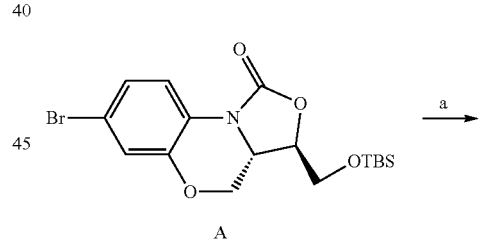

A

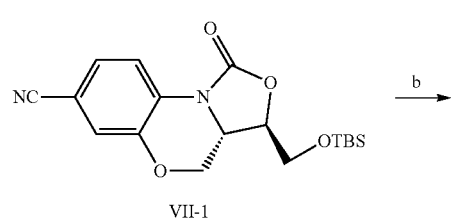

VII-1

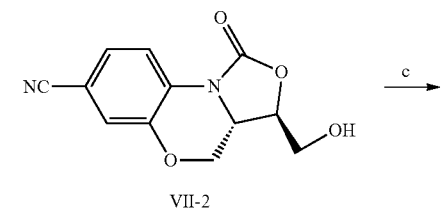

VII-2

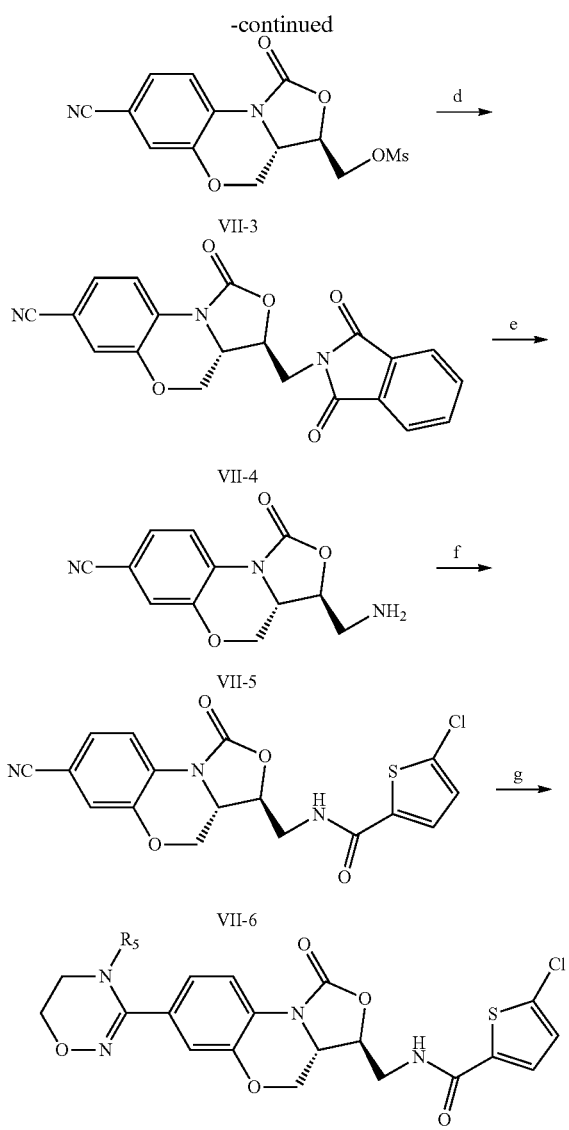

a, compound A and compound potassium ferrocyanide(II) trihydrate [KFe(CN)₆·3H₂O] react, with the catalysation by a palladium-containing catalyst, in a polar aprotic solvent under alkaline condition, under the protection of inert gas at a temperature from room temperature to 150° C. for 0.5-12 hours, to give compound VII-1;

b, compound VII-1 reacts, in the presence of a fluorine-containing reagent, in a polar aprotic solvent, at room temperature for 1-3 hours, to remove the protecting group t-butyldimethylsilyl (TBS), thereby giving compound VII-2;

c, compound VII-2 and methylsulfonyl chloride (MsCl) react, in the presence of an organic base, in a polar aprotic solvent, at a temperature from −10° C. to room temperature for 1-3 hours, to give the corresponding compound VII-3;

d, compound VII-3 and phthalimide potassium react, in a polar aprotic solvent, at a temperature from room temperature to 100° C. for 1-24 hours, to give the corresponding compound VII-4;

e, compound VII-4 and methylamine alcohol solution react in a polar solvent at a temperature from room temperature to 80° C. for 1-12 hours, to give the corresponding compound VII-5;

f, compound VII-5 and a R₂ substituted acyl chloride react, in the presence of an organic base, in a polar aprotic solvent, at a temperature from −10° C. to room temperature for 1-3 hours, to give the corresponding compound VII-6;

g, compound VII-6 in an alcohol solvent was bubbled with hydrogen chloride gas at 0° C. for 2-6 h, and then stirred at room temperature for 2-6 h; after compound VII-6 reacts completely, the solvent and the residual acid are removed by evaporation; the resulting mixture and 2-aminooxy-N-R5-ethylamine react under reflux in a polar protic solvent for 10-24 h, to give the corresponding compound; wherein each $R_1$, $R_2$, $R_3$ and $R_5$ is defined as in claim 1.

6. A pharmaceutical composition, which comprises one or more of the compound according to claim 1, an enantiomer, diastereoisomer and racemate thereof as well as their mixtures, and a pharmaceutically acceptable salt thereof, as the main active ingredient, and one or more of pharmaceutically acceptable auxiliary materials.

7. The pharmaceutical composition according to claim 6, wherein the pharmaceutical composition is formulated into tablet, capsule, granules, or syrup for oral administration.

8. The compound according to claim 1, an enantiomer, diastereoisomer or racemate thereof as well as their mixtures, or pharmaceutically acceptable salts thereof, wherein,
said $R_1$ is —CH₂NHCOR₂, —CONHR₂, —CH₂NHCONHR₂ or —CH₂NHCOCONHR₂; and
said $R_2$ is substituted or unsubstituted —(CH₂)ₙ—X—$C_mH_{2m+1}$, substituted or unsubstituted phenyl, substituted or unsubstituted 5- or 6-membered heterocyclic group, or substituted or unsubstituted benzo 5- or 6-membered heterocyclic group.

9. A method for treatment of a thrombus related disease selected from the group consisting of myocardial infarction, ischemic stroke, deep venous thrombosis and pulmonary embolism, comprising administering the compound of claim 1 to a subject in need thereof.

10. The method of claim 9, wherein the subject is a human.

11. A method for inhibiting coagulation factor FXa activity, the method comprising the step of administrating the compound of claim 1 to a subject in need.

12. The method of claim 11, wherein the subject is a human.

* * * * *